(12) United States Patent
Grabowski et al.

(10) Patent No.: US 7,202,027 B1
(45) Date of Patent: Apr. 10, 2007

(54) NUCLEIC ACID MOLECULES FOR DETECTING BACTERIA AND PHYLOGENETIC UNITS OF BACTERIA

(75) Inventors: Reiner Grabowski, Goettingen (DE); Kornelia Berghof, Berlin (DE)

(73) Assignee: Biotecon Diagnostics GmbH, Berlin (DE)

( * ) Notice: Subject to any disclaimer, the term of this patent is extended or adjusted under 35 U.S.C. 154(b) by 317 days.

(21) Appl. No.: 10/088,966

(22) PCT Filed: Sep. 8, 2000

(86) PCT No.: PCT/EP00/08813

§ 371 (c)(1),
(2), (4) Date: Mar. 22, 2002

(87) PCT Pub. No.: WO01/23606

PCT Pub. Date: Apr. 5, 2001

(30) Foreign Application Priority Data

Sep. 24, 1999 (DE) ................ 199 45 916

(51) Int. Cl.
*C12Q 1/68* (2006.01)
(52) U.S. Cl. .............. 435/6; 435/91.1; 435/91.2; 435/23.1
(58) Field of Classification Search .......... 435/6, 435/91.1, 91.2; 536/23.1
See application file for complete search history.

(56) References Cited

U.S. PATENT DOCUMENTS 5,654,141 A * 8/1997 Mariani et al. ............ 435/6
5,776,680 A 7/1998 Leibowitz et al.

FOREIGN PATENT DOCUMENTS

| DE | 196 16 750 A1 | 11/1997 |
|---|---|---|
| DE | 197 31 292 A1 | 1/1999 |
| DE | 197 39 611 A1 | 3/1999 |
| EP | 0 472 434 A2 | 2/1992 |
| EP | 0 739 988 A1 | 10/1996 |
| WO | WO 90/15157 A1 | 12/1990 |
| WO | WO 93/11264 A1 | 6/1993 |
| WO | WO 95/13396 A | 5/1995 |

OTHER PUBLICATIONS

Brosius, Jurgen, Thomas J. Dull, Donald D. Sleeter, Harry F. Noller, Gene organization and primary structure of a ribosomal RNA operon from *Escherichia coli*. Journal of Molecular Biology. 148(2): 107-127.*

Yamamoto et al. Genebank accession No. AB001340, submitted Jan. 25, 1997.*
Buck et al. Biotechniques. 1999. vol. 27(3):528-536.*
Breidt et al., *Chem. Abstr.*,125(5), Abstract No. 50197q, 263 (1996) & *J. Rapid Methods Autom. Microbiol.*, 4, 219-233 (1996).
Fan et al., *Database Medline*, Database Accession No. AN 96034419 & *J. Medical and Veterinary Mycology*, 33, 215-221 (1995).
Frothigham et al., *Chem. Abstr.*,129(8), Abstract No. 91244d, 200-201 (1998) & *Microbiology Reading*, 144, 1189-1196 (1998).
Gazumyan et al., *Gene*, 146, 57-65 (1994).
Kim et al., *Gene*, 132, 21-31 (1993).
Kohler et al., *Database Medline*, Database Accession No. AN 92209976 & *FEMS Microbiol Lett.*, 68, 307-312 (1991).
Maslov et al., *Database Medline*, Database Accession No. AN 94081857 & *Molecular and Biochemical Parasitology*, 61, 127-135 (1993).
Mehling et al., *Chem. Abstr.*, 123, Abstract No. 134255d, 298 (1995) & *FEMS Microbiol. Lett.*, 128, 119-125 (1995).
Molina et al., *Database Medline*, Database Accession No. AN 9329903 & *FEMS Microbiol. Lett.*, 108, 259-263 (1993).
Normand et al., *Gene*, 111, 119-124 (1992).
Nour, *Chem. Abstr.*, 130 (10), Abstract No. 120332j, 186-187 (1999) & *Can. J. Microbiol.*, 44, 807-818 (1998).
Nour, *Database Medline*, Database Accession No. AN 1998439380 & *Research in Microbiology*, 149, 433-448 (1998).
Pernodet et al., *Gene*, 79, 33-46 (1989).
Rijpkema et al., *Chem. Abstr.*, 124(11), Abstract No. 136858x, 279 (1996) & *J. Clin. Microbiol.*, 33, 3091-3095 (1995).
Stucki et al., *Database Medline*, Database Accession No. AN 93223829 & *Experimental Parasitology*, 76, 68-75 (1993).
Van Den Hombergh et al., *Chem. Abstr.*, 125(1), Abstract No. 266832r, 261 (1996) & *Laboratoriumsmedizin*, 20, 500-503 (1996).
Zhu et al., *Chem. Abstr.*, 124 (23), Abstract No. 308709t, 313-314 (1996) & *J. Appl. Bacteriol.*, 80, 244-251 (1996).
Ana et al., *J. Bacteriol.*, 181(9), 2703-2709 (May 1999).
Blattner et al., *Science*, 277, 1453-1462 (Sep. 5, 1997).
Brenner et al., *J. Bacteriol.*, 129(3), 1435-1439 (Mar. 1977).

* cited by examiner

*Primary Examiner*—Teresa E. Strzelecka
*Assistant Examiner*—Heather G. Calamita
(74) *Attorney, Agent, or Firm*—Leydig, Voit & Mayer, Ltd.

(57) ABSTRACT

The present invention relates to nucleic acid molecules which allow the identification of bacteria or groups of bacteria. For detection, the region of the bacterial genome containing the 23 S/5 S rRNA is used as the target sequence for the bacterial detection.

10 Claims, 8 Drawing Sheets

SEQUENCE LISTING

<160> NUMBER OF SEQ ID NOS: 530

<210> SEQ ID NO 1
<211> LENGTH: 3118
<212> TYPE: DNA
<213> ORGANISM: Escherichia coli

<400> SEQUENCE: 1

```
ggttaagcga ctaagcgtac acggtggatg ccctggcagt cagaggcgat gaaggacgtg      60
ctaatctgcg ataagcgtcg gtaaggtgat atgaaccgtt ataaccggcg atttccgaat     120
ggggaaaccc agtgtgtttc gacacactat cattaactga atccataggt taatgaggcg     180
aaccggggga actgaaacat ctaagtaccc cgaggaaaag aaatcaaccg agattccccc     240
agtagcggcg agcgaacggg gagcagccca gagcctgaat cagtgtgtgt gttagtggaa     300
gcgtctggaa aggcgtgcga tacagggtga cagccccgta cacaaaaatg cacatgctgt     360
gagctcgatg agtaggggcg gacacgtggt atcctgtctg aatatgggg gaccatcctc     420
```

-continued

```
caaggctaaa tactcctgac tgaccgatag tgaaccagta ccgtgaggga aaggcgaaaa      480 gaacccggc gagggagtg aaaaagaacc tgaaaccgtg tacgtacaag cagtgggagc       540
acgcttaggc gtgtgactgc gtacctttg tataatggt cagcgactta tattctgtag       600
caaggttaac cgatagggg agccgaaggg aaaccgagtc ttaactgggc gttaagttgc      660
agggtataga cccgaaaccc ggtgatctag ccatgggcag gttgaaggtt gggtaacact     720
aactggagga ccgaaccgac taatgttgaa aaattagcgg atgacttgtg gctggggtg      780 aaaggccaat caaaccggga gatagctggt tctccccgaa agctatttag gtagcgcctc     840
gtgaattcat ctccgggggt agagcactgt ttcggcaagg gggtcatccc gacttaccaa     900
cccgatgcaa actgcgaata ccggagaatg ttatcacggg agacacacgg cgggtgctaa    960
cgtccgtcgt gaagagggaa acaacccaga ccgccagcta aggtcccaaa gtcatggtta   1020
agtgggaaac gatgtgggaa ggcccagaca gccaggatgt tggcttagaa gcagccatca   1080 tttaagaaa gcgtaatagc tcactggtcg agtcggcctg cgcggaagat gtaacggggc    1140 taaccatgc accgaagctg cggcagcgac actatgtgtt gttgggtagg ggagcgttct    1200
gtaagcctgt gaaggtgtgc tgtgaggcat gctggaggta tcagaagtgc gaatgctgac   1260
ataagtaacg ataaagcggg tgaaaagccc gctcgccgga agaccaaggg ttcctgtcca   1320
acgttaatcg gggcagggtg agtcgacccc taaggcgagg ccgaaaggcg tagtcgatgg   1380
gaaacaggtt aatattcctg tacttggtgt tactgcgaag ggggacgga aaggctatg     1440 ttggccgggc gacggttgtc ccggtttaag cgtgtaggct ggttttccag gcaaatccgg   1500
aaaatcaagg ctgaggcgtg atgacgaggc actacggtgc tgaagcaaca aatgccctgc   1560
ttccaggaaa agcctctaag catcaggtaa catcaaatcg taccccaaac cgacacaggt   1620
ggtcaggtag agaataccaa ggcgcttgag agaactcggg tgaaggaact aggcaaaatg   1680
gtgccgtaac ttcgggagaa ggcacgctga tatgtaggtg aagcgacttg ctcgtggagc   1740
tgaaatcagt cgaagatacc agctggctgc aactgtttat taaaaacaca gcactgtgca   1800
aacacgaaag tggacgtata cggtgtgacg cctgcccggt gccggaaggt taattgatgg   1860
ggttagccgc aaggcgaagc tcttgatcga agccccggta aacggcggcc gtaactataa   1920
cggtcctaag gtagcgaaat tccttgtcgg gtaagttccg acctgcacga atggcgtaat   1980
gatggccagg ctgtctccac ccgagactca gtgaaattga actcgctgtg aagatgcagt   2040
gtacccgcgg caagacgaa agaccccgtg aacctttact atagcttgac actgaacatt    2100
gagccttgat gtgtaggata ggtgggaggc tttgaagtgt ggacgccagt ctgcatggag   2160
ccgaccttga ataccaccc tttaatgttt gatgttctaa cgttgacccg taatccgggt    2220
tgcggacagt gtctggtggg tagtttgact ggggcggtct cctcctaaag agtaacggag   2280
gagcacgaag gttggctaat cctggtcgga catcaggagg ttagtgcaat ggcataagcc   2340
agcttgactg cgagcgtgac ggcgcgagca ggtgcgaaag caggtcatag tgatccggtg   2400
gttctgaatg gaagggccat cgctcaacgg ataaaaggta ctccggggat aacaggctga   2460
taccgcccaa gagttcatat cgacggcggt gtttggcacc tcgatgtcgg ctcatcacat   2520 cctgggctg aagtaggtcc caagggtatg gctgttcgcc atttaaagtg gtacgcgagc    2580
tgggtttaga acgtcgtgag acagttcggt ccctatctgc cgtgggcgct ggagaactga   2640 gggggctgc tcctagtacg agaggaccgg agtggacgca tcactggtgt tcgggttgtc    2700
atgccaatgg cactgcccgg tagctaaatg cggaagagat aagtgctgaa agcatctaag   2760
cacgaaactt gccccgagat gagttctccc tgactccttg agagtcctga aggaacgttg   2820
```

```
aagacgacga cgttgatagg ccgggtgtgt aagcgcagcg atgcgttgag ctaaccggta    2880
ctaatgaacc gtgaggctta accttacaac gccgaaggtg tttttggcgga ttgagagaag    2940 attttcagcc tgatacagat taaatcagaa cgcagaagcg gtctgataaa acagaatttg    3000
cctggcggca gtagcgcggt ggtcccacct gacccccatgc cgaactcaga agtgaaacgc    3060
cgtagcgccg atggtagtgt ggggtctcct catgcgagag tagggaactg ccaggcat      3118

<210> SEQ ID NO 2
<211> LENGTH: 20
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 2
ttcgggttgt catgccaatg                                                  20

<210> SEQ ID NO 3
<211> LENGTH: 26
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 3
ctgaaagcat ctaagcgcga aacttg                                           26

<210> SEQ ID NO 4
<211> LENGTH: 26
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 4
ctgaaagcat ctaagcggga aacttg                                           26

<210> SEQ ID NO 5
<211> LENGTH: 26
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 5
ctgaaagcat ctaagcacga aacttg                                           26

<210> SEQ ID NO 6
<211> LENGTH: 26
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 6
ctgaaagcat ctaagcagga aacttg                                           26

<210> SEQ ID NO 7
<211> LENGTH: 25
```

```
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 7
gggaggactc atctcgaggc aagtt                                           25

<210> SEQ ID NO 8
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 8
gggaggactc atctcggggc aagtt                                           25

<210> SEQ ID NO 9
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 9
gggaggactc atctcaaggc aagtt                                           25

<210> SEQ ID NO 10
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 10
gggaggactc atctcagggc aagtt                                           25

<210> SEQ ID NO 11
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 11
gggaggactc atcttgaggc aagtt                                           25

<210> SEQ ID NO 12
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 12
gggaggactc atcttggggc aagtt                                           25

<210> SEQ ID NO 13
<211> LENGTH: 25
<212> TYPE: DNA
```

<213> ORGANISM: Artificial sequence
<220> FEATURE:
<223> OTHER INFORMATION: Description of the artificial sequence: derived
      from genera of enterobacteria

<400> SEQUENCE: 13
gggaggactc atcttaaggc aagtt                                   25

<210> SEQ ID NO 14
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 14
gggaggactc atcttagggc aagtt                                   25

<210> SEQ ID NO 15
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 15
gggagaactc atctcgaggc aagtt                                   25

<210> SEQ ID NO 16
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 16
gggagaactc atctcggggc aagtt                                   25

<210> SEQ ID NO 17
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 17
gggagaactc atctcaaggc aagtt                                   25

<210> SEQ ID NO 18
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 18
gggagaactc atctcagggc aagtt                                   25

<210> SEQ ID NO 19
<211> LENGTH: 25
<212> TYPE: DNA
<213> ORGANISM: Artificial sequence

```
<220> FEATURE:
<223> OTHER INFORMATION: Description of the artificial sequence: derived
      from genera of enterobacteria

<400> SEQUENCE: 19
gggagaactc atcttgaggc aagtt                                              25

<210> SEQ ID NO 20
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 20
gggagaactc atcttggggc aagtt                                              25

<210> SEQ ID NO 21
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 21
gggagaactc atcttaaggc aagtt                                              25

<210> SEQ ID NO 22
<211> LENGTH: 25
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 22
gggagaactc atcttagggc aagtt                                              25

<210> SEQ ID NO 23
<211> LENGTH: 18
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 23
ccgccaggca aattcggt                                                      18

<210> SEQ ID NO 24
<211> LENGTH: 17
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 24
tcaggtggga ccaccgc                                                       17

<210> SEQ ID NO 25
<211> LENGTH: 18
<212> TYPE: DNA
<213> ORGANISM: Artificial sequence
<220> FEATURE:
```

```
          -continued

<223> OTHER INFORMATION: Description of the artificial sequence: derived
      from genera of enterobacteria

<400> SEQUENCE: 25
ccgccaggca aattctgt                                                18

<210> SEQ ID NO 26
<211> LENGTH: 54
<212> TYPE: DNA
<213> ORGANISM: Artificial sequence
<220> FEATURE:
<223> OTHER INFORMATION: Description of the artificial sequence: derived
      from species of the genus enterobacteria

<400> SEQUENCE: 26
ccggagtgga cgcaccactg gtgttcgggt tgtcatgcca atggcattgc ccgg        54

<210> SEQ ID NO 27
<211> LENGTH: 54
<212> TYPE: DNA
<213> ORGANISM: Artificial sequence
<220> FEATURE:
<223> OTHER INFORMATION: Description of the artificial sequence: derived
      from species of the genus Acinetobacter

<400> SEQUENCE: 27
ccagagtgga cgaacctctg gtgtaccggt tgtgacgcca gtcgcatcgc cggg        54

<210> SEQ ID NO 28
<211> LENGTH: 54
<212> TYPE: DNA
<213> ORGANISM: Artificial sequence
<220> FEATURE:
<223> OTHER INFORMATION: Description of the artificial sequence: derived
      von from species of the genus Aeromonas

<400> SEQUENCE: 28
ccggagtgaa cgaacctctg gtgttcgggt tgtcacgcca gtggcactgc ccgg        54

<210> SEQ ID NO 29
<211> LENGTH: 54
<212> TYPE: DNA
<213> ORGANISM: Artificial sequence
<220> FEATURE:
<223> OTHER INFORMATION: Description of the artificial sequence: derived
      from species of the genus Haemophilus

<400> SEQUENCE: 29
ccggagtgga cgcatcactg gtgttccggt tgtgtcgcca gacgcattgc cggg        54

<210> SEQ ID NO 30
<211> LENGTH: 54
<212> TYPE: DNA
<213> ORGANISM: Artificial sequence
<220> FEATURE:
<223> OTHER INFORMATION: Description of the artificial sequence: derived
      from species of the genus Moraxella

<400> SEQUENCE: 30
ccggagtgga cgcatcactg gtgttccggt tgtgtcgcca gacgcattgc cggg        54

<210> SEQ ID NO 31
<211> LENGTH: 54
<212> TYPE: DNA
<213> ORGANISM: Artificial sequence
<220> FEATURE:
<223> OTHER INFORMATION: Description of the artificial sequence: derived
``` from species of the genus Pasteurella

<400> SEQUENCE: 31
ccgggatgga cacaccgctg gtgtaccagt tgttctgcca agagcatcgc tggg        54

<210> SEQ ID NO 32
<211> LENGTH: 54
<212> TYPE: DNA
<213> ORGANISM: Artificial sequence
<220> FEATURE:
<223> OTHER INFORMATION: Description of the artificial sequence:
      derived from species of the
      genus Stenotrophomonas

<400> SEQUENCE: 32
ccggagtgga cgaacctctg gtgtaccggt tgtcacgcca gtggcattgc cggg        54

<210> SEQ ID NO 33
<211> LENGTH: 54
<212> TYPE: DNA
<213> ORGANISM: Artificial sequence
<220> FEATURE:
<223> OTHER INFORMATION: Description of the artificial sequence:
      derived from species of the genus Vibrio

<400> SEQUENCE: 33
ccggagtgga cgaacctctg gtgttcgggt tgtgtcgcca gacgcattgc ccgg        54

<210> SEQ ID NO 34
<211> LENGTH: 41
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 34
gagataaccg ctgaaagcat ctaagcggga aacttgcctc g                      41

<210> SEQ ID NO 35
<211> LENGTH: 41
<212> TYPE: DNA
<213> ORGANISM: Artificial sequence
<220> FEATURE:
<223> OTHER INFORMATION: Description of the artificial sequence: derived
      from species of the genus Acinetobacter

<400> SEQUENCE: 35
gggataaccg ctgaaagcat ctaagcggga agcctacctc a                      41

<210> SEQ ID NO 36
<211> LENGTH: 41
<212> TYPE: DNA
<213> ORGANISM: Artificial sequence
<220> FEATURE:
<223> OTHER INFORMATION: Description of the artificial sequence: derived
      from species of the genus Aeromonas

<400> SEQUENCE: 36
tcgataaccg ctgaaagcat ctaagcggga agcgagccct g                      41

<210> SEQ ID NO 37
<211> LENGTH: 41
<212> TYPE: DNA
<213> ORGANISM: Artificial sequence
<220> FEATURE:
<223> OTHER INFORMATION: Description of the artificial sequence: derived from species of the genus Haemophilus

<400> SEQUENCE: 37
gagataagtg ctgaaagcat ctaagcacga aacttgccaa g          41

<210> SEQ ID NO 38
<211> LENGTH: 42
<212> TYPE: DNA
<213> ORGANISM: Artificial sequence
<220> FEATURE:
<223> OTHER INFORMATION: Description of the artificial sequence: derived
      from species of the genus Moraxella

<400> SEQUENCE: 38
gggataaccg ctgaaagcat ctaagcggga agcccacctt aa         42

<210> SEQ ID NO 39
<211> LENGTH: 42
<212> TYPE: DNA
<213> ORGANISM: Artificial sequence
<220> FEATURE:
<223> OTHER INFORMATION: Description of the artificial sequence: derived
      from species of the genus Pasteurella

<400> SEQUENCE: 39
gggataagtg ctgaaagcat ctaagcacga agcccccctc aa         42

<210> SEQ ID NO 40
<211> LENGTH: 42
<212> TYPE: DNA
<213> ORGANISM: Artificial sequence
<220> FEATURE:
<223> OTHER INFORMATION: Description of the artificial sequence:
      derived from species of the genus
      Stenotrophomonas

<400> SEQUENCE: 40
gagataaccg ctgaaagcat ctaagcggga aacttgcctt ga         42

<210> SEQ ID NO 41
<211> LENGTH: 42
<212> TYPE: DNA
<213> ORGANISM: Artificial sequence
<220> FEATURE:
<223> OTHER INFORMATION: Description of the artificial sequence:
      derived from species of the genus Vibrio

<400> SEQUENCE: 41
tcgataaccg ctgaaagcat ctaagcggga agcgagcctt ga         42

<210> SEQ ID NO 42
<211> LENGTH: 24
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 42
agatgagtct tccctgggcc ttta                             24

<210> SEQ ID NO 43
<211> LENGTH: 24
<212> TYPE: DNA
<213> ORGANISM: Artificial sequence
<220> FEATURE:
<223> OTHER INFORMATION: Description of the artificial sequence: derived -continued from species of the genus Acinetobacter

<400> SEQUENCE: 43
agataagatt tccctaggac ttta                                    24

<210> SEQ ID NO 44
<211> LENGTH: 24
<212> TYPE: DNA
<213> ORGANISM: Artificial sequence
<220> FEATURE:
<223> OTHER INFORMATION: Description of the artificial sequence: derived
      from species of the genus Aeromonas

<400> SEQUENCE: 44
agatgagtca tccctgaccc cttg                                    24

<210> SEQ ID NO 45
<211> LENGTH: 21
<212> TYPE: DNA
<213> ORGANISM: Artificial sequence
<220> FEATURE:
<223> OTHER INFORMATION: Description of the artificial sequence: derived
      from species of the genus Haemophilus

<400> SEQUENCE: 45
agatgagtca tccctgactt t                                       21

<210> SEQ ID NO 46
<211> LENGTH: 13
<212> TYPE: DNA
<213> ORGANISM: Artificial sequence
<220> FEATURE:
<223> OTHER INFORMATION: Description of the artificial sequence: derived
      from species of the genus Moraxella

<400> SEQUENCE: 46
agataagatt tcc                                                13

<210> SEQ ID NO 47
<211> LENGTH: 21
<212> TYPE: DNA
<213> ORGANISM: Artificial sequence
<220> FEATURE:
<223> OTHER INFORMATION: Description of the artificial sequence: derived
      from species of the genus Pasteurella

<400> SEQUENCE: 47
agatgagatt tcccattacg c                                       21

<210> SEQ ID NO 48
<211> LENGTH: 23
<212> TYPE: DNA
<213> ORGANISM: Artificial sequence
<220> FEATURE:
<223> OTHER INFORMATION: Description of the artificial sequence:
      derived from species of the genus
      Stenotrophomonas

<400> SEQUENCE: 48
agatgagatt tcccggagcc ttg                                     23

<210> SEQ ID NO 49
<211> LENGTH: 24
<212> TYPE: DNA
<213> ORGANISM: Vibrio alginolyticus

<400> SEQUENCE: 49

-continued

```
agatgagttc tccctgatac ttta                                          24

<210> SEQ ID NO 50
<211> LENGTH: 13
<212> TYPE: DNA
<213> ORGANISM: Vibrio fisheri

<400> SEQUENCE: 50
agattagatt tcc                                                      13

<210> SEQ ID NO 51
<211> LENGTH: 24
<212> TYPE: DNA
<213> ORGANISM: Vibrio harbeyi

<400> SEQUENCE: 51
agatgagtct tccctgggcc ttta                                          24

<210> SEQ ID NO 52
<211> LENGTH: 24
<212> TYPE: DNA
<213> ORGANISM: Vibrio parahaemolyticus

<400> SEQUENCE: 52
agatgagtct tccctgatac ttta                                          24

<210> SEQ ID NO 53
<211> LENGTH: 24
<212> TYPE: DNA
<213> ORGANISM: Vibrio proteolyticus

<400> SEQUENCE: 53
agatgagtct tccctggcac ttta                                          24

<210> SEQ ID NO 54
<211> LENGTH: 32
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 54
agggtcctga agggacgttg aagactacga cg                                 32

<210> SEQ ID NO 55
<211> LENGTH: 32
<212> TYPE: DNA
<213> ORGANISM: Artificial sequence
<220> FEATURE:
<223> OTHER INFORMATION: Description of the artificial sequence: derived
      from species of the genus Acinetobacter

<400> SEQUENCE: 55
tgtcctctaa agagccgttc gagactagga cg                                 32

<210> SEQ ID NO 56
<211> LENGTH: 32
<212> TYPE: DNA
<213> ORGANISM: Artificial sequence
<220> FEATURE:
<223> OTHER INFORMATION: Description of the artificial sequence: derived
      from species of the genus Aeromonas

<400> SEQUENCE: 56
```
tgtcctctaa agagccgttc gagactagga cg                                32

<210> SEQ ID NO 57
<211> LENGTH: 31
<212> TYPE: DNA
<213> ORGANISM: Artificial sequence
<220> FEATURE:
<223> OTHER INFORMATION: Description of the artificial sequence: derived
      from species of the genus Haemophilus

<400> SEQUENCE: 57
aagtcagtaa gggttgttgt agactacgac g                                 31

<210> SEQ ID NO 58
<211> LENGTH: 26
<212> TYPE: DNA
<213> ORGANISM: Artificial sequence
<220> FEATURE:
<223> OTHER INFORMATION: Description of the artificial sequence: derived
      from species of the genus Moraxella

<400> SEQUENCE: 58
ctaaagagcc gttgtagacg acgacg                                       26

<210> SEQ ID NO 59
<211> LENGTH: 31
<212> TYPE: DNA
<213> ORGANISM: Artificial sequence
<220> FEATURE:
<223> OTHER INFORMATION: Description of the artificial sequence: derived
      from species of the genus Pasteurella

<400> SEQUENCE: 59
aagtaagtaa gatccctcaa agacgatgag g                                 31

<210> SEQ ID NO 60
<211> LENGTH: 32
<212> TYPE: DNA
<213> ORGANISM: Artificial sequence
<220> FEATURE:
<223> OTHER INFORMATION: Description of the artificial sequence:
      derived from species of the genus
      Stenotrophomonas

<400> SEQUENCE: 60
agctccttga agggtcgttc gagaccagga cg                                32

<210> SEQ ID NO 61
<211> LENGTH: 32
<212> TYPE: DNA
<213> ORGANISM: Vibrio alginolyticus

<400> SEQUENCE: 61
agtatcctaa agggttgtcg tagmtacgac gt                                32

<210> SEQ ID NO 62
<211> LENGTH: 27
<212> TYPE: DNA
<213> ORGANISM: Vibrio fisheri

<400> SEQUENCE: 62
ctaaagagcc gttcaagact aggacgt                                      27

<210> SEQ ID NO 63
<211> LENGTH: 33

```
<212> TYPE: DNA
<213> ORGANISM: Vibrio harbeyi

<400> SEQUENCE: 63
agtatcctaa agggttgttc gagactagaa cgt                           33

<210> SEQ ID NO 64
<211> LENGTH: 33
<212> TYPE: DNA
<213> ORGANISM: Vibrio parahaemolyticus

<400> SEQUENCE: 64
agtatcctaa agggttgttc gagactagaa cgt                           33

<210> SEQ ID NO 65
<211> LENGTH: 33
<212> TYPE: DNA
<213> ORGANISM: Vibrio proteolyticus

<400> SEQUENCE: 65
agtgtcctga agggttgttc gagactagaa cgt                           33

<210> SEQ ID NO 66
<211> LENGTH: 40
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 66
agcgatgcgt tgagctaacc agtactaatg acccgtgagg                    40

<210> SEQ ID NO 67
<211> LENGTH: 40
<212> TYPE: DNA
<213> ORGANISM: Artificial sequence
<220> FEATURE:
<223> OTHER INFORMATION: Description of the artificial sequence: derived
      from species of the genus Acinetobacter

<400> SEQUENCE: 67
agtgatatgt gaagctgacc aatactaatt gctcgtgagg                    40

<210> SEQ ID NO 68
<211> LENGTH: 40
<212> TYPE: DNA
<213> ORGANISM: Artificial sequence
<220> FEATURE:
<223> OTHER INFORMATION: Description of the artificial sequence: derived
      from species of the genus Aeromonas

<400> SEQUENCE: 68
ggcgacgtgt tgagctaacc catactaatt acccgtgagg                    40

<210> SEQ ID NO 69
<211> LENGTH: 40
<212> TYPE: DNA
<213> ORGANISM: Artificial sequence
<220> FEATURE:
<223> OTHER INFORMATION: Description of the artificial sequence: derived
      from species of the genus Haemophilus

<400> SEQUENCE: 69
tgtgagtcat tgagctaacc aatactaatt gcccgagagg                    40
```

```
<210> SEQ ID NO 70
<211> LENGTH: 40
<212> TYPE: DNA
<213> ORGANISM: Artificial sequence
<220> FEATURE:
<223> OTHER INFORMATION: Description of the artificial sequence: derived
      from species of the genus Moraxella

<400> SEQUENCE: 70
agtgatacat gtagctaacc aatactaatt gctcgtttgg                          40

<210> SEQ ID NO 71
<211> LENGTH: 47
<212> TYPE: DNA
<213> ORGANISM: Pasteurella pneumotropica

<400> SEQUENCE: 71
tggcgacacg tgcagctgac gaatactaat cgatcgagga cttaacc                  47

<210> SEQ ID NO 72
<211> LENGTH: 40
<212> TYPE: DNA
<213> ORGANISM: Artificial sequence
<220> FEATURE:
<223> OTHER INFORMATION: Description of the artificial sequence:
      derived from species of the genus
      Stenotrophomonas

<400> SEQUENCE: 72
agtaatgcat taagctaacc agtactaatt gcccgtacgg                          40

<210> SEQ ID NO 73
<211> LENGTH: 40
<212> TYPE: DNA
<213> ORGANISM: Vibrio alginolyticus

<400> SEQUENCE: 73
tgtgaggcgt tgagctaacc tgtactaatt gcccgtgagg                          40

<210> SEQ ID NO 74
<211> LENGTH: 40
<212> TYPE: DNA
<213> ORGANISM: Vibrio fisheri

<400> SEQUENCE: 74
agtgatgcgt gtagctaacc tgtactaatt gctcgtttgg                          40

<210> SEQ ID NO 75
<211> LENGTH: 40
<212> TYPE: DNA
<213> ORGANISM: Vibrio harveyi

<400> SEQUENCE: 75
tgtgaggcgt tgagctaacc tgtactaatt gcccgtgagg                          40

<210> SEQ ID NO 76
<211> LENGTH: 40
<212> TYPE: DNA
<213> ORGANISM: Vibrio paramaemolyticus

<400> SEQUENCE: 76
tgtgaggcat tgagctaact gatactaatt gcccgtgagg                          40

<210> SEQ ID NO 77
```

-continued

```
<211> LENGTH: 40
<212> TYPE: DNA
<213> ORGANISM: Vibrio proteolyticus

<400> SEQUENCE: 77
tgtgaggcgt tgagctaacc tgtactaatt gcccgtgagg                              40

<210> SEQ ID NO 78
<211> LENGTH: 30
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 78
acccgtgagg cttaaccttta caacaccgaa                                       30

<210> SEQ ID NO 79
<211> LENGTH: 30
<212> TYPE: DNA
<213> ORGANISM: Artificial sequence
<220> FEATURE:
<223> OTHER INFORMATION: Description of the artificial sequence: derived
      from species of the genus Acinetobacter

<400> SEQUENCE: 79
gctcgtgagg cttgactata caacacccaa                                        30

<210> SEQ ID NO 80
<211> LENGTH: 30
<212> TYPE: DNA
<213> ORGANISM: Artificial sequence
<220> FEATURE:
<223> OTHER INFORMATION: Description of the artificial sequence: derived
      from species of the genus Aeromonas

<400> SEQUENCE: 80
acccgtgagg cttaaccata caacacccaa                                        30

<210> SEQ ID NO 81
<211> LENGTH: 30
<212> TYPE: DNA
<213> ORGANISM: Artificial sequence
<220> FEATURE:
<223> OTHER INFORMATION: Description of the artificial sequence: derived
      from species of the genus Haemophilus

<400> SEQUENCE: 81
gcccgagagg cttaactata caacgctcaa                                        30

<210> SEQ ID NO 82
<211> LENGTH: 30
<212> TYPE: DNA
<213> ORGANISM: Artificial sequence
<220> FEATURE:
<223> OTHER INFORMATION: Description of the artificial sequence: derived
      from species of the genus Moraxella

<400> SEQUENCE: 82
gctcgtttgg cttgaccata caacacccaa                                        30

<210> SEQ ID NO 83
<211> LENGTH: 33
<212> TYPE: DNA
<213> ORGANISM: Pasteurella pneumotropica
```

-continued

```
<400> SEQUENCE: 83
gctgacgaat actaatcgat cgaggactta acc                                33

<210> SEQ ID NO 84
<211> LENGTH: 30
<212> TYPE: DNA
<213> ORGANISM: Artificial sequence
<220> FEATURE:
<223> OTHER INFORMATION: Description of the artificial sequence: derived
      from species of the genus Stenotrophomonas

<400> SEQUENCE: 84
gcccgtacgg cttgtcccta taaccttggt                                    30

<210> SEQ ID NO 85
<211> LENGTH: 27
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 85
caacaccgaa ggtgttttgg aggaatc                                       27

<210> SEQ ID NO 86
<211> LENGTH: 27
<212> TYPE: DNA
<213> ORGANISM: Acinetobacter calcoaceticus

<400> SEQUENCE: 86
caacacccaa gcagttgtat ataaagc                                       27

<210> SEQ ID NO 87
<211> LENGTH: 27
<212> TYPE: DNA
<213> ORGANISM: Artificial sequence
<220> FEATURE:
<223> OTHER INFORMATION: Description of the artificial sequence: derived
      from species of the genus Aeromonas

<400> SEQUENCE: 87
caacacccaa gaagtgttct aaggctt                                       27

<210> SEQ ID NO 88
<211> LENGTH: 27
<212> TYPE: DNA
<213> ORGANISM: Haemophilus influenzae

<400> SEQUENCE: 88
caacgctcaa gtgttttttgg gagctaa                                      27

<210> SEQ ID NO 89
<211> LENGTH: 27
<212> TYPE: DNA
<213> ORGANISM: Moraxella catarrhalis

<400> SEQUENCE: 89
caacacccaa gtggtttacc actgact                                       27

<210> SEQ ID NO 90
<211> LENGTH: 27
<212> TYPE: DNA
<213> ORGANISM: Artificial sequence
<220> FEATURE:
```

```
<223> OTHER INFORMATION: Description of the artificial sequence:
      derived from species of the genus
      Stenotrophomonas

<400> SEQUENCE: 90
taaccttggt agtccaaggt cgagtac                                        27

<210> SEQ ID NO 91
<211> LENGTH: 27
<212> TYPE: DNA
<213> ORGANISM: Vibrio alginolyticus

<400> SEQUENCE: 91
caacacccaa ggggttttga tggactc                                        27

<210> SEQ ID NO 92
<211> LENGTH: 27
<212> TYPE: DNA
<213> ORGANISM: Vibrio fisheri

<400> SEQUENCE: 92 caacaccccaa gtggtttgta tcaagca                                       27

<210> SEQ ID NO 93
<211> LENGTH: 27
<212> TYPE: DNA
<213> ORGANISM: Vibrio harveyi

<400> SEQUENCE: 93
caacacccaa ggggttttga tggactc                                        27

<210> SEQ ID NO 94
<211> LENGTH: 27
<212> TYPE: DNA
<213> ORGANISM: Vibrio paramaemolyticus

<400> SEQUENCE: 94
caacacccaa ggggttttga tggactc                                        27

<210> SEQ ID NO 95
<211> LENGTH: 36
<212> TYPE: DNA
<213> ORGANISM: Vibrio proteolyticus

<400> SEQUENCE: 95
caacacccaa ggggttttga tggactcaat gaaaga                              36

<210> SEQ ID NO 96
<211> LENGTH: 118
<212> TYPE: DNA
<213> ORGANISM: Budvicia aquatica

<400> SEQUENCE: 96
caacatccga ggtgttttaa ggaaagttga agagacgaaa gaataagtag aattccagct    60
tgaaccgaga ttgagttgat ggttgtgtga atgacacgac ggtcaataga cagaatat    118

<210> SEQ ID NO 97
<211> LENGTH: 111
<212> TYPE: DNA
<213> ORGANISM: Buttiauxella agrestis

<400> SEQUENCE: 97
caacaccgaa ggtgttttgg ttgagagact aagatattga attttcagct tgaaccgaga    60
```

```
ttttaagtcg atggttgtgt gaacagcatg acggttgatg aaacagaata t          111
```

```
<210> SEQ ID NO 98
<211> LENGTH: 193
<212> TYPE: DNA
<213> ORGANISM: Enterobacter aglomerans

<400> SEQUENCE: 98
caacgccgaa gatgttttgg cggattgaga agattttcag cattgattac agattttcgg   60
gaacgaaaga ttttacgctg aggcaaggcg gcaaatgaag taaaggaagg agcatacatg  120
agtatgtgac tgactttgcg aatgcagcca acgcagccac agtgaaaaag attcgtttct  180
ggcaacagaa ttt                                                    193
```

```
<210> SEQ ID NO 99
<211> LENGTH: 123
<212> TYPE: DNA
<213> ORGANISM: Erwinia carotovora

<400> SEQUENCE: 99
caacaccgaa ggtgttttga gagtgactca aagagatgtt gataatcagc ttgttttagg   60
attggttctg atggttatgc gagagcgaaa gcgaagcatg acggttggga tgaaacagaa  120
ttt                                                                123
```

```
<210> SEQ ID NO 100
<211> LENGTH: 101
<212> TYPE: DNA
<213> ORGANISM: Erwinia chrysanthemi

<400> SEQUENCE: 100
caacaccgaa ggtgttttag agagattggt ttgaattttc agtgaagttc cgagattggt   60
tctgatggct acggagtagc ggtcgggatg aaacaaaatt t                      101
```

```
<210> SEQ ID NO 101
<211> LENGTH: 92
<212> TYPE: DNA
<213> ORGANISM: Escherichia coli

<400> SEQUENCE: 101
caacgccgaa gctgttttgg cggatgagag aagattttca gcctgataca gattaaatca   60
gaacgcagaa gcggtctgat aaaacagaat tt                                92
```

```
<210> SEQ ID NO 102
<211> LENGTH: 104
<212> TYPE: DNA
<213> ORGANISM: Escherichia hermannii

<400> SEQUENCE: 102
caacgccaga gtggttttgg tgttgcggtg tgagagacga ttttcagctt gaccggatag   60
acatctgtgg cggcgcgcga gcacgcagca ggtgaacaga attt                   104
```

```
<210> SEQ ID NO 103
<211> LENGTH: 92
<212> TYPE: DNA
<213> ORGANISM: Escherichia vulneris

<400> SEQUENCE: 103
caacgccgaa gatgttttgg cggatttgaa agacgatttt cagctgatac agattaagtc   60
```

```
tgccgcctga cggcgtcaga cagacagaat tt                                    92
```

<210> SEQ ID NO 104
<211> LENGTH: 119
<212> TYPE: DNA
<213> ORGANISM: Hafnia alvei

<400> SEQUENCE: 104

```
caacaccgaa ggtgttttaa gacgcagaga cgcgaaaaca caaagagtaa gcttgttgaa     60
cagattggtt tgtatggcta gctgtagaaa tacagaaagc ggtacaaata acagaatat    119
```

<210> SEQ ID NO 105
<211> LENGTH: 195
<212> TYPE: DNA
<213> ORGANISM: Klebsiella oxytoca

<400> SEQUENCE: 105

```
cgccgaagat gttttggcga tttgagaaga caacaatttc agcattgatt acagattttc     60
gggaacgaaa gattttacgc tgaggcaagg cggcaaatga aggaaaggaa ggagcatact    120
gaagtatgtg actgacttta cgaatgcagc caacgcagca tcggtgtaaa agattcgttt    180
ctgacaacag aattt                                                      195
```

<210> SEQ ID NO 106
<211> LENGTH: 90
<212> TYPE: DNA
<213> ORGANISM: Kluyvera cryoescens

<400> SEQUENCE: 106

```
cgccaaagat gttttggtga aaagagacat caataatcag cttgatacag ataaattaac     60
tggccgaaag gcgggttaat aacagaattt                                      90
```

<210> SEQ ID NO 107
<211> LENGTH: 105
<212> TYPE: DNA
<213> ORGANISM: Morganella morganii

<400> SEQUENCE: 107

```
caccgaaggt gttttgagtt gagagacgat taaagagatt tttcagcaca gtgaagaggc     60
agaagtcatt cactgtgaaa gcttattttg gattgaaatg aattt                    105
```

<210> SEQ ID NO 108
<211> LENGTH: 192
<212> TYPE: DNA
<213> ORGANISM: Pantoea dispersa
<220> FEATURE:
<221> NAME/KEY: misc_feature
<222> LOCATION: (61)..(61)
<223> OTHER INFORMATION: n = Adenosine (A) or Guanosine (G) or Cytosine
      (C) or Thymidine (T) or Inosine (I)
<220> FEATURE:
<221> NAME/KEY: misc_feature
<222> LOCATION: (29)..(29)
<223> OTHER INFORMATION: n = Adenosine (A) or Guanosine (G) or Cytosine
      (C) or Thymidine (T) or Inosine (I)
<220> FEATURE:
<221> NAME/KEY: misc_feature
<222> LOCATION: (179)..(179)
<223> OTHER INFORMATION: n = Adenosine (A) or Guanosine (G) or Cytosine
      (C) or Thymidine (T) or Inosine (I)

<400> SEQUENCE: 108

```
cgccagaggc gttttggtct gagagaccna aagaattttc agcattgttc accggattac     60
```

```
ntccagtgga ttttgtgctg tgacaaggcg gcacgcgaga cgacgggaag gagcatacac    120
gagtatgtga ctgagcggcg cgagcggggc aacgcagtca gagcgcaaaa gacgcggtnt    180
aaaacaaaat tt                                                        192
```

<210> SEQ ID NO 109
<211> LENGTH: 190
<212> TYPE: DNA
<213> ORGANISM: Artificial sequence
<220> FEATURE:
<223> OTHER INFORMATION: Description of the artificial sequence: derived
      from species of the genus Pantoea

<400> SEQUENCE: 109

```
cgccgaagat gttttggcgg aatgagaaga ttttcagcat tgattacaga ttttcgggaa     60
cgaaagattt tacgctgagg caaggcggca aatgaagtaa aggaaggagc atacatgagt    120
atgtgactga ctttkcggat gcagccaacg cagccacagt gaaaaagatt cgtttctggc    180
aacagaattt                                                           190
```

<210> SEQ ID NO 110
<211> LENGTH: 111
<212> TYPE: DNA
<213> ORGANISM: Proteus mirabilis
<220> FEATURE:
<221> NAME/KEY: misc_feature
<222> LOCATION: (65)..(65)
<223> OTHER INFORMATION: n = Adenosine (A) or Guanosine (G) or Cytosine
      (C) or Thymidine (T) or Inosine (I)

<400> SEQUENCE: 110

```
caacaccgaa agtgttttgt cagagagacg aaacgatgaa gtcagcttgt tcaanattga     60
attactggcg acttaccgaa aggaaagaag cgagtgatta aaaccgaatt t             111
```

<210> SEQ ID NO 111
<211> LENGTH: 139
<212> TYPE: DNA
<213> ORGANISM: Proteus rettgeri

<400> SEQUENCE: 111

```
caacaccgaa ggtgttttag agagatagag ttgttttcaa gaaagagtga gaagccaaaa     60
ggtgaaggac acgcagcttg tttgagattg aggttctggt ttagtgaaga aaaaactaaa    120
cgggaacaaa acagaattt                                                 139
```

<210> SEQ ID NO 112
<211> LENGTH: 137
<212> TYPE: DNA
<213> ORGANISM: Providencia stuartii

<400> SEQUENCE: 112

```
caacaccgaa ggtgttttag agagacgaag agacgaattg ttgaagcgca cgagatagag     60
tggtgcgaaa aaatcagctt gttcaagatt gcagttctgg tttgcggtgt agacgcgaac    120
gggaacgaac cgaattt                                                   137
```

<210> SEQ ID NO 113
<211> LENGTH: 135
<212> TYPE: DNA
<213> ORGANISM: Rahnella aquatilis

<400> SEQUENCE: 113

```
caacaccgaa ggtgttttg atttgagaga cagactcgag agagtagatt ttcagcgaat      60
```

```
tgttccggta ttggttcgta tggcggcgtg tgatgagaaa ttatgacacg acgcggtatg      120
aatgaaacag aattt                                                       135

<210> SEQ ID NO 114
<211> LENGTH: 100
<212> TYPE: DNA
<213> ORGANISM: Serratia ficaria

<400> SEQUENCE: 114
caacaccgaa ggtgttttag agagacgaat aattttcagc gaagttctta gattggttct       60
ggtggttacg cgagtaacgg ccaagaatga aacagaattt                            100

<210> SEQ ID NO 115
<211> LENGTH: 106
<212> TYPE: DNA
<213> ORGANISM: Serratia fonticola

<400> SEQUENCE: 115
caacacccaa ggtgttttga agagattgaa gtagattttc agcgaagttc cgagattggt       60
ttcaatggcg acacgagagt gaagcggttg aaatgaaaca gaattt                     106

<210> SEQ ID NO 116
<211> LENGTH: 97
<212> TYPE: DNA
<213> ORGANISM: Serratia marcescens

<400> SEQUENCE: 116
caacaccgaa ggtgttttta gagagatttt cagcgaagtt ccgagattgg ttctgatggc       60
gacacgaaag tgaagcggtt ggaatgaaac agaattt                                97

<210> SEQ ID NO 117
<211> LENGTH: 99
<212> TYPE: DNA
<213> ORGANISM: Serratia plymuthica

<400> SEQUENCE: 117
caacaccgaa ggtgttttag agagattaca gtagattttc agcgacgttc cgagattggt       60
ttcaatggcc caaaggcgg ttggaatgaa acagaattt                               99

<210> SEQ ID NO 118
<211> LENGTH: 100
<212> TYPE: DNA
<213> ORGANISM: Serratia proteamaculans
<220> FEATURE:
<221> NAME/KEY: misc_feature
<222> LOCATION: (95)..(95)
<223> OTHER INFORMATION: n = Adenosine (A) or Guanosine (G) or Cytosine
      (C) or Thymidine (T) or Inosine (I)

<400> SEQUENCE: 118
caacaccaaa ggtgttttag agagattgta gagattttca gcgagttccg agattggttt       60
caatggctgc gagagtagcg gttggaatga aacanaattt                            100

<210> SEQ ID NO 119
<211> LENGTH: 101
<212> TYPE: DNA
<213> ORGANISM: Serratia rubidea

<400> SEQUENCE: 119
caacaccgaa ggtgttttag agagattggt ttgaattttc agtgaagttc cgagattggt       60
```

-continued tctgatggct acggagtagc ggtcgggatg aaacagaatt t        101

<210> SEQ ID NO 120
<211> LENGTH: 116
<212> TYPE: DNA
<213> ORGANISM: Yersinia enterolytica

<400> SEQUENCE: 120
caacaccaaa ggtgttttgt atttgagaga tagatattga ttttcagcga atgttccgag    60
attgggctgg ctggctgtgt gaaagattgc atagcgggtt agtttagaca gaattt       116

<210> SEQ ID NO 121
<211> LENGTH: 104
<212> TYPE: DNA
<213> ORGANISM: Yersinia pseudotuberculosis

<400> SEQUENCE: 121
caacaccgaa gtcttgaatt gagagagatt ttcagcgtcg ttccgagatt ggattgactg   60
gcgtcacaag cgctgtttgt gtgcgggtta attaaaacag attt                    104

<210> SEQ ID NO 122
<211> LENGTH: 179
<212> TYPE: DNA
<213> ORGANISM: Acinetobacter calcoaceticus

<400> SEQUENCE: 122
caacacccaa gcagttgtat ataaagcatc aatcgattca ttaatatgca aagcaacttg   60
atttagttat acgcttagct aaaatgaaca aaatatagta agactcaatc agcccatctg  120
taaagatttg gaaaacgcat cggcaaccaa taagaccaat gcaagtatcc ataccagtt   179

<210> SEQ ID NO 123
<211> LENGTH: 118
<212> TYPE: DNA
<213> ORGANISM: Aeromonas enteropelogenes
<220> FEATURE:
<221> NAME/KEY: misc_feature
<222> LOCATION: (20)..(20)
<223> OTHER INFORMATION: n = Adenosine (A) or Guanosine (G) or Cytosine
      (C) or Thymidine (T) or Inosine (I)

<400> SEQUENCE: 123
caacacccaa gaagtgtttn tggtgcttgt agcgaatgaa cgaactacgc attcagtgat   60
aacgacaagc cacgagcaac atcgttattc acgtcagctt tccaagattg aagatttt   118

<210> SEQ ID NO 124
<211> LENGTH: 81
<212> TYPE: DNA
<213> ORGANISM: Aeromonas hydrophila

<400> SEQUENCE: 124
caacacccaa gaagtgttct aaggcttgta gcagataccg agaacgaaca acaaaatcag   60
ctttctcaga ttgaagaatt t                                              81

<210> SEQ ID NO 125
<211> LENGTH: 96
<212> TYPE: DNA
<213> ORGANISM: Cedecea davisae

<400> SEQUENCE: 125
caacaccaaa ggtgttttgc gagacgcaat tttaattttc agcgaagttc aggattagac   60

```
tgatggtcac aaagtgacgg tcagtaaaca gaattt                              96

<210> SEQ ID NO 126
<211> LENGTH: 217
<212> TYPE: DNA
<213> ORGANISM: Haemophilus influenzae

<400> SEQUENCE: 126
caacgctcaa gtgtttttgg gagctaagtg aagtaagaga tgaaaagcga agcaaataaa    60
agcagagcga aagagaagta aaagactaaa caaagaaaag taaatataga agacttaata   120
gaaagaaaat cggattcagc ttgtgaccaa taagaacgag tgaaggtag aggaaagact    180 gagtaacgag agataaaaga gacgagagat aaaagag                            217

<210> SEQ ID NO 127
<211> LENGTH: 90
<212> TYPE: DNA
<213> ORGANISM: Moraxella catarrhalis

<400> SEQUENCE: 127
caacacccaa gtggtttacc actgactgtg ttgattggta atatataaga tgaaccttaa    60
tcttgatttg gtaataaaca gactcataca                                    90

<210> SEQ ID NO 128
<211> LENGTH: 134
<212> TYPE: DNA
<213> ORGANISM: Pasteurella pneumotropica

<400> SEQUENCE: 128
cgaggactta accaaatttg tttatcgtaa caatgtcgtt tatccagttt tgaaagaata    60 aattttatt aaataactct tgcattattc tacagagttg ttataataaa acatgtcctt   120
caaaagtatt caag                                                    134

<210> SEQ ID NO 129
<211> LENGTH: 141
<212> TYPE: DNA
<213> ORGANISM: Stenotrophomonas multophila
<220> FEATURE:
<221> NAME/KEY: misc_feature
<222> LOCATION: (55)..(55)
<223> OTHER INFORMATION: n = Adenosine (A) or Guanosine (G) or Cytosine
      (C) or Thymidine (T) or Inosine (I)
<220> FEATURE:
<221> NAME/KEY: misc_feature
<222> LOCATION: (112)..(112)
<223> OTHER INFORMATION: n = Adenosine (A) or Guanosine (G) or Cytosine
      (C) or Thymidine (T) or Inosine (I)

<400> SEQUENCE: 129
taaccttggt agtccaaggt cgagtacaac tgctcgatac aaaagctaca acccnactta    60
cttcttccag attcatggcc acgctgaaca aagcgtaggg tgggcggctg tnccgcccac   120
gcgtaactca agcgtagcca g                                             141

<210> SEQ ID NO 130
<211> LENGTH: 100
<212> TYPE: DNA
<213> ORGANISM: Vibrio alginolyticus

<400> SEQUENCE: 130
caacacccaa ggggttttga tggactcaat gaaagaacat tgaatgtgta agaacgagaa    60
```
ttaaaaaaca gctttccaga ttaaagaatt tgcttggcga    100

<210> SEQ ID NO 131
<211> LENGTH: 122
<212> TYPE: DNA
<213> ORGANISM: Vibrio fisheri

<400> SEQUENCE: 131
caacacccaa gtggttttgta tcaagcatta tatcgatatc accgttatcc ttgattcagt    60
taggataagt gatacttaag tcattaagta aaacaaacac agactcatat ctaaccccct    120
tt    122

<210> SEQ ID NO 132
<211> LENGTH: 122
<212> TYPE: DNA
<213> ORGANISM: Vibrio harveyi

<400> SEQUENCE: 132
caacacccaa gtggttttgta tcaagcatta tatcgatatc accgttatcc ttgattcagt    60
taggataagt gatacttaag tcattaagta aaacaaacac agactcatat ctaaccccct    120
tt    122

<210> SEQ ID NO 133
<211> LENGTH: 89
<212> TYPE: DNA
<213> ORGANISM: Vibrio paramaemolyticus

<400> SEQUENCE: 133
caacacccaa ggggtttga tggactcgaa gcaagaacag aattgaatgt gtagagaaca    60
caaaaacagc tttccgaatt aaagaattt    89

<210> SEQ ID NO 134
<211> LENGTH: 169
<212> TYPE: DNA
<213> ORGANISM: Vibrio proteolyticus

<400> SEQUENCE: 134
caacacccaa ggggtttga tggactcaat gaaagaacat tgaatgtgta agaacgagaa    60
ttaaaaaaca gctttccgaa tttaggaatt gaatttatta acgacatcca tgtcgttaac    120
ccttcgggcc gcactgaagt gcgttaaatt ttgttccaga caaaatttt    169

<210> SEQ ID NO 135
<211> LENGTH: 33
<212> TYPE: DNA
<213> ORGANISM: Artificial sequence
<220> FEATURE:
<223> OTHER INFORMATION: Description of the artificial sequence: derived
      from genera of enterobacteria

<400> SEQUENCE: 135
gcctggcggc actagcgcgg tggtcccacc tga    33

<210> SEQ ID NO 136
<211> LENGTH: 33
<212> TYPE: DNA
<213> ORGANISM: Buttiauxella agrestis

<400> SEQUENCE: 136
gcctggcggc agtagcgcgg tggtcccacc tga    33

```
<210> SEQ ID NO 137
<211> LENGTH: 33
<212> TYPE: DNA
<213> ORGANISM: Enterobacter agglomerans

<400> SEQUENCE: 137
gcctggcggc tttagcgcgg tggtcccacc tga                           33

<210> SEQ ID NO 138
<211> LENGTH: 33
<212> TYPE: DNA
<213> ORGANISM: Erwinia carotovora

<400> SEQUENCE: 138
gcctggcggc gatagcgcgg tggtcccacc tga                           33

<210> SEQ ID NO 139
<211> LENGTH: 33
<212> TYPE: DNA
<213> ORGANISM: Erwinia chrysanthemi

<400> SEQUENCE: 139
gcctggcggc ggtagcgcgg tggtcccacc tga                           33

<210> SEQ ID NO 140
<211> LENGTH: 33
<212> TYPE: DNA
<213> ORGANISM: Escherichia coli

<400> SEQUENCE: 140
gcctggcggc agtagcgcgg tggtcccacc tga                           33

<210> SEQ ID NO 141
<211> LENGTH: 33
<212> TYPE: DNA
<213> ORGANISM: Escherichia hermannii

<400> SEQUENCE: 141
gcctggcggc aagagcgcgg tggtcccacc tga                           33

<210> SEQ ID NO 142
<211> LENGTH: 33
<212> TYPE: DNA
<213> ORGANISM: Escherichia vulneris

<400> SEQUENCE: 142
gcctggcggc actagcgcgg tggtcccacc tga                           33

<210> SEQ ID NO 143
<211> LENGTH: 33
<212> TYPE: DNA
<213> ORGANISM: Hafnia alvei

<400> SEQUENCE: 143
gcctggcggc gatagcgcgg tggtcccacc tga                           33

<210> SEQ ID NO 144
<211> LENGTH: 32
<212> TYPE: DNA
<213> ORGANISM: Klebsiella oxytoca

<400> SEQUENCE: 144
gcctggcggc actagcgcgg tggtccacct ga                            32
```

<210> SEQ ID NO 145
<211> LENGTH: 33
<212> TYPE: DNA
<213> ORGANISM: Kluyvera cryoescens

<400> SEQUENCE: 145
gcctggcggc aacagcgcgg tggtcccacc tga         33

<210> SEQ ID NO 146
<211> LENGTH: 33
<212> TYPE: DNA
<213> ORGANISM: Morganella morganii

<400> SEQUENCE: 146
gcctggcggc cgtagcgcgg tggtcccacc tga         33

<210> SEQ ID NO 147
<211> LENGTH: 31
<212> TYPE: DNA
<213> ORGANISM: Pantoea dispersa

<400> SEQUENCE: 147
gcctggcggc aacagccgcg gtggtcccac c           31

<210> SEQ ID NO 148
<211> LENGTH: 33
<212> TYPE: DNA
<213> ORGANISM: Proteus mirabilis

<400> SEQUENCE: 148
gcttggtggc catagcgcgg tggtcccacc tga         33

<210> SEQ ID NO 149
<211> LENGTH: 33
<212> TYPE: DNA
<213> ORGANISM: Artificial sequence
<220> FEATURE:
<223> OTHER INFORMATION: Description of the artificial sequence: derived
      from species of the genera Proteus, Providencia

<400> SEQUENCE: 149
gtctggcggc aatagcacgg tggtcccacc tga         33

<210> SEQ ID NO 150
<211> LENGTH: 33
<212> TYPE: DNA
<213> ORGANISM: Rahnella aquatilis

<400> SEQUENCE: 150
gcctggcggc agtagcgcgg tggtcccacc tga         33

<210> SEQ ID NO 151
<211> LENGTH: 33
<212> TYPE: DNA
<213> ORGANISM: Artificial sequence
<220> FEATURE:
<223> OTHER INFORMATION: Description of the artificial sequence: derived
      from species of the genus Serratia

<400> SEQUENCE: 151
gcctggcggc aatagcgcgg tggtcccacc tga         33

<210> SEQ ID NO 152

```
<211> LENGTH: 33
<212> TYPE: DNA
<213> ORGANISM: Yersinia enterolytica

<400> SEQUENCE: 152
gcctggcggc catagcgcgg tggacccacc tga                          33

<210> SEQ ID NO 153
<211> LENGTH: 33
<212> TYPE: DNA
<213> ORGANISM: Yersinia pseudotuberculosis

<400> SEQUENCE: 153
gtctggcggc catagcgcgg tggtcycacc tga                          33

<210> SEQ ID NO 154
<211> LENGTH: 51
<212> TYPE: DNA
<213> ORGANISM: Acinetobacter calcoaceticus

<400> SEQUENCE: 154
aagtatccat accagttgtg ctggcgacca tagcaagagt gaaccacctg a      51

<210> SEQ ID NO 155
<211> LENGTH: 33
<212> TYPE: DNA
<213> ORGANISM: Artificial sequence
<220> FEATURE:
<223> OTHER INFORMATION: Description of the artificial sequence: derived
      from species of the genus Aeromonas

<400> SEQUENCE: 155
gcctggcggc catagcgccg tggaaccacc tga                          33

<210> SEQ ID NO 156
<211> LENGTH: 51
<212> TYPE: DNA
<213> ORGANISM: Haemophilus influenzae

<400> SEQUENCE: 156
aaaagacgag ttatcaaaga attatcctgg cggcgatagt gcggtggacc c       51

<210> SEQ ID NO 157
<211> LENGTH: 54
<212> TYPE: DNA
<213> ORGANISM: Moraxella catarrhalis

<400> SEQUENCE: 157
acagcgttgt taatccttttt acgctgacga caatagcaag atggaaccac ctga  54

<210> SEQ ID NO 158
<211> LENGTH: 43
<212> TYPE: DNA
<213> ORGANISM: Pasteurella pneumotropica

<400> SEQUENCE: 158
tctagtgatg atggcgaaga ggtcacaccc gttcccatac cga               43

<210> SEQ ID NO 159
<211> LENGTH: 54
<212> TYPE: DNA
<213> ORGANISM: Stenotrophomonas multophila

<400> SEQUENCE: 159
```

```
acaagtcaaa gcctgatgac catagcaagt cggtcccacc ccttcccatc ccga          54
```

```
<210> SEQ ID NO 160
<211> LENGTH: 33
<212> TYPE: DNA
<213> ORGANISM: Vibrio alginolyticus

<400> SEQUENCE: 160
gcttggcgac catagcgttt tggacccacc tga                                 33

<210> SEQ ID NO 161
<211> LENGTH: 51
<212> TYPE: DNA
<213> ORGANISM: Vibrio fisheri

<400> SEQUENCE: 161
ctcatatcta acccccttng ctgacgacaa tagcacgatg gcaccacctg a             51

<210> SEQ ID NO 162
<211> LENGTH: 45
<212> TYPE: DNA
<213> ORGANISM: Vibrio harveyi

<400> SEQUENCE: 162
gcttggcgac catagcgatt tggacccacc tgacttccat tccga                    45

<210> SEQ ID NO 163
<211> LENGTH: 33
<212> TYPE: DNA
<213> ORGANISM: Vibrio proteolyticus

<400> SEQUENCE: 163
gcttggcgac catagcgttt tggacccacc tga                                 33

<210> SEQ ID NO 164
<211> LENGTH: 37
<212> TYPE: DNA
<213> ORGANISM: Artificial sequence
<220> FEATURE:
<223> OTHER INFORMATION: Description of the artificial sequence: derived
      from species of the genera Rahnella, Serratia,
      Yersinia

<400> SEQUENCE: 164
agattttcag cgaagttccg agattggttt caatggc                             37

<210> SEQ ID NO 165
<211> LENGTH: 21
<212> TYPE: DNA
<213> ORGANISM: Artificial sequence
<220> FEATURE:
<223> OTHER INFORMATION: Description of the artificial sequence: derived
      from species of the genera Enterobacter, Escherichia,
      Klebsiella, Pantoea
<220> FEATURE:
<221> NAME/KEY: misc_feature
<222> LOCATION: (14)..(16)
<223> OTHER INFORMATION: I = Inosine (I)

<400> SEQUENCE: 165
ggaaggagca tacnnnagtat                                                21

<210> SEQ ID NO 166
<211> LENGTH: 32
<212> TYPE: DNA
<213> ORGANISM: Budvicia aquatica
```

<400> SEQUENCE: 166
aggtccctga aggaacgttt gagactaaga cg        32

<210> SEQ ID NO 167
<211> LENGTH: 32
<212> TYPE: DNA
<213> ORGANISM: Buttiauxella agrestis

<400> SEQUENCE: 167
agggtcctga aggaacgttg aagactacga cg        32

<210> SEQ ID NO 168
<211> LENGTH: 32
<212> TYPE: DNA
<213> ORGANISM: Enterobacter agglomerans

<400> SEQUENCE: 168
aggacactaa aggaacgttg aagacgacga cg        32

<210> SEQ ID NO 169
<211> LENGTH: 32
<212> TYPE: DNA
<213> ORGANISM: Erwinia carotovora

<400> SEQUENCE: 169
atgcccctga agggccgttg aagactacga cg        32

<210> SEQ ID NO 170
<211> LENGTH: 32
<212> TYPE: DNA
<213> ORGANISM: Erwinia chrysanthemi

<400> SEQUENCE: 170
aggcccctga agggacgttt aagacgaaga cg        32

<210> SEQ ID NO 171
<211> LENGTH: 29
<212> TYPE: DNA
<213> ORGANISM: Escherichia coli

<400> SEQUENCE: 171
agggtcctga aggaacgttg aagacgacg        29

<210> SEQ ID NO 172
<211> LENGTH: 32
<212> TYPE: DNA
<213> ORGANISM: Escherichia hermannii

<400> SEQUENCE: 172
agagtcctga aggaacgttg aagacgacga cg        32

<210> SEQ ID NO 173
<211> LENGTH: 32
<212> TYPE: DNA
<213> ORGANISM: Escherichia vulneris

<400> SEQUENCE: 173
agtctcctga aggaacgttg aagacgacga cg        32

<210> SEQ ID NO 174
<211> LENGTH: 32
<212> TYPE: DNA

<213> ORGANISM: Hafnia alvei

<400> SEQUENCE: 174
agtctcctaa aggaacgttt aagactaaga cg                32

<210> SEQ ID NO 175
<211> LENGTH: 32
<212> TYPE: DNA
<213> ORGANISM: Artificial sequence
<220> FEATURE:
<223> OTHER INFORMATION: Description of the artificial sequence: derived
      from species of the genera Klebsiella, Kuyvera

<400> SEQUENCE: 175
agggtcctga aggaacgttg aagacgacga cg                32

<210> SEQ ID NO 176
<211> LENGTH: 32
<212> TYPE: DNA
<213> ORGANISM: Morganella morganii

<400> SEQUENCE: 176
agggtcctga aggaacgttt gagactaaga cg                32

<210> SEQ ID NO 177
<211> LENGTH: 32
<212> TYPE: DNA
<213> ORGANISM: Pantoea dispersa

<400> SEQUENCE: 177
agggtcctga agggacgctg aagacgacga cg                32

<210> SEQ ID NO 178
<211> LENGTH: 32
<212> TYPE: DNA
<213> ORGANISM: Artificial sequence
<220> FEATURE:
<223> OTHER INFORMATION: Description of the artificial sequence: derived
      from species of the genus Pantoea

<400> SEQUENCE: 178
aggacactaa aggaacgtta aagacgatga cg                32

<210> SEQ ID NO 179
<211> LENGTH: 32
<212> TYPE: DNA
<213> ORGANISM: Proteus mirabilis

<400> SEQUENCE: 179
agtgacctaa aggaacgttt aagactaaga cg                32

<210> SEQ ID NO 180
<211> LENGTH: 32
<212> TYPE: DNA
<213> ORGANISM: Proteus rettgeri

<400> SEQUENCE: 180
agggtcctaa aggaacgttt aagactaaga cg                32

<210> SEQ ID NO 181
<211> LENGTH: 32
<212> TYPE: DNA
<213> ORGANISM: Providencia stuartii

<400> SEQUENCE: 181

```
agggtcctaa aggaacgttt aagacgaaga cg                    32
```

<210> SEQ ID NO 182
<211> LENGTH: 32
<212> TYPE: DNA
<213> ORGANISM: Rahnella aquatilis

<400> SEQUENCE: 182

```
agccacctga agggacgttt aagactaaga cg                    32
```

<210> SEQ ID NO 183
<211> LENGTH: 32
<212> TYPE: DNA
<213> ORGANISM: Artificial sequence
<220> FEATURE:
<223> OTHER INFORMATION: Description of the artificial sequence: derived
      from species of the genus Serratia

<400> SEQUENCE: 183

```
aggcccctga aggaacgttt aagactaaga cg                    32
```

<210> SEQ ID NO 184
<211> LENGTH: 32
<212> TYPE: DNA
<213> ORGANISM: Yersinia enterolytica

<400> SEQUENCE: 184

```
agccccctga aggaacgtta aagactatga cg                    32
```

<210> SEQ ID NO 185
<211> LENGTH: 32
<212> TYPE: DNA
<213> ORGANISM: Yersinia pseudotuberculosis

<400> SEQUENCE: 185

```
agcccccctga gggaacgtta aagactatga cg                   32
```

<210> SEQ ID NO 186
<211> LENGTH: 32
<212> TYPE: DNA
<213> ORGANISM: Cedecea davisae

<400> SEQUENCE: 186

```
agaccccctga agggacgttg aagactacga cg                   32
```

<210> SEQ ID NO 187
<211> LENGTH: 24
<212> TYPE: DNA
<213> ORGANISM: Artificial sequence
<220> FEATURE:
<223> OTHER INFORMATION: Description of the artificial sequence: derived
      from species of the genera Buttiauxella, Escherichia,
      Klebsiella, Kluyvera, Pantoea

<400> SEQUENCE: 187

```
agatgagttc tccctgaccc ttta                             24
```

<210> SEQ ID NO 188
<211> LENGTH: 24
<212> TYPE: DNA
<213> ORGANISM: Artificial sequence
<220> FEATURE:
<223> OTHER INFORMATION: Description of the artificial sequence: derived
      from species of the genera Enterobacter, Pantoea -continued

```
<400> SEQUENCE: 188
agatgagttc tcccttgtcc ttta                                              24

<210> SEQ ID NO 189
<211> LENGTH: 24
<212> TYPE: DNA
<213> ORGANISM: Erwinia carotovora

<400> SEQUENCE: 189
agatgagtct tccctgggca ccag                                              24

<210> SEQ ID NO 190
<211> LENGTH: 24
<212> TYPE: DNA
<213> ORGANISM: Erwinia chrysanthemi

<400> SEQUENCE: 190
agatgagtct tccctgggcc cttg                                              24

<210> SEQ ID NO 191
<211> LENGTH: 24
<212> TYPE: DNA
<213> ORGANISM: Escherichia hermannii

<400> SEQUENCE: 191
agatgagttc tccctgactc cttg                                              24

<210> SEQ ID NO 192
<211> LENGTH: 24
<212> TYPE: DNA
<213> ORGANISM: Escherichia vulneris

<400> SEQUENCE: 192
agatgagttc tccctgagac ttta                                              24

<210> SEQ ID NO 193
<211> LENGTH: 24
<212> TYPE: DNA
<213> ORGANISM: Hafnia alvei

<400> SEQUENCE: 193
agatgagtct tccctgagac cttg                                              24

<210> SEQ ID NO 194
<211> LENGTH: 24
<212> TYPE: DNA
<213> ORGANISM: Morganella morganii

<400> SEQUENCE: 194
agatgagtct tccctgaccc ttta                                              24

<210> SEQ ID NO 195
<211> LENGTH: 24
<212> TYPE: DNA
<213> ORGANISM: Proteus mirabilis

<400> SEQUENCE: 195
agatgagtct tccctgtcac ttta                                              24

<210> SEQ ID NO 196
<211> LENGTH: 24
<212> TYPE: DNA
<213> ORGANISM: Proteus rettgeri
```

<400> SEQUENCE: 196
agatgagtct tccctgaccc ttta                                           24

<210> SEQ ID NO 197
<211> LENGTH: 24
<212> TYPE: DNA
<213> ORGANISM: Providencia stuartii

<400> SEQUENCE: 197
agatgagtct tccctgactc ttta                                           24

<210> SEQ ID NO 198
<211> LENGTH: 24
<212> TYPE: DNA
<213> ORGANISM: Rahnella aquatilis

<400> SEQUENCE: 198
agatgagtct tccctgtggc ttta                                           24

<210> SEQ ID NO 199
<211> LENGTH: 24
<212> TYPE: DNA
<213> ORGANISM: Yersinia enterolytica

<400> SEQUENCE: 199
agatgagtct tccctggggc ttta                                           24

<210> SEQ ID NO 200
<211> LENGTH: 24
<212> TYPE: DNA
<213> ORGANISM: Yersinia pseudotuberculosis

<400> SEQUENCE: 200
agatgagtct tccctggggc ttaa                                           24

<210> SEQ ID NO 201
<211> LENGTH: 24
<212> TYPE: DNA
<213> ORGANISM: Cedecea davisae

<400> SEQUENCE: 201
agatgaattc tccctgggtc cttg                                           24

<210> SEQ ID NO 202
<211> LENGTH: 199
<212> TYPE: DNA
<213> ORGANISM: Artificial sequence
<220> FEATURE:
<223> OTHER INFORMATION: Description of the artificial sequence: derived
      from species of the genus Citrobacter

<400> SEQUENCE: 202
caacgccgaa gatgttttgg cggaattgag agattttca gcattgattc agagtccgaa      60
ggattttgcg ctgagacaag gcggcawccc caccacggaa ggagcataca aaagtatgtg    120
actgaggttc gcaagcgcag ccaacgcagt atcagcacaa aagacacagg acagagcaca    180
aagaatttct ggcggccgt                                                 199

<210> SEQ ID NO 203
<211> LENGTH: 199
<212> TYPE: DNA
<213> ORGANISM: Artificial sequence

```
<220> FEATURE:
<223> OTHER INFORMATION: Description of the artificial sequence: derived
      from species of the genus Citrobacter

<400> SEQUENCE: 203
caacgccgaa gatgttttgg cggattgaga agattttcag tattgattac agattttgcg      60
aaaacgaaag attttacgct gaggcaaggc ggcaagtgaa cgacggaag kggcatacaa      120 aagtatgtga ctgaggttcg caggcgcagc caacgcagca tcagtggaaa agattcgttt    180
taagagcaca aagaatttc                                                   199

<210> SEQ ID NO 204
<211> LENGTH: 199
<212> TYPE: DNA
<213> ORGANISM: Artificial sequence
<220> FEATURE:
<223> OTHER INFORMATION: artificial sequence: derived
      from species of the genus Salmonella

<400> SEQUENCE: 204
caacsccsaa gatgttttgg csgatsagag argattttca gcactgattc ckgattttcg      60
vgaacgaaag attttacgct gaggcaaggc rgcaavcgaa ggaaaggaag gagcatactg    120
aagtatgtga ctgactttac gagcgcagcc aacgctagca tcsgtgtaaa agattcgttt    180
ctggcaacag aatttcctg                                                   199

<210> SEQ ID NO 205
<211> LENGTH: 201
<212> TYPE: DNA
<213> ORGANISM: derived from species of the genus Salmonella
<220> FEATURE:
<221> NAME/KEY: misc_feature
<222> LOCATION: (28)..(28)
<223> OTHER INFORMATION: n = Adenosine (A) or Guanosine (G) or Cytosine
      (C) or Thymidine (T) or Inosine (I)

<400> SEQUENCE: 205
caacgccgaa gctgttttgg cggatranaa sacgaacaat tttcagcact gattcagagt      60
tgagtacgca ataatttgcg cagcagcaag gcggcaagcg aaggaaagga aggagcatac    120
agaagtatgt gactgacttt acgagcgcag ccaacgccgc tgatgcgata aagaattgcg    180
tacagagcac aaaagaatat t                                                201

<210> SEQ ID NO 206
<211> LENGTH: 193
<212> TYPE: DNA
<213> ORGANISM: Artificial sequence
<220> FEATURE:
<223> OTHER INFORMATION: Description of the artificial sequence: derived
      from species of the genus Salmonella

<400> SEQUENCE: 206
caacgccgaa gatgttttgg csgttgagaa gacgattttc agcagtgatt ccgrgttgag      60
trcgcmrtaa tttkcgcmgc wgcarggcgg cargcgaagg arrggaggga gcatccwgaa    120
gtatktgact gagtttttcgr gcgcwggcam cgccgctgat gcgataaaga attgcgtach    180
gmgcacamag aat                                                          193

<210> SEQ ID NO 207
<211> LENGTH: 199
<212> TYPE: DNA
<213> ORGANISM: Artificial sequence
<220> FEATURE:
```

<223> OTHER INFORMATION: Description of the artificial sequence: derived
      from species of the genus Salmonella

<400> SEQUENCE: 207
caacgccgaa gatgttttgg cggattgaga gacgattttc agcactgatt ccggattttc      60
gggaacgaaa gattttacgc tgaggcaagg cggcaaatgr aggaaaggaa ggagcatact     120
gaagtatgtg actgactttt cgaatgcagc cgacgcagca tcggtgtaaa agattcgttt     180
ccggcaacag aattgtcct                                                  199

<210> SEQ ID NO 208
<211> LENGTH: 189
<212> TYPE: DNA
<213> ORGANISM: Artificial sequence
<220> FEATURE:
<223> OTHER INFORMATION: Description of the artificial sequence: derived
      from species of the genus Salmonella

<400> SEQUENCE: 208
caacgccgaa gatgttttgg cggatgagag acgattttca gcactgattc agagttgagt      60
acgcaataat ttgcgcagca gcaaggcggc aagcgaagga aaggaaggag catacagaag     120
tatgtgactg agtttacgag cgcaggcaac gccgctgatg cgataaagaa ttgcgtactg     180
agcataaaa                                                             189

<210> SEQ ID NO 209
<211> LENGTH: 196
<212> TYPE: DNA
<213> ORGANISM: Artificial sequence
<220> FEATURE:
<223> OTHER INFORMATION: Description of the artificial sequence: derived
      from species of the genus Salmonella

<400> SEQUENCE: 209
caacgccgaa gatgttttgg cggattgaga agacaacaat tttcagcyca gattcagagt      60
ccgaaggatt ttacgctgag acaaggcggc aaacgcagcs mcsgaaggas cmycacagaa     120
gtatgtgact gacgctcgca agagcagcca acgccgtatc agtgtaaaag acacaggacg     180
grgcacaaag aaattt                                                     196

<210> SEQ ID NO 210
<211> LENGTH: 77
<212> TYPE: DNA
<213> ORGANISM: Artificial sequence
<220> FEATURE:
<223> OTHER INFORMATION: artificial sequence: derived
      from species of the genus Salmonella

<400> SEQUENCE: 210
gagagacgat tttcagcact gattccggat tttcgggaac gaaagataaa agattcgttt      60
ccggcaacag aatttcc                                                     77

<210> SEQ ID NO 211
<211> LENGTH: 24
<212> TYPE: DNA
<213> ORGANISM: Artificial sequence
<220> FEATURE:
<223> OTHER INFORMATION: Description of the artificial sequence: derived
      from species and genera of eubacteria

<400> SEQUENCE: 211
ggtacgcgag ctgggtttag aacg                                             24

```
<210> SEQ ID NO 212
<211> LENGTH: 19
<212> TYPE: DNA
<213> ORGANISM: Artificial sequence
<220> FEATURE:
<223> OTHER INFORMATION: Description of the artificial sequence: derived
      from species and genera of eubacteria

<400> SEQUENCE: 212
gbgagagtag gdmayygcc                                                 19

<210> SEQ ID NO 213
<211> LENGTH: 54
<212> TYPE: DNA
<213> ORGANISM: Pseudomonas stutzeri

<400> SEQUENCE: 213
ccggagtgga cgaacctctg gtgttccggt tgtcacgcca gtggcattgc cggg          54

<210> SEQ ID NO 214
<211> LENGTH: 53
<212> TYPE: DNA
<213> ORGANISM: Thiobacilluc ferrooxidans

<400> SEQUENCE: 214
ccggagtgga cgtactctgg tgttccggtt gttctgccaa gggcattgcc ggg           53

<210> SEQ ID NO 215
<211> LENGTH: 54
<212> TYPE: DNA
<213> ORGANISM: Agrobacterium vitis

<400> SEQUENCE: 215
ccgggatgga catatctctg gtggacctgt tgtcgtgcca acggcatagc aggg          54

<210> SEQ ID NO 216
<211> LENGTH: 54
<212> TYPE: DNA
<213> ORGANISM: Adalia bipunctata

<400> SEQUENCE: 216
ccgaggtgga cgtacctctg gtggaccagt tgtcatgcca atggcacagc tggg          54

<210> SEQ ID NO 217
<211> LENGTH: 54
<212> TYPE: DNA
<213> ORGANISM: Amycolatopsis orientalis

<400> SEQUENCE: 217
ccgggacgga cgaacctctg gtgtgccagt tgtcctgcca agggcatggc tggt          54

<210> SEQ ID NO 218
<211> LENGTH: 54
<212> TYPE: DNA
<213> ORGANISM: Brucella ovis
<220> FEATURE:
<221> NAME/KEY: misc_feature
<222> LOCATION: (18)..(18)
<223> OTHER INFORMATION: n = Adenosine (A) or Guanosine (G) or Cytosine
      (C) or Thymidine (T) or Inosine (I)

<400> SEQUENCE: 218
ccgggatgga cgtatctntg gtggacctgt tgtggcgcca gccgcatagc aggg          54
```

<210> SEQ ID NO 219
<211> LENGTH: 54
<212> TYPE: DNA
<213> ORGANISM: Bradyrhizobium japonicum

<400> SEQUENCE: 219
ccggggtgaa cgtacctctg gtggagctgt tgtcgcgcca gcggcagtgc agca          54

<210> SEQ ID NO 220
<211> LENGTH: 54
<212> TYPE: DNA
<213> ORGANISM: Pseudomonas paucimobilis

<400> SEQUENCE: 220
ccgggatgga cgcaccgctg gtgtaccagt tgttctgcca agggcatcgc tggg          54

<210> SEQ ID NO 221
<211> LENGTH: 54
<212> TYPE: DNA
<213> ORGANISM: Rhodobacter sphaeroides

<400> SEQUENCE: 221
ccgggatgga cgcaccgctg gtgtaccagt tgttctgcca agggcatcgc tggg          54

<210> SEQ ID NO 222
<211> LENGTH: 57
<212> TYPE: DNA
<213> ORGANISM: Rickettsia prowazekii

<400> SEQUENCE: 222
ccgaggtgga cgtacccctg gtggaccagt tgtcgtgcca acggcaagct gggtagc       57

<210> SEQ ID NO 223
<211> LENGTH: 54
<212> TYPE: DNA
<213> ORGANISM: Sphingomonas paucimobilis

<400> SEQUENCE: 223
ccggagtgga cgaacctctg gtgtaccggt tgtcacgcca gtggcattgc cggg          54

<210> SEQ ID NO 224
<211> LENGTH: 54
<212> TYPE: DNA
<213> ORGANISM: Zymomonas mobilis

<400> SEQUENCE: 224
ccggggtgaa catgcctctg gtggacctgt cgtggcgcca gccgcgcagc aggg          54

<210> SEQ ID NO 225
<211> LENGTH: 54
<212> TYPE: DNA
<213> ORGANISM: Artificial sequence
<220> FEATURE:
<223> OTHER INFORMATION: Description of the artificial sequence: derived
      from species of the genus Alcaligenes

<400> SEQUENCE: 225
ccagagtgga cgaacctctg gtgtaccggt tgtgacgcca gtcgcatcgc cggg          54

<210> SEQ ID NO 226
<211> LENGTH: 53
<212> TYPE: DNA
<213> ORGANISM: Pseudomonas cepacia

<400> SEQUENCE: 226

```
ccgggacgac gaacctctgg tgtgtcagtt gtactgccaa gtgcaccgct gat          53

<210> SEQ ID NO 227
<211> LENGTH: 54
<212> TYPE: DNA
<213> ORGANISM: Ralstonia pickettii

<400> SEQUENCE: 227
ccggagtgga cgaacctctg gtgttccggt tgtcacgcca gtggcattgc cggg         54

<210> SEQ ID NO 228
<211> LENGTH: 54
<212> TYPE: DNA
<213> ORGANISM: Campylobacter jejuni

<400> SEQUENCE: 228
ccgggttgaa caaaccactg gtgtagctgt tgttctgcca agagcatcgc agcg         54

<210> SEQ ID NO 229
<211> LENGTH: 53
<212> TYPE: DNA
<213> ORGANISM: Helicobacter pylori

<400> SEQUENCE: 229
ccgggatgga cgtgtcactg gtgcaccagt tgtctgccaa gagcatcgct ggg          53

<210> SEQ ID NO 230
<211> LENGTH: 53
<212> TYPE: DNA
<213> ORGANISM: Actinoplanes utahensis

<400> SEQUENCE: 230
ccgggacgga cgaacctctg gtgtgccagt tgttctgcca agagcacggc tgg          53

<210> SEQ ID NO 231
<211> LENGTH: 54
<212> TYPE: DNA
<213> ORGANISM: Bacillus halodurans

<400> SEQUENCE: 231
ccgggatgga cacccgctg gtgtaccagt tgttccgcca ggagcatcgc tggg          54

<210> SEQ ID NO 232
<211> LENGTH: 54
<212> TYPE: DNA
<213> ORGANISM: Bacillus subtilis

<400> SEQUENCE: 232
ccgggatgga cgcaccgctg gtgtaccagt tgttctgcca agggcatcgc tggg         54

<210> SEQ ID NO 233
<211> LENGTH: 54
<212> TYPE: DNA
<213> ORGANISM: Clostridium tyrobutyricum

<400> SEQUENCE: 233
ccgggatgga ctgacctctg gtgtaccagt tgttccgcca ggagcatggc tggg         54

<210> SEQ ID NO 234
<211> LENGTH: 54
<212> TYPE: DNA
<213> ORGANISM: Artificial sequence
<220> FEATURE:
```

<223> OTHER INFORMATION: Description of the artificial sequence: derived
      from species of the genus Frankia

<400> SEQUENCE: 234
ccgggacgga cgaacctctg gtgtgccagt tgttctgcca agggcatggc tggt         54

<210> SEQ ID NO 235
<211> LENGTH: 54
<212> TYPE: DNA
<213> ORGANISM: Microbispora bispora

<400> SEQUENCE: 235
ccggaacgga cgaacctctg gtgtgccagt tgtgccgcca ggtgcacggc tggt         54

<210> SEQ ID NO 236
<211> LENGTH: 54
<212> TYPE: DNA
<213> ORGANISM: Mycobacterium leprae

<400> SEQUENCE: 236
ccgggacgga cgaacctctg gtataccagt tgtctcacca ggggcaccgc tgga         54

<210> SEQ ID NO 237
<211> LENGTH: 54
<212> TYPE: DNA
<213> ORGANISM: Mycobacterium smegmatis

<400> SEQUENCE: 237
ccgggacgga cgaacctctg gtataccagt tgtcccacca ggggcacggc tgga         54

<210> SEQ ID NO 238
<211> LENGTH: 54
<212> TYPE: DNA
<213> ORGANISM: Mycobacterium tuberculosis

<400> SEQUENCE: 238
ccgggacgga cgaacctctg gtgcaccagt tgtcccgcca ggggcaccgc tgga         54

<210> SEQ ID NO 239
<211> LENGTH: 54
<212> TYPE: DNA
<213> ORGANISM: Mycobacterium gallisepticum

<400> SEQUENCE: 239
ccggagtgaa gacacctctt gtgctccagt tgtagcgcca actgcaccgc tggg         54

<210> SEQ ID NO 240
<211> LENGTH: 58
<212> TYPE: DNA
<213> ORGANISM: Propionibacterium freudenreichii

<400> SEQUENCE: 240
ccgggacgga ccaacctctg gtgtgccagt tgttccacca ggagcatggc tggttggc    58

<210> SEQ ID NO 241
<211> LENGTH: 54
<212> TYPE: DNA
<213> ORGANISM: Rhodococcus erythropolis

<400> SEQUENCE: 241
ccgggacgga cgaacctctg gtgtgccagt tgttccgcca ggagcaccgc tgt          54

<210> SEQ ID NO 242

```
<211> LENGTH: 57
<212> TYPE: DNA
<213> ORGANISM: Rhodococcus fascians

<400> SEQUENCE: 242
ccgggacgac gaacctctgg tgtgccagtt gttccaccag gagcaccgct ggttggc        57

<210> SEQ ID NO 243
<211> LENGTH: 58
<212> TYPE: DNA
<213> ORGANISM: Staphylococcus aureus

<400> SEQUENCE: 243
ccgggatgga catacctctg gtgtaccagt tgtcgtgcca acggcatagc tgggtagc       58

<210> SEQ ID NO 244
<211> LENGTH: 54
<212> TYPE: DNA
<213> ORGANISM: Streptococcus faecalis
<220> FEATURE:
<221> NAME/KEY: misc_feature
<222> LOCATION: (14)..(14)
<223> OTHER INFORMATION: n = Adenosine (A) or Guanosine (G) or Cytosine
      (C) or Thymidine (T) or Inosine (I)

<400> SEQUENCE: 244
ccgggatgga cttnccgctg gtgtaccagt tgttctgcca agggcattgc tggg           54

<210> SEQ ID NO 245
<211> LENGTH: 54
<212> TYPE: DNA
<213> ORGANISM: Streptomyces ambifaciens
<220> FEATURE:
<221> NAME/KEY: misc_feature
<222> LOCATION: (14)..(14)
<223> OTHER INFORMATION: n = Adenosine (A) or Guanosine (G) or Cytosine
      (C) or Thymidine (T) or Inosine (I)

<400> SEQUENCE: 245
ccgggatgga cttnccgctg gtgtaccagt tgttctgcca agggcattgc tggg           54

<210> SEQ ID NO 246
<211> LENGTH: 54
<212> TYPE: DNA
<213> ORGANISM: Flavobacterium resinovorum

<400> SEQUENCE: 246
ccggagtgga cgtaccgctg gtgtacctgt tgtctcgcca gaggcatcgc aggg           54

<210> SEQ ID NO 247
<211> LENGTH: 54
<212> TYPE: DNA
<213> ORGANISM: Sphingobacterium multivorans
<220> FEATURE:
<221> NAME/KEY: misc_feature
<222> LOCATION: (34)..(34)
<223> OTHER INFORMATION: n = Adenosine (A) or Guanosine (G) or Cytosine
      (C) or Thymidine (T) or Inosine (I)

<400> SEQUENCE: 247
ccgggttgga cagacctctg gtgaacctgt catnccgcca ggtgtacggc aggg           54

<210> SEQ ID NO 248
<211> LENGTH: 54
<212> TYPE: DNA
<213> ORGANISM: Artificial sequence
<220> FEATURE:
```

```
<223> OTHER INFORMATION: Description of the artificial sequence: derived
      from species of the genus Synechococcus

<400> SEQUENCE: 248
ccggaggaac gcaccgctgg tgtaccagtt atcgtgccaa cggtaaacgc tggg              54

<210> SEQ ID NO 249
<211> LENGTH: 55
<212> TYPE: DNA
<213> ORGANISM: Artificial sequence
<220> FEATURE:
<223> OTHER INFORMATION: Description of the artificial sequence: derived
      from species of the genus Synechocystis

<400> SEQUENCE: 249
ccgggaagta cgcacctctg gtgtacctgt tatcgtgcca acggtaaacg caggg             55

<210> SEQ ID NO 250
<211> LENGTH: 59
<212> TYPE: DNA
<213> ORGANISM: Borrelia burgdorferi

<400> SEQUENCE: 250
ccgagatgga cgaacctcta gtgtaccagt tatcctgcca agggtaagtg ctgggtagc         59

<210> SEQ ID NO 251
<211> LENGTH: 58
<212> TYPE: DNA
<213> ORGANISM: Chlamydia trachomatis

<400> SEQUENCE: 251
ccggaatgga cgaaccaatg gtgtgtcggt tgttttgcca agggcatagc cgagtagc          58

<210> SEQ ID NO 252
<211> LENGTH: 42
<212> TYPE: DNA
<213> ORGANISM: Pseudomonas stutzeri

<400> SEQUENCE: 252
gagataaccg ctgaaagcat ctaagcggga aacttgcctc aa                          42

<210> SEQ ID NO 253
<211> LENGTH: 41
<212> TYPE: DNA
<213> ORGANISM: Thiobacilluc ferrooxidans

<400> SEQUENCE: 253
gggataaccg ctgaaagcat ctaagcggaa gccatcctaa g                           41

<210> SEQ ID NO 254
<211> LENGTH: 41
<212> TYPE: DNA
<213> ORGANISM: Agrobacterium vitis

<400> SEQUENCE: 254
tggataaccg ctgaaggcat ctaagcggga aaccaacctg a                           41

<210> SEQ ID NO 255
<211> LENGTH: 41
<212> TYPE: DNA
<213> ORGANISM: Adalia bipunctata

<400> SEQUENCE: 255
gggataaccg ctgaatgcat ctaagcagga aactcacctc a                           41
```

<210> SEQ ID NO 256
<211> LENGTH: 41
<212> TYPE: DNA
<213> ORGANISM: Amycolatopsis orientalis

<400> SEQUENCE: 256
aggataaccg ctgaaagcat ctaagcggga agcctgcttc g                41

<210> SEQ ID NO 257
<211> LENGTH: 42
<212> TYPE: DNA
<213> ORGANISM: Brucella ovis
<220> FEATURE:
<221> NAME/KEY: misc_feature
<222> LOCATION: (21)..(21)
<223> OTHER INFORMATION: n = Adenosine (A) or Guanosine (G) or Cytosine
      (C) or Thymidine (T) or Inosine (I)

<400> SEQUENCE: 257
gggataaccg ctgaaggcat ntaagcggga aacccacctg aa               42

<210> SEQ ID NO 258
<211> LENGTH: 41
<212> TYPE: DNA
<213> ORGANISM: Bradyrhizobium japonicum

<400> SEQUENCE: 258
gggataaccg ctgaaagcat ctaagcggga aacccacctc a                41

<210> SEQ ID NO 259
<211> LENGTH: 41
<212> TYPE: DNA
<213> ORGANISM: Pseudomonas paucimobilis

<400> SEQUENCE: 259
gggataagtg ctgaaagcat ctaagcatga agccccccctc a               41

<210> SEQ ID NO 260
<211> LENGTH: 41
<212> TYPE: DNA
<213> ORGANISM: Rhodobacter sphaeroides

<400> SEQUENCE: 260
aggataaccg ctgaaggcat ctaagcggga agccccttc a                 41

<210> SEQ ID NO 261
<211> LENGTH: 40
<212> TYPE: DNA
<213> ORGANISM: Rickettsia prowazekii

<400> SEQUENCE: 261
gggataactg ctgaatgcat ctaagcagga aacccacctc                  40

<210> SEQ ID NO 262
<211> LENGTH: 41
<212> TYPE: DNA
<213> ORGANISM: Sphingomonas paucimobilis

<400> SEQUENCE: 262
gagataaccg ctgaaagcat ctaagcggga aacttgcctt g                41

<210> SEQ ID NO 263
<211> LENGTH: 41

```
<212> TYPE: DNA
<213> ORGANISM: Zymomonas mobilis

<400> SEQUENCE: 263
gggataaccg ctgaaagcat ctaagcggga agcctccctc a                              41

<210> SEQ ID NO 264
<211> LENGTH: 41
<212> TYPE: DNA
<213> ORGANISM: Artificial sequence
<220> FEATURE:
<223> OTHER INFORMATION: Description of the artificial sequence: derived
      from species of the genus Alcaligenes

<400> SEQUENCE: 264
gggataaccg ctgaaagcat ctaagcggga agcctacctc a                              41

<210> SEQ ID NO 265
<211> LENGTH: 41
<212> TYPE: DNA
<213> ORGANISM: Pseudomonas cepacia

<400> SEQUENCE: 265
gggataaccg ctgaaagcat ctaagcggga agctcgcttc a                              41

<210> SEQ ID NO 266
<211> LENGTH: 41
<212> TYPE: DNA
<213> ORGANISM: Ralstonia pickettii

<400> SEQUENCE: 266
gagataaccg ctgaaagcat ctaagcggaa aacttgcctc a                              41

<210> SEQ ID NO 267
<211> LENGTH: 41
<212> TYPE: DNA
<213> ORGANISM: Campylobacter jejuni

<400> SEQUENCE: 267
aggataaacg ctgaaagcat ctaagcgtga agccaactct a                              41

<210> SEQ ID NO 268
<211> LENGTH: 42
<212> TYPE: DNA
<213> ORGANISM: Helicobacter pylori

<400> SEQUENCE: 268
tgtgataact gctgaaagca tctaagcagg aaccaactcc aa                             42

<210> SEQ ID NO 269
<211> LENGTH: 41
<212> TYPE: DNA
<213> ORGANISM: Actinoplanes utahensis

<400> SEQUENCE: 269
gggataaccg ctgaaagcat ctaagcggga agctcgcttc g                              41

<210> SEQ ID NO 270
<211> LENGTH: 41
<212> TYPE: DNA
<213> ORGANISM: Bacillus halodurans

<400> SEQUENCE: 270
gggataagtg ctgaaagcat ctaagcatga agccccctc a                               41
```

<210> SEQ ID NO 271
<211> LENGTH: 40
<212> TYPE: DNA
<213> ORGANISM: Clostridium tyrobutyricum

<400> SEQUENCE: 271
gggataaacg ctgaaagcat ctaagcgtga agcccacctc 40

<210> SEQ ID NO 272
<211> LENGTH: 41
<212> TYPE: DNA
<213> ORGANISM: Artificial sequence
<220> FEATURE:
<223> OTHER INFORMATION: Description of the artificial sequence: derived from species of the genus Frankia

<400> SEQUENCE: 272
gggataaccg ctgaaagcat ctaagcggga agcctgcttc g 41

<210> SEQ ID NO 273
<211> LENGTH: 41
<212> TYPE: DNA
<213> ORGANISM: Microbispora bispora

<400> SEQUENCE: 273
gggataaccg ctgaaagcat ctaagcggga agcccgcccc g 41

<210> SEQ ID NO 274
<211> LENGTH: 41
<212> TYPE: DNA
<213> ORGANISM: Mycobacterium leprae

<400> SEQUENCE: 274
aagataaccg ctgaaagcat ctaagcggga aaccttctcc a 41

<210> SEQ ID NO 275
<211> LENGTH: 41
<212> TYPE: DNA
<213> ORGANISM: Mycobacterium smegmatis

<400> SEQUENCE: 275
aggataaccg ctgaaagcat ctaagcggga aacctcttcc a 41

<210> SEQ ID NO 276
<211> LENGTH: 41
<212> TYPE: DNA
<213> ORGANISM: Mycobacterium tuberculosis

<400> SEQUENCE: 276
aggataaccg ctgaaagcat ctaagcggga aaccttctcc a 41

<210> SEQ ID NO 277
<211> LENGTH: 41
<212> TYPE: DNA
<213> ORGANISM: Mycobacterium gallisepticum

<400> SEQUENCE: 277
cggataaacg ctgaaagcat ctaagtgtga aaccgacttt a 41

<210> SEQ ID NO 278
<211> LENGTH: 43
<212> TYPE: DNA
<213> ORGANISM: Propionibacterium freudenreichii

<400> SEQUENCE: 278
agtgataacc gctgaaagca tctaagtggg aagcacgctt caa       43

<210> SEQ ID NO 279
<211> LENGTH: 41
<212> TYPE: DNA
<213> ORGANISM: Rhodococcus erythropolis

<400> SEQUENCE: 279
gggataaccg ctgaaagcat ctaagcggga agcctgttcc a         41

<210> SEQ ID NO 280
<211> LENGTH: 41
<212> TYPE: DNA
<213> ORGANISM: Staphylococcus aureus

<400> SEQUENCE: 280
gggataagtg ctgaaagcat ctaagcatga agccccctc a          41

<210> SEQ ID NO 281
<211> LENGTH: 41
<212> TYPE: DNA
<213> ORGANISM: Streptococcus faecalis
<220> FEATURE:
<221> NAME/KEY: misc_feature
<222> LOCATION: (36)..(36)
<223> OTHER INFORMATION: n = Adenosine (A) or Guanosine (G) or Cytosine
      (C) or Thymidine (T) or Inosine (I)

<400> SEQUENCE: 281
gggataaacg ctgaaagcat ctaagtgtga agcccncctc a         41

<210> SEQ ID NO 282
<211> LENGTH: 41
<212> TYPE: DNA
<213> ORGANISM: Streptomyces ambifaciens

<400> SEQUENCE: 282
gggataaccg ctgaaagcat ctaagcggga agcctgcttc g         41

<210> SEQ ID NO 283
<211> LENGTH: 41
<212> TYPE: DNA
<213> ORGANISM: Flavobacterium resinovorum

<400> SEQUENCE: 283
gagataaccg ctgaaagcat ctaagcggga aactcgcctg a         41

<210> SEQ ID NO 284
<211> LENGTH: 41
<212> TYPE: DNA
<213> ORGANISM: Sphingobacterium multivorans

<400> SEQUENCE: 284
tagataagcg ctgaaagcat ctaagtgcga aactagccac g         41

<210> SEQ ID NO 285
<211> LENGTH: 43
<212> TYPE: DNA
<213> ORGANISM: Artificial sequence
<220> FEATURE:
<223> OTHER INFORMATION: Description of the artificial sequence: derived
      from species of the genus Synechococcus

```
<400> SEQUENCE: 285
gtggataacc gctgaaagca tctaagtggg aagcccacct caa          43

<210> SEQ ID NO 286
<211> LENGTH: 43
<212> TYPE: DNA
<213> ORGANISM: Artificial sequence
<220> FEATURE:
<223> OTHER INFORMATION: Description of the artificial sequence: derived
      from species of the genus Synechocystis

<400> SEQUENCE: 286
gtggataacc gctgaaagca tctaagtggg aagcccacct caa          43

<210> SEQ ID NO 287
<211> LENGTH: 41
<212> TYPE: DNA
<213> ORGANISM: Borrelia burgdorferi

<400> SEQUENCE: 287
aggataaccg ctgaaagcat ctaagtggga agccttcctc a            41

<210> SEQ ID NO 288
<211> LENGTH: 41
<212> TYPE: DNA
<213> ORGANISM: Chlamydia trachomatis

<400> SEQUENCE: 288
aggataagca ttgaaagcat ctaaatgcca agcctccctc a            41

<210> SEQ ID NO 289
<211> LENGTH: 24
<212> TYPE: DNA
<213> ORGANISM: Pseudomonas stutzeri

<400> SEQUENCE: 289
agatgagatc tcactggagc cttg                               24

<210> SEQ ID NO 290
<211> LENGTH: 19
<212> TYPE: DNA
<213> ORGANISM: Thiobacillus ferrooxidans

<400> SEQUENCE: 290
atgagatctc ccgggcata                                     19

<210> SEQ ID NO 291
<211> LENGTH: 18
<212> TYPE: DNA
<213> ORGANISM: Agrobacterium vitis

<400> SEQUENCE: 291
aaacgagtat tccctatc                                      18

<210> SEQ ID NO 292
<211> LENGTH: 18
<212> TYPE: DNA
<213> ORGANISM: Adalia bipunctata

<400> SEQUENCE: 292
aaactagact tccccatc                                      18

<210> SEQ ID NO 293
```

-continued

```
<211> LENGTH: 23
<212> TYPE: DNA
<213> ORGANISM: Amycolatopsis orientalis

<400> SEQUENCE: 293
agatgagggc tcccacctcc ttg                                              23

<210> SEQ ID NO 294
<211> LENGTH: 18
<212> TYPE: DNA
<213> ORGANISM: Brucella ovis

<400> SEQUENCE: 294
aaacgagtat tccctatc                                                    18

<210> SEQ ID NO 295
<211> LENGTH: 17
<212> TYPE: DNA
<213> ORGANISM: Bradyrhizobium japonicum

<400> SEQUENCE: 295
aaacgagcat tcccttg                                                     17

<210> SEQ ID NO 296
<211> LENGTH: 22
<212> TYPE: DNA
<213> ORGANISM: Pseudomonas paucimobilis

<400> SEQUENCE: 296
agatgagatt tcccattccg ca                                               22

<210> SEQ ID NO 297
<211> LENGTH: 22
<212> TYPE: DNA
<213> ORGANISM: Rhodobacter sphaeroides

<400> SEQUENCE: 297
agatgagatt tcccattccg ca                                               22

<210> SEQ ID NO 298
<211> LENGTH: 18
<212> TYPE: DNA
<213> ORGANISM: Rickettsia prowazekii

<400> SEQUENCE: 298
aaactagact tccccatt                                                    18

<210> SEQ ID NO 299
<211> LENGTH: 23
<212> TYPE: DNA
<213> ORGANISM: Sphingomonas paucimobilis

<400> SEQUENCE: 299
agatgagatt tcccggagcc ttg                                              23

<210> SEQ ID NO 300
<211> LENGTH: 14
<212> TYPE: DNA
<213> ORGANISM: Zymomonas mobilis

<400> SEQUENCE: 300
agataagata tctc                                                        14
```

<210> SEQ ID NO 301
<211> LENGTH: 24
<212> TYPE: DNA
<213> ORGANISM: Artificial sequence
<220> FEATURE:
<223> OTHER INFORMATION: Description of the artificial sequence: derived
      from species of the genus Alcaligenes

<400> SEQUENCE: 301
agataagatt tccctaggac ttta                                          24

<210> SEQ ID NO 302
<211> LENGTH: 23
<212> TYPE: DNA
<213> ORGANISM: Pseudomonas cepacia

<400> SEQUENCE: 302
agatgagatt tccatacacc ttg                                           23

<210> SEQ ID NO 303
<211> LENGTH: 24
<212> TYPE: DNA
<213> ORGANISM: Ralstonia pickettii

<400> SEQUENCE: 303
agatgagatc tcactggaac cttg                                          24

<210> SEQ ID NO 304
<211> LENGTH: 24
<212> TYPE: DNA
<213> ORGANISM: Campylobacter jejuni

<400> SEQUENCE: 304
agatgaatct tctctaagct ctct                                          24

<210> SEQ ID NO 305
<211> LENGTH: 13
<212> TYPE: DNA
<213> ORGANISM: Helicobacter pylori

<400> SEQUENCE: 305
gataaacttt ccc                                                      13

<210> SEQ ID NO 306
<211> LENGTH: 23
<212> TYPE: DNA
<213> ORGANISM: Actinoplanes utahensis

<400> SEQUENCE: 306
agatgaggta tcccaccacc ttg                                           23

<210> SEQ ID NO 307
<211> LENGTH: 22
<212> TYPE: DNA
<213> ORGANISM: Bacillus halodurans

<400> SEQUENCE: 307
agatgagatt tcccatggag ta                                            22

<210> SEQ ID NO 308
<211> LENGTH: 22
<212> TYPE: DNA
<213> ORGANISM: Clostridium tyrobutyricum

<400> SEQUENCE: 308
agattagatt tcccacagcg ta                      22

<210> SEQ ID NO 309
<211> LENGTH: 23
<212> TYPE: DNA
<213> ORGANISM: Artificial sequence
<220> FEATURE:
<223> OTHER INFORMATION: Description of the artificial sequence: derived
      from species of the genus Frankia

<400> SEQUENCE: 309
agatgaggtc tcccacaggg tag                     23

<210> SEQ ID NO 310
<211> LENGTH: 23
<212> TYPE: DNA
<213> ORGANISM: Microbispora bispora

<400> SEQUENCE: 310
agatgaggtc tccctccggg tta                     23

<210> SEQ ID NO 311
<211> LENGTH: 22
<212> TYPE: DNA
<213> ORGANISM: Mycobacterium leprae

<400> SEQUENCE: 311
agatcaggtt tcttacccac tt                      22

<210> SEQ ID NO 312
<211> LENGTH: 22
<212> TYPE: DNA
<213> ORGANISM: Mycobacterium smegmatis

<400> SEQUENCE: 312
agaccaggct tctcaccctc ta                      22

<210> SEQ ID NO 313
<211> LENGTH: 22
<212> TYPE: DNA
<213> ORGANISM: Mycobacterium tuberculosis

<400> SEQUENCE: 313
agatcaggtt tctcacccac tt                      22

<210> SEQ ID NO 314
<211> LENGTH: 30
<212> TYPE: DNA
<213> ORGANISM: Mycobacterium gallisepticum

<400> SEQUENCE: 314
agaataatct tcccttccag caatggagta              30

<210> SEQ ID NO 315
<211> LENGTH: 21
<212> TYPE: DNA
<213> ORGANISM: Propionibacterium freudenreichii

<400> SEQUENCE: 315
gatgagggtt cctgcacagt t                       21

<210> SEQ ID NO 316
<211> LENGTH: 22

```
<212> TYPE: DNA
<213> ORGANISM: Rhodococcus erythropolis

<400> SEQUENCE: 316
agatgaggtt tctcacccccc tc                                              22

<210> SEQ ID NO 317
<211> LENGTH: 20
<212> TYPE: DNA
<213> ORGANISM: Staphylococcus aureus

<400> SEQUENCE: 317
agatgagatt tcccaacttc                                                  20

<210> SEQ ID NO 318
<211> LENGTH: 22
<212> TYPE: DNA
<213> ORGANISM: Streptococcus faecalis

<400> SEQUENCE: 318
agatgagatt tcccatttct tt                                               22

<210> SEQ ID NO 319
<211> LENGTH: 23
<212> TYPE: DNA
<213> ORGANISM: Streptomyces ambifaciens

<400> SEQUENCE: 319
agatgaggac tcccaccccc ttg                                              23

<210> SEQ ID NO 320
<211> LENGTH: 24
<212> TYPE: DNA
<213> ORGANISM: Flavobacterium resinovorum

<400> SEQUENCE: 320
agatgaggat tccctggcgg cttg                                             24

<210> SEQ ID NO 321
<211> LENGTH: 17
<212> TYPE: DNA
<213> ORGANISM: Sphingobacterium multivorans

<400> SEQUENCE: 321
agatgagact tccttat                                                     17

<210> SEQ ID NO 322
<211> LENGTH: 20
<212> TYPE: DNA
<213> ORGANISM: Artificial sequence
<220> FEATURE:
<223> OTHER INFORMATION: Description of the artificial sequence: derived
      from species of the genus Synechococcus

<400> SEQUENCE: 322
gatgagtact ctcatggcat                                                  20

<210> SEQ ID NO 323
<211> LENGTH: 21
<212> TYPE: DNA
<213> ORGANISM: Artificial sequence
<220> FEATURE:
<223> OTHER INFORMATION: Description of the artificial sequence: derived
      from species of the genus Synechocystis
```

```
<400> SEQUENCE: 323
gatgagtact ctcatggtgt t                                      21

<210> SEQ ID NO 324
<211> LENGTH: 16
<212> TYPE: DNA
<213> ORGANISM: Borrelia burgdorferi

<400> SEQUENCE: 324
agatgagata tcctttt                                           16

<210> SEQ ID NO 325
<211> LENGTH: 14
<212> TYPE: DNA
<213> ORGANISM: Chlamydia trachomatis

<400> SEQUENCE: 325
agataaggta tccc                                              14

<210> SEQ ID NO 326
<211> LENGTH: 32
<212> TYPE: DNA
<213> ORGANISM: Pseudomonas stutzeri

<400> SEQUENCE: 326
agctccctga agggccgtcg aagactacga cg                          32

<210> SEQ ID NO 327
<211> LENGTH: 32
<212> TYPE: DNA
<213> ORGANISM: Thiobacillus ferrooxidans

<400> SEQUENCE: 327
agccccctga agggacgtgg aagactacca cg                          32

<210> SEQ ID NO 328
<211> LENGTH: 22
<212> TYPE: DNA
<213> ORGANISM: Agrobacterium vitis

<400> SEQUENCE: 328
agagccgtgg aagacgacca cg                                     22

<210> SEQ ID NO 329
<211> LENGTH: 22
<212> TYPE: DNA
<213> ORGANISM: Adalia bipunctata

<400> SEQUENCE: 329
agagccgtgg aagaccacca cg                                     22

<210> SEQ ID NO 330
<211> LENGTH: 30
<212> TYPE: DNA
<213> ORGANISM: Amycolatopsis orientalis

<400> SEQUENCE: 330
aggggttaag gctcccagta gacgactggg                             30

<210> SEQ ID NO 331
<211> LENGTH: 22
<212> TYPE: DNA
<213> ORGANISM: Artificial sequence
```

```
<220> FEATURE:
<223> OTHER INFORMATION: Description of the artificial sequence: derived
      from species of the genera Brucella, Bradyrhizobium

<400> SEQUENCE: 331
agagccgtgg aagaccacca cg                                              22

<210> SEQ ID NO 332
<211> LENGTH: 30
<212> TYPE: DNA
<213> ORGANISM: Pseudomonas paucimobilis

<400> SEQUENCE: 332
aggaagtaag atccctgaaa gatgatcagg                                      30

<210> SEQ ID NO 333
<211> LENGTH: 22
<212> TYPE: DNA
<213> ORGANISM: Artificial sequence
<220> FEATURE:
<223> OTHER INFORMATION: Description of the artificial sequence: derived
      from species of the genera Rhodobacter, Rickettsia

<400> SEQUENCE: 333
agggccgtgg aagaccacca cg                                              22

<210> SEQ ID NO 334
<211> LENGTH: 26
<212> TYPE: DNA
<213> ORGANISM: Sphingomonas paucimobilis

<400> SEQUENCE: 334
agctccttga agggtcgttc gagacc                                          26

<210> SEQ ID NO 335
<211> LENGTH: 22
<212> TYPE: DNA
<213> ORGANISM: Zymomonas mobilis

<400> SEQUENCE: 335
agagccgtcg aagactacga cg                                              22

<210> SEQ ID NO 336
<211> LENGTH: 26
<212> TYPE: DNA
<213> ORGANISM: Artificial sequence
<220> FEATURE:
<223> OTHER INFORMATION: Description of the artificial sequence: derived
      from species of the genus Alcaligenes

<400> SEQUENCE: 336
tgtcctctaa agagccgttc gagact                                          26

<210> SEQ ID NO 337
<211> LENGTH: 25
<212> TYPE: DNA
<213> ORGANISM: Pseudomonas cepacia

<400> SEQUENCE: 337
tgtgtgagag gcccccagcc agacc                                           25

<210> SEQ ID NO 338
<211> LENGTH: 26
<212> TYPE: DNA
<213> ORGANISM: Ralstonia pickettii
```

```
<400> SEQUENCE: 338
agttccctga agggccgtcg aagact                                              26

<210> SEQ ID NO 339
<211> LENGTH: 14
<212> TYPE: DNA
<213> ORGANISM: Campylobacter jejuni

<400> SEQUENCE: 339
agaagactac tagt                                                           14

<210> SEQ ID NO 340
<211> LENGTH: 25
<212> TYPE: DNA
<213> ORGANISM: Helicobacter pylori

<400> SEQUENCE: 340
tgaagctcgc acaaagacta tgtgc                                               25

<210> SEQ ID NO 341
<211> LENGTH: 28
<212> TYPE: DNA
<213> ORGANISM: Actinoplanes utahensis

<400> SEQUENCE: 341
agtgggtaag gctcccagct agactact                                            28

<210> SEQ ID NO 342
<211> LENGTH: 31
<212> TYPE: DNA
<213> ORGANISM: Bacillus halodurans

<400> SEQUENCE: 342
aatccagtaa gacccttag agatgatgag g                                         31

<210> SEQ ID NO 343
<211> LENGTH: 30
<212> TYPE: DNA
<213> ORGANISM: Bacillus subtilis

<400> SEQUENCE: 343
aggaagtaag atccctgaaa gatgatcagg                                          30

<210> SEQ ID NO 344
<211> LENGTH: 32
<212> TYPE: DNA
<213> ORGANISM: Clostridium tyrobutyricum

<400> SEQUENCE: 344
agctggtaag gccccttgaa gaacacaagg tg                                       32

<210> SEQ ID NO 345
<211> LENGTH: 30
<212> TYPE: DNA
<213> ORGANISM: Artificial sequence
<220> FEATURE:
<223> OTHER INFORMATION: Description of the artificial sequence: derived
      from species of the genus Frankia

<400> SEQUENCE: 345
cctggtaagg ccccgacta gatgatcggg                                           30
```

-continued

<210> SEQ ID NO 346
<211> LENGTH: 30
<212> TYPE: DNA
<213> ORGANISM: Microbispora bispora

<400> SEQUENCE: 346
accgggtaag gctcccagta gatgactggg                                              30

<210> SEQ ID NO 347
<211> LENGTH: 31
<212> TYPE: DNA
<213> ORGANISM: Mycobacterium leprae

<400> SEQUENCE: 347
ggtgggataa ggccccccgc agaacacggg a                                            31

<210> SEQ ID NO 348
<211> LENGTH: 31
<212> TYPE: DNA
<213> ORGANISM: Mycobacterium smegmatis

<400> SEQUENCE: 348
ggagggataa ggccccccgc agaccacggg a                                            31

<210> SEQ ID NO 349
<211> LENGTH: 31
<212> TYPE: DNA
<213> ORGANISM: Mycobacterium tuberculosis

<400> SEQUENCE: 349
ggtgggataa ggccccccgc agaacacggg t                                            31

<210> SEQ ID NO 350
<211> LENGTH: 30
<212> TYPE: DNA
<213> ORGANISM: Propionibacterium freudenreichii

<400> SEQUENCE: 350
aatgtggtaa ggcccccggt agaccaccgg                                              30

<210> SEQ ID NO 351
<211> LENGTH: 31
<212> TYPE: DNA
<213> ORGANISM: Rhodococcus erythropolis

<400> SEQUENCE: 351 gaggggtaa ggccccccggc agaccaccgg g                                            31

<210> SEQ ID NO 352
<211> LENGTH: 29
<212> TYPE: DNA
<213> ORGANISM: Staphylococcus aureus

<400> SEQUENCE: 352
ggttataaga tccctcaaag atgatgagg                                               29

<210> SEQ ID NO 353
<211> LENGTH: 31
<212> TYPE: DNA
<213> ORGANISM: Streptococcus faecalis
<220> FEATURE:
<221> NAME/KEY: misc_feature
<222> LOCATION: (20)..(20)
<223> OTHER INFORMATION: n = Adenosine (A) or Guanosine (G) or Cytosine
      (C) or Thymidine (T) or Inosine (I)

<400> SEQUENCE: 353
aagaaagtaa gaccccctnan agatgatcag g                      31

<210> SEQ ID NO 354
<211> LENGTH: 30
<212> TYPE: DNA
<213> ORGANISM: Streptomyces ambifaciens

<400> SEQUENCE: 354
aggggttaag gctcccagta gacgactggg                          30

<210> SEQ ID NO 355
<211> LENGTH: 32
<212> TYPE: DNA
<213> ORGANISM: Flavobacterium resinovorum

<400> SEQUENCE: 355
accgccttga agggtcgttc gagaccagga cg                       32

<210> SEQ ID NO 356
<211> LENGTH: 22
<212> TYPE: DNA
<213> ORGANISM: Sphingobacterium multivorans

<400> SEQUENCE: 356
agggtcgtag aagatgacta cg                                  22

<210> SEQ ID NO 357
<211> LENGTH: 30
<212> TYPE: DNA
<213> ORGANISM: Artificial sequence
<220> FEATURE:
<223> OTHER INFORMATION: Description of the artificial sequence: derived
      from species of the genus Synechococcus

<400> SEQUENCE: 357
aagccagtaa ggtcacgggt agaacacccg                          30

<210> SEQ ID NO 358
<211> LENGTH: 30
<212> TYPE: DNA
<213> ORGANISM: Artificial sequence
<220> FEATURE:
<223> OTHER INFORMATION: Description of the artificial sequence: derived
      from species of the genus Synechocystis

<400> SEQUENCE: 358
aagccagtaa ggtcacggga agactacccg                          30

<210> SEQ ID NO 359
<211> LENGTH: 23
<212> TYPE: DNA
<213> ORGANISM: Borrelia burgdorferi

<400> SEQUENCE: 359
aagggtcctg gaagaatacc agg                                 23

<210> SEQ ID NO 360
<211> LENGTH: 26
<212> TYPE: DNA
<213> ORGANISM: Chlamydia trachomatis

<400> SEQUENCE: 360

-continued aatgagactc catgtagact acgtgg                                      26

<210> SEQ ID NO 361
<211> LENGTH: 40
<212> TYPE: DNA
<213> ORGANISM: Pseudomonas stutzeri

<400> SEQUENCE: 361
agtaatgcat taagctaacc agtactaatt gcccgtacgg                       40

<210> SEQ ID NO 362
<211> LENGTH: 40
<212> TYPE: DNA
<213> ORGANISM: Thiobacillus ferrooxidans

<400> SEQUENCE: 362
agcaatgcgt gcagctaagg agtactaatc ggccgtgcgg                       40

<210> SEQ ID NO 363
<211> LENGTH: 40
<212> TYPE: DNA
<213> ORGANISM: Agrobacterium vitis

<400> SEQUENCE: 363
ggtaacctgc gaagcttacc gttactaata gctcgattgg                       40

<210> SEQ ID NO 364
<211> LENGTH: 40
<212> TYPE: DNA
<213> ORGANISM: Adalia bipunctata

<400> SEQUENCE: 364
agtaatgcgt gtagctaacc gatactaata gctcgattga                       40

<210> SEQ ID NO 365
<211> LENGTH: 40
<212> TYPE: DNA
<213> ORGANISM: Brucella ovis

<400> SEQUENCE: 365
ggcaacgcat gcagcttacc ggtactaata gctcgatcga                       40

<210> SEQ ID NO 366
<211> LENGTH: 40
<212> TYPE: DNA
<213> ORGANISM: Bradyrhizobium japonicum

<400> SEQUENCE: 366
agtaatgcat gcagcttacc ggtactaatc gttcgattgg                       40

<210> SEQ ID NO 367
<211> LENGTH: 40
<212> TYPE: DNA
<213> ORGANISM: Pseudomonas paucimobilis

<400> SEQUENCE: 367
ggcgacacat ggagctgaca gatactaatc gatcgaggac                       40

<210> SEQ ID NO 368
<211> LENGTH: 40
<212> TYPE: DNA
<213> ORGANISM: Rhodobacter sphaeroides

<400> SEQUENCE: 368

```
agcaatgcgt tcagctgact ggtactaatt gcccgatagg                    40
```

<210> SEQ ID NO 369
<211> LENGTH: 40
<212> TYPE: DNA
<213> ORGANISM: Rickettsia prowazekii

<400> SEQUENCE: 369

```
agtaatgtgt gtagctaacc gatactaata gctcgattga                    40
```

<210> SEQ ID NO 370
<211> LENGTH: 40
<212> TYPE: DNA
<213> ORGANISM: Sphingomonas paucimobilis
<220> FEATURE:
<221> NAME/KEY: misc_feature
<222> LOCATION: (37)..(37)
<223> OTHER INFORMATION: n = Adenosine (A) or Guanosine (G) or Cytosine
      (C) or Thymidine (T) or Inosine (I)

<400> SEQUENCE: 370

```
agtaatgcat taagctaacc agtactaatt gcccgtncgg                    40
```

<210> SEQ ID NO 371
<211> LENGTH: 40
<212> TYPE: DNA
<213> ORGANISM: Zymomonas mobilis

<400> SEQUENCE: 371

```
ggtaacacat gtagctaact ggtcctaatt gctctattca                    40
```

<210> SEQ ID NO 372
<211> LENGTH: 40
<212> TYPE: DNA
<213> ORGANISM: Artificial sequence
<220> FEATURE:
<223> OTHER INFORMATION: Description of the artificial sequence: derived
      from species of the genus Alcaligenes

<400> SEQUENCE: 372

```
agtgatatgt gaagctgacc aatactaatt gctcgtgagg                    40
```

<210> SEQ ID NO 373
<211> LENGTH: 40
<212> TYPE: DNA
<213> ORGANISM: Ralstonia pickettii

<400> SEQUENCE: 373

```
tgtgaggcgt tgagctaacc aatactaatt gcccgtgagg                    40
```

<210> SEQ ID NO 374
<211> LENGTH: 40
<212> TYPE: DNA
<213> ORGANISM: Campylobacter jejuni

<400> SEQUENCE: 374

```
tgaaagtcct ttagctgacc agtactaata gagcgtttgg                    40
```

<210> SEQ ID NO 375
<211> LENGTH: 40
<212> TYPE: DNA
<213> ORGANISM: Helicobacter pylori

<400> SEQUENCE: 375

-continued agtaatgcgt ttagctgact actactaata gagcgtttgg         40

<210> SEQ ID NO 376
<211> LENGTH: 40
<212> TYPE: DNA
<213> ORGANISM: Bacillus halodurans

<400> SEQUENCE: 376
ggcgacacgt gaagctgaca gatactaatc ggtcgaggac         40

<210> SEQ ID NO 377
<211> LENGTH: 40
<212> TYPE: DNA
<213> ORGANISM: Bacillus subtilis

<400> SEQUENCE: 377
ggcgacacat ggagctgaca gatactaatc gatcgaggac         40

<210> SEQ ID NO 378
<211> LENGTH: 40
<212> TYPE: DNA
<213> ORGANISM: Clostridium tyrobutyricum

<400> SEQUENCE: 378
ggcaacatgt tcagctgact gatactaata ggccgagggc         40

<210> SEQ ID NO 379
<211> LENGTH: 41
<212> TYPE: DNA
<213> ORGANISM: Artificial sequence
<220> FEATURE:
<223> OTHER INFORMATION: Description of the artificial sequence: derived
      from species of the genus Frankia

<400> SEQUENCE: 379
cggtgacgca tggagctgac cggtactaat aggccgaggg c         41

<210> SEQ ID NO 380
<211> LENGTH: 42
<212> TYPE: DNA
<213> ORGANISM: Microbispora bispora

<400> SEQUENCE: 380
cggtaacgtg tggagccgac cggtactaat aagccgagag gc         42

<210> SEQ ID NO 381
<211> LENGTH: 41
<212> TYPE: DNA
<213> ORGANISM: Mycobacterium leprae

<400> SEQUENCE: 381
cagtaatgag tgtagggaac tggcactaac tggccgaaag c         41

<210> SEQ ID NO 382
<211> LENGTH: 41
<212> TYPE: DNA
<213> ORGANISM: Mycobacterium smegmatis

<400> SEQUENCE: 382
tagtaatagg tgcagggaac tggcactaac cggccgaaaa c         41

<210> SEQ ID NO 383
<211> LENGTH: 41
<212> TYPE: DNA

```
<213> ORGANISM: Mycobacterium tuberculosis

<400> SEQUENCE: 383
cagtaatggg tgtagggaac tggtgctaac cggccgaaaa c                         41

<210> SEQ ID NO 384
<211> LENGTH: 86
<212> TYPE: DNA
<213> ORGANISM: Mycobacterium gallisepticum

<400> SEQUENCE: 384
agaatcgttg tagactacga cgttgatagg ctaaaggtgt aagtgccgcg aggtatttag     60
ctgattagta ctaataattc gaggac                                         86

<210> SEQ ID NO 385
<211> LENGTH: 27
<212> TYPE: DNA
<213> ORGANISM: Propionibacterium freudenreichii

<400> SEQUENCE: 385
gctgaccgat actaagtggc cgagggc                                        27

<210> SEQ ID NO 386
<211> LENGTH: 41
<212> TYPE: DNA
<213> ORGANISM: Rhodococcus erythropolis

<400> SEQUENCE: 386
cagtaatgca tgcaggtgac tggtactaat aggccgagga c                         41

<210> SEQ ID NO 387
<211> LENGTH: 41
<212> TYPE: DNA
<213> ORGANISM: Rhodococcus fascians

<400> SEQUENCE: 387
cagcaatgta tgcaggtgac tggtactaat aggccgagga c                         41

<210> SEQ ID NO 388
<211> LENGTH: 27
<212> TYPE: DNA
<213> ORGANISM: Staphylococcus aureus

<400> SEQUENCE: 388
gctgacgaat actaatcgat cgagggc                                        27

<210> SEQ ID NO 389
<211> LENGTH: 27
<212> TYPE: DNA
<213> ORGANISM: Streptococcus faecalis

<400> SEQUENCE: 389
gcggaccaat actaatcggt cgaggac                                        27

<210> SEQ ID NO 390
<211> LENGTH: 51
<212> TYPE: DNA
<213> ORGANISM: Streptomyces ambifaciens

<400> SEQUENCE: 390
ccgcaaggtg tggaggtgac cggtactaat aggccgaggg cttgtcctca t              51
```

<210> SEQ ID NO 391
<211> LENGTH: 51
<212> TYPE: DNA
<213> ORGANISM: Streptomyces galbus

<400> SEQUENCE: 391
cggtaacgtg tggaggtgac cggtactaat aggccgaggg cttgtcctca g    51

<210> SEQ ID NO 392
<211> LENGTH: 51
<212> TYPE: DNA
<213> ORGANISM: Streptomyces griseus

<400> SEQUENCE: 392
cggtaacggg tggagctgac tggtactaat aggccgaggg cttgtcctca g    51

<210> SEQ ID NO 393
<211> LENGTH: 51
<212> TYPE: DNA
<213> ORGANISM: Streptomyces lividans

<400> SEQUENCE: 393
ccgtgaggtg tggaggtgac cggtactaat aggccgaggg cttgtcctca g    51

<210> SEQ ID NO 394
<211> LENGTH: 51
<212> TYPE: DNA
<213> ORGANISM: Streptomyces mashuensis

<400> SEQUENCE: 394
cggtaacggt tggagctgac tggtactaat aggccgaggg cttgtccata g    51

<210> SEQ ID NO 395
<211> LENGTH: 28
<212> TYPE: DNA
<213> ORGANISM: Flavobacterium resinovorum

<400> SEQUENCE: 395
gctaaccagt actaattgcc cgtaaggc    28

<210> SEQ ID NO 396
<211> LENGTH: 28
<212> TYPE: DNA
<213> ORGANISM: Sphingobacterium multivorans

<400> SEQUENCE: 396
gccaagtggt actaatagcc cgaagctt    28

<210> SEQ ID NO 397
<211> LENGTH: 27
<212> TYPE: DNA
<213> ORGANISM: Artificial sequence
<220> FEATURE:
<223> OTHER INFORMATION: Description of the artificial sequence: derived
      from species of the genus Synechococcus

<400> SEQUENCE: 397
gctgaggcgt actaatagac cgagggc    27

<210> SEQ ID NO 398
<211> LENGTH: 27
<212> TYPE: DNA
<213> ORGANISM: Artificial sequence
<220> FEATURE:
<223> OTHER INFORMATION: Description of the artificial sequence: derived from species of the genus Synechocystis

<400> SEQUENCE: 398
gtcgaggagt actaatagac cgagggc    27

<210> SEQ ID NO 399
<211> LENGTH: 27
<212> TYPE: DNA
<213> ORGANISM: Borrelia burgdorferi

<400> SEQUENCE: 399
gctgactaat actaattacc cgtatct    27

<210> SEQ ID NO 400
<211> LENGTH: 28
<212> TYPE: DNA
<213> ORGANISM: Chlamyia trachomatis

<400> SEQUENCE: 400
gctaaccaat actaataagt ccaaagac    28

<210> SEQ ID NO 401
<211> LENGTH: 36
<212> TYPE: DNA
<213> ORGANISM: Salmonella typhi

<400> SEQUENCE: 401 cttaaccta caacgccgaa gatgttttgg cggatg    36

<210> SEQ ID NO 402
<211> LENGTH: 35
<212> TYPE: DNA
<213> ORGANISM: Buchnera aphidocola

<400> SEQUENCE: 402 cttaaccta caacaccaga ggtgtttttt ataaa    35

<210> SEQ ID NO 403
<211> LENGTH: 35
<212> TYPE: DNA
<213> ORGANISM: Pseudomonas stutzeri

<400> SEQUENCE: 403
cttgaccata taacacccaa acaatttgat gtttg    35

<210> SEQ ID NO 404
<211> LENGTH: 35
<212> TYPE: DNA
<213> ORGANISM: Thiobacillus ferrooxidans

<400> SEQUENCE: 404
cttgaccata tatcaccaag cattaaagag cttcc    35

<210> SEQ ID NO 405
<211> LENGTH: 35
<212> TYPE: DNA
<213> ORGANISM: Sphingomonas paucimobilis

<400> SEQUENCE: 405 cttgtccta taaccttggt agtccaaggt cgagt    35

<210> SEQ ID NO 406
<211> LENGTH: 35

```
<212> TYPE: DNA
<213> ORGANISM: Artificial sequence
<220> FEATURE:
<223> OTHER INFORMATION: Description of the artificial sequence: derived
      from species of the genus Alcaligenes

<400> SEQUENCE: 406
cttgactata caacacccaa gcagttgtat ataaa                          35

<210> SEQ ID NO 407
<211> LENGTH: 23
<212> TYPE: DNA
<213> ORGANISM: Pseudomonas cepacia

<400> SEQUENCE: 407
aggactaacg actcgtgaag ctg                                       23

<210> SEQ ID NO 408
<211> LENGTH: 29
<212> TYPE: DNA
<213> ORGANISM: Ralstonia pickettii

<400> SEQUENCE: 408
cttgaccata taacacccaa gcaatttga                                 29

<210> SEQ ID NO 409
<211> LENGTH: 35
<212> TYPE: DNA
<213> ORGANISM: Campylobacter jejuni

<400> SEQUENCE: 409
cttatcttta ataaagcatc acttccttgt taagg                          35

<210> SEQ ID NO 410
<211> LENGTH: 35
<212> TYPE: DNA
<213> ORGANISM: Helicobacter pylori

<400> SEQUENCE: 410 cttgttttttt gcttttttgat aagataacgg caata                       35

<210> SEQ ID NO 411
<211> LENGTH: 33
<212> TYPE: DNA
<213> ORGANISM: Actinoplanes utahensis

<400> SEQUENCE: 411
cggtaacgtg ttgagttgac cggtactaat agg                            33

<210> SEQ ID NO 412
<211> LENGTH: 35
<212> TYPE: DNA
<213> ORGANISM: Bacillus halodurans

<400> SEQUENCE: 412
ttatccaaaa acaaatcaaa agcaacgtct cgaac                          35

<210> SEQ ID NO 413
<211> LENGTH: 21
<212> TYPE: DNA
<213> ORGANISM: Bacillus subtilis

<400> SEQUENCE: 413
ttaaccacat tttgaatgat g                                         21
```

-continued

<210> SEQ ID NO 414
<211> LENGTH: 32
<212> TYPE: DNA
<213> ORGANISM: Clostridium tyrobutyricum

<400> SEQUENCE: 414
ttgaccaaat ttatcttact gtgcaatttt ca 32

<210> SEQ ID NO 415
<211> LENGTH: 56
<212> TYPE: DNA
<213> ORGANISM: Artificial sequence
<220> FEATURE:
<223> OTHER INFORMATION: Description of the artificial sequence: derived from species of the genus Frankia

<400> SEQUENCE: 415
cggtgacgca tggagctgac cggtactaat aggccgaggg cttgtcttcg aaggtg 56

<210> SEQ ID NO 416
<211> LENGTH: 56
<212> TYPE: DNA
<213> ORGANISM: Microbispora bispora

<400> SEQUENCE: 416
cggtaacgtg tggagccgac cggtactaat aagccgagag gcttgacttc acatgc 56

<210> SEQ ID NO 417
<211> LENGTH: 56
<212> TYPE: DNA
<213> ORGANISM: Mycobacterium leprae

<400> SEQUENCE: 417
cagtaatgag tgtagggaac tggcactaac tggccgaaag cttacaaaac acacac 56

<210> SEQ ID NO 418
<211> LENGTH: 56
<212> TYPE: DNA
<213> ORGANISM: Mycobacterium smegmatis

<400> SEQUENCE: 418
tagtaatagg tgcagggaac tggcactaac cggccgaaaa cttacaacac cccata 56

<210> SEQ ID NO 419
<211> LENGTH: 56
<212> TYPE: DNA
<213> ORGANISM: Mycobacterium tuberculosis

<400> SEQUENCE: 419
cagtaatggg tgtagggaac tggtgctaac cggccgaaaa cttacaacac cctccc 56

<210> SEQ ID NO 420
<211> LENGTH: 39
<212> TYPE: DNA
<213> ORGANISM: Mycobacterium gallisepticum

<400> SEQUENCE: 420
cgttgatagg ctaaaggtgt aagtgccgcg aggtattta 39

<210> SEQ ID NO 421
<211> LENGTH: 39
<212> TYPE: DNA
<213> ORGANISM: Propionibacterium freudenreichii

```
<400> SEQUENCE: 421
ttgtcccaca ctttaattct tgtagattgt tgtgaagag                              39

<210> SEQ ID NO 422
<211> LENGTH: 41
<212> TYPE: DNA
<213> ORGANISM: Rhodococcus erythropolis

<400> SEQUENCE: 422
cagtaatgca tgcaggtgac tggtactaat aggccgagga c                          41

<210> SEQ ID NO 423
<211> LENGTH: 41
<212> TYPE: DNA
<213> ORGANISM: Rhodococcus fascians

<400> SEQUENCE: 423
cagcaatgta tgcaggtgac tggtactaat aggccgagga c                          41

<210> SEQ ID NO 424
<211> LENGTH: 33
<212> TYPE: DNA
<213> ORGANISM: Staphylococcus aureus

<400> SEQUENCE: 424
ttaaccaaaa taaatgtttt gcgaagcaaa atc                                   33

<210> SEQ ID NO 425
<211> LENGTH: 42
<212> TYPE: DNA
<213> ORGANISM: Streptococcus faecalis

<400> SEQUENCE: 425
ttaaccaaag aatggataag taaaagcaac ttggttattt tg                         42

<210> SEQ ID NO 426
<211> LENGTH: 56
<212> TYPE: DNA
<213> ORGANISM: Streptomyces lividans

<400> SEQUENCE: 426
ccgcaaggtg tggaggtgac cggtactaat aggccgaggg cttgtcctca tttgct          56

<210> SEQ ID NO 427
<211> LENGTH: 56
<212> TYPE: DNA
<213> ORGANISM: Streptomyces mashuensis

<400> SEQUENCE: 427
cggtaacggt tggagctgac tggtactaat aggccgaggg cttgtccata gttgct          56

<210> SEQ ID NO 428
<211> LENGTH: 43
<212> TYPE: DNA
<213> ORGANISM: Flavobacterium resinovorum

<400> SEQUENCE: 428
cttgatccta taaccagtgt gttttgcctg gtgggtgatc gcg                        43

<210> SEQ ID NO 429
<211> LENGTH: 28
<212> TYPE: DNA
```

```
<213> ORGANISM: Artificial sequence
<220> FEATURE:
<223> OTHER INFORMATION: Description of the artificial sequence: derived
      from species of the genus Synechococcus

<400> SEQUENCE: 429
ttgacctcta acactttgat atcggcac                                            28

<210> SEQ ID NO 430
<211> LENGTH: 28
<212> TYPE: DNA
<213> ORGANISM: Artificial sequence
<220> FEATURE:
<223> OTHER INFORMATION: Description of the artificial sequence: derived
      from species of the genus Synechocystis

<400> SEQUENCE: 430 ttgacctta ttcttcattt ttctttct                                             28

<210> SEQ ID NO 431
<211> LENGTH: 34
<212> TYPE: DNA
<213> ORGANISM: Chlamyia trachomatis

<400> SEQUENCE: 431
cttggtcttt ttatgattgg aagagccgaa aggc                                     34

<210> SEQ ID NO 432
<211> LENGTH: 51
<212> TYPE: DNA
<213> ORGANISM: Salmonella typhi

<400> SEQUENCE: 432 cttaaccta caacaccgaa ggtgttttgg aggataaaag aaacagaatt t                   51

<210> SEQ ID NO 433
<211> LENGTH: 117
<212> TYPE: DNA
<213> ORGANISM: Buchnera aphidocola

<400> SEQUENCE: 433
cttaacctta caacaccaga ggtgtttttt ataaaaaata aaaatcttg ttttactgaa          60 tttattgttg tattaatata tatatattat aatagcacta aaaatgcct ggtaaaa            117

<210> SEQ ID NO 434
<211> LENGTH: 233
<212> TYPE: DNA
<213> ORGANISM: Pseudomonas stutzeri

<400> SEQUENCE: 434
cttgaccata taacacccaa acaatttgat gtttgcgtgt cagacggttg aagtcgacaa         60
acaaaccgaa agacgcaacg ctcgcaaagc gaaagcgata ccgaagcaac catcacatac       120
ccaattaggg aagcgactca acaccgactc cccagttgaa cttgcttgac gaccatagag       180
cgttggaacc acctgatccc atcccgaact cagtagtgaa acgacgcatc gcc              233

<210> SEQ ID NO 435
<211> LENGTH: 91
<212> TYPE: DNA
<213> ORGANISM: Thiobacillus ferrooxidans

<400> SEQUENCE: 435
cttgaccata tatcaccaag cattaaagag cttcccttca gcaacacctc gagggcggca        60
```

-continued

```
cagccgcgcc cgggaccaga ccagttttaa c                                    91

<210> SEQ ID NO 436
<211> LENGTH: 230
<212> TYPE: DNA
<213> ORGANISM: Agrobacterium vitis

<400> SEQUENCE: 436
cttaatcgtt ctcattgacc atgctcatcg acttcgtcga tgagccatct gtttagcgct     60
cacgcatgag cggctcgtat acgagcctat gctccgcgag ggcgccgaac gatcggcgac    120
gcgccttgcg cttgcggact tcgtccgaaa gtgccaagca aaacgtcgcg gaatgacgtg    180
ttcacacaat aagaaaacgg gcaatgcccg ccagcttctc atcaacattg               230

<210> SEQ ID NO 437
<211> LENGTH: 162
<212> TYPE: DNA
<213> ORGANISM: Adalia bipunctata

<400> SEQUENCE: 437
tttactttgc tgtgagatta cacatgcata tggtgttaat tctataaaca tgtaagtatc     60
aactcacaaa gttatcaggt taaattagct ttatcaacca ataaagatgt tgttacatgt    120
ctctttctat gttgttcctg tgaaagtaag aatctagaaa aa                       162

<210> SEQ ID NO 438
<211> LENGTH: 120
<212> TYPE: DNA
<213> ORGANISM: Amycolatopsis orientalis

<400> SEQUENCE: 438
tggtaacggg tggagttgac tggtactaat aggccgaggg cttgtcctca gttgctcgcg     60
tccactgtgt tagttctgaa gtaacgaaca tcgccttgtc ggctggagtt caacttcata    120

<210> SEQ ID NO 439
<211> LENGTH: 189
<212> TYPE: DNA
<213> ORGANISM: Artificial sequence
<220> FEATURE:
<223> OTHER INFORMATION: Description of the artificial sequence: derived
      from species of the genus Brucella

<400> SEQUENCE: 439
cttgatcact cccatttaca atatccatca agcaaaagct tgatgttgaa ggcaatatgg     60
aagtagggca ataaggcaat atgtttgccc aaagccctca accatcgcca cgcagaaaaa    120
caaagcacaa aggcaaagaa caggcgcagc ccaaacatac tgccctattc ccctaatgcc    180
ttaagcccc                                                            189

<210> SEQ ID NO 440
<211> LENGTH: 109
<212> TYPE: DNA
<213> ORGANISM: Bradyrhizobium japonicum

<400> SEQUENCE: 440
cttgattgct ctcattttca gtgtccatag ggccgcaagg cccgcgacca gaatgaaatg     60
agaggcgcta gtcgcccaac aaagatcgct tgcttcgtat tccttgtcc                109

<210> SEQ ID NO 441
<211> LENGTH: 125
```

```
<212> TYPE: DNA
<213> ORGANISM: Pseudomonas paucimobilis

<400> SEQUENCE: 441
cttaaccaat tgaatgtat gcttactgtt atctagtttt gagagaacac tctcaatggt     60
ttggtggcga tagcgaagag gtcacacccg ttcccatgcc gaacacggaa gttaagctct   120
tcagc                                                              125

<210> SEQ ID NO 442
<211> LENGTH: 100
<212> TYPE: DNA
<213> ORGANISM: Rhodobacter sphaeroides

<400> SEQUENCE: 442
cttgatctga cccggtaaca gcaaggctca aaagccaacg ctctacccca gatcagaagc    60
aatagacccg gaacaagcaa aagcctgatg ttgtcgtttc                         100

<210> SEQ ID NO 443
<211> LENGTH: 196
<212> TYPE: DNA
<213> ORGANISM: Rickettsia prowazekii

<400> SEQUENCE: 443
tttactttgc tgtgagatta tatatgcata tagtgttaat tatataagta tttaagcatc    60
aatttgtaaa ttataatttt aatgttaaat tagctttatc aataaataaa aatgttattc   120
tatcgtttta tgttacgatt tgatagtaaa gttttgatct ttctttaaga tattgtagac   180
aattgtatat tatacc                                                   196

<210> SEQ ID NO 444
<211> LENGTH: 249
<212> TYPE: DNA
<213> ORGANISM: Pseudomonas cepacia

<400> SEQUENCE: 444
aggactaacg actcgtgaag ctgaccggta ctaataggcc gataacttac accacacacc    60
cttttcgtga acggattcaa aagacgttca caccaggaga gggtaaaaag aaaaaacaag   120
actgcttgcg tccactatgt ggttcccaac caacaaaccc gccacgggca cgttgcgaca   180
ggaacacaac tgaataacaa caccacaatg ttgtaaccac aaagacttcc cacccccggc   240
atcagaccc                                                           249

<210> SEQ ID NO 445
<211> LENGTH: 209
<212> TYPE: DNA
<213> ORGANISM: Ralstonia pickettii
<220> FEATURE:
<221> NAME/KEY: misc_feature
<222> LOCATION: (202)..(202)
<223> OTHER INFORMATION: n = Adenosine (A) or Guanosine (G) or Cytosine
      (C) or Thymidine (T) or Inosine (I)

<400> SEQUENCE: 445
cttgaccata taacacccaa gcaatttgag cgtaggcgcc aaattgtggt ggtgaagatg    60
atacgaaccg aaagttcgca acgaaccaca acatcacata tccgaattcg ctgggctgtc   120
catctggaca ttctggctac agaatttctt gacgaccata gagcattgga accacctgat   180
cccatcccga actcagcagt gnaacgatg                                     209
```

<210> SEQ ID NO 446
<211> LENGTH: 271
<212> TYPE: DNA
<213> ORGANISM: Campylobacter jejuni

<400> SEQUENCE: 446

```
cttatcttta ataaagcatc acttccttgt taaggttttt aagaagactt tgaatataga      60
taatatttag agtttaatag aaatctttca gtaaagtttt gtattagaac ttgctcttaa     120
cattgttttt taagtattct atataaaaac ttatcaaaga taaagataa gaaaagaaga     180
aagagaataa aagattaagt tttattctta aattcaattt ttcaaagaat atttaaataa     240
caatgtccgt gattatacag atgtggaaac g                                    271
```

<210> SEQ ID NO 447
<211> LENGTH: 228
<212> TYPE: DNA
<213> ORGANISM: Helicobacter pylori

<400> SEQUENCE: 447

```
cttgtttttt gcttttgat aagataacgg caataagcgc gaatggtta ccactgcctt       60
actgagtgta agagagttgg agttttatga agacttttat aagattaaac tttaatgagg    120
aatgagatac catctcaatg gtttaaagtt aaaggctatt aacgatcttc tttgttaaaa    180
acagctcccc tataaagaga aagggagtt aagggtaaat gcgtttttt                  228
```

<210> SEQ ID NO 448
<211> LENGTH: 155
<212> TYPE: DNA
<213> ORGANISM: Actinoplanes utahensis

<400> SEQUENCE: 448

```
cggtaacgtg ttgagttgac cggtactaat aggccgaggg cttaaccacc ctaaattttc      60
tgcttgcgtc cactgtgtga ttcacagcaa acgaacaacc accccggttc aagagtgccg    120
ggttgctggt ttgttctgct gatggctgtt tcgat                                155
```

<210> SEQ ID NO 449
<211> LENGTH: 296
<212> TYPE: DNA
<213> ORGANISM: Bacillus halodurans

<400> SEQUENCE: 449

```
cttatccaaa acaaatcaa aagcaacgtc tcgaactcga gaagcgtccc attatctagt       60
tttgagagaa tcttgttctc caaagaagcg ctccgacgca gcatcgcaag atgcgaagtt    120
gatcggaagc cgtgatcaag agattattct cttaggtcca agaaaaggg tttcgagaaa    180
cgagcagttt taggaatcga gcgacgacag atcggagcgt acacacggta cgtgaggatc    240
tggaggagtg aagatgacac caaaatgcga tgttgatcgg aggccgtaac tatcta         296
```

<210> SEQ ID NO 450
<211> LENGTH: 122
<212> TYPE: DNA
<213> ORGANISM: Bacillus halodurans

<400> SEQUENCE: 450

```
cttaaccaca ttttgaatga tgtcacacct gttatctagt tttgagagaa cacctctcta      60
aaggcggaag gtaaggaaac tccgctaagg gctctcacat cctgtgagaa acgcccagta    120
cc                                                                    122
```

-continued

<210> SEQ ID NO 451
<211> LENGTH: 209
<212> TYPE: DNA
<213> ORGANISM: Clostridium tyrobutyricum

<400> SEQUENCE: 451

```
cttgaccaaa tttatcttac tgtgcaattt tcagagaata attattctct tatctccatt 60
agaaatataa tgtttctatt ttattataga gaataaagta agtaaattga taataaccat 120
tagtacaagg aagatatgag cgaagagcgg aatttactta ggtaaatgag cactggagtg 180
aataattctg acggtgtaat gagaagtta 209

<210> SEQ ID NO 452
<211> LENGTH: 100
<212> TYPE: DNA
<213> ORGANISM: Artificial sequence
<220> FEATURE:
<223> OTHER INFORMATION: Description of the artificial sequence: derived
from species of the genus Frankia
<400> SEQUENCE: 452
cggtgacgca tggagctgac cggtactaat aggccgaggg cttgtcttcg aaggtgctac 60
gcgtccactg tgcggttctc gggtgtacgg ccggttcggc 100

<210> SEQ ID NO 453
<211> LENGTH: 85
<212> TYPE: DNA
<213> ORGANISM: Microbispora bispora
<400> SEQUENCE: 453
cggtaacgtg tggagccgac cggtactaat aagccgagag gcttgacttc acatgcacgc 60
acccactatg cgattctcga tcagc 85

<210> SEQ ID NO 454
<211> LENGTH: 124
<212> TYPE: DNA
<213> ORGANISM: Mycobacterium leprae
<400> SEQUENCE: 454
cagtaatgag tgtagggaac tggcactaac tggccgaaag cttacaaaac acacacatcg 60
caaccacata attcagatcc actttgtcgt ggagcatcac accccccatc agaacaaatt 120
ttta 124

<210> SEQ ID NO 455
<211> LENGTH: 146
<212> TYPE: DNA
<213> ORGANISM: Mycobacterium smegmatis
<400> SEQUENCE: 455
tagtaatagg tgcagggaac tggcactaac cggccgaaaa cttacaacac cccataatcg 60
ttgtaagaag aaaacattga cgcaccgcgc tcgcaaccac actccacgga tgatcaaacc 120
cacaagtttg ctctccatgt gggtca 146

<210> SEQ ID NO 456
<211> LENGTH: 135
<212> TYPE: DNA
<213> ORGANISM: Mycobacterium tuberculosis

<400> SEQUENCE: 456
```

```
cagtaatggg tgtagggaac tggtgctaac cggccgaaaa cttacaacac cctcccttttt     60 ggaaaaggga ggcaaaaaca aactcgcaac cacatccgtt cacggcgcta gccgtgcgtc    120 cacaccccccc accag                                                    135

<210> SEQ ID NO 457
<211> LENGTH: 169
<212> TYPE: DNA
<213> ORGANISM: Mycobacterium gallisepticum

<400> SEQUENCE: 457
cgttgatagg ctaaaggtgt aagtgccgcg aggtatttag ctgattagta ctaataattc     60
gaggacttag atttgatcaa aaacattagc tgttttttat ctaatatgat tgttgtatt    120 ttgttttttca aagagcaatg tgtgtgatat cgatatcgtg atggaaaca               169

<210> SEQ ID NO 458
<211> LENGTH: 43
<212> TYPE: DNA
<213> ORGANISM: Propionibacterium freudenreichii

<400> SEQUENCE: 458
cttgtcccac actttaattc ttgtagattg ttgtgaagag ttt                       43

<210> SEQ ID NO 459
<211> LENGTH: 182
<212> TYPE: DNA
<213> ORGANISM: Rhodococcus erythropolis

<400> SEQUENCE: 459
cagtaatgca tgcaggtgac tggtactaat aggccgagga cttaccacaa agaagctacg     60
cgtccactgt gcggtatctg aaacaacaca cagatactga tgagaaaccc tgttttctcc    120
atcccccaac accagaaaact ggtgttgacg tggtgaaacc aggtgatcag aagaaggtta   180
ct                                                                   182

<210> SEQ ID NO 460
<211> LENGTH: 168
<212> TYPE: DNA
<213> ORGANISM: Rhodococcus fascians

<400> SEQUENCE: 460
cagcaatgta tgcaggtgac tggtactaat aggccgagga cttaccacaa agaagctacg     60
cgtccactgt gcaatatctg aaacaacaca cgagtagttg ttcgacaaca gaaccgaata    120
cacgaatccg ccaccacac gagtgtgggt gacaggttcg ctcgttga                  168

<210> SEQ ID NO 461
<211> LENGTH: 64
<212> TYPE: DNA
<213> ORGANISM: Staphylococcus aureus

<400> SEQUENCE: 461
cttaaccaaa ataaatgttt tgcgaagcaa aatcactttt acttactatc tagttttgaa     60
tgta                                                                  64

<210> SEQ ID NO 462
<211> LENGTH: 87
<212> TYPE: DNA
<213> ORGANISM: Streptococcus faecalis
<220> FEATURE:
<221> NAME/KEY: misc_feature
```

```
<222> LOCATION: (82)..(82)
<223> OTHER INFORMATION: n = Adenosine (A) or Guanosine (G) or Cytosine
      (C) or Thymidine (T) or Inosine (I)

<400> SEQUENCE: 462
cttaaccaaa gaatggataa gtaaaagcaa cttggttatt ttgattcaaa cttcaatcca      60
gttttgagtg aatnaagatt cnctcaa                                         87

<210> SEQ ID NO 463
<211> LENGTH: 123
<212> TYPE: DNA
<213> ORGANISM: Streptomyces ambifaciens

<400> SEQUENCE: 463
ccgcaaggtg tggaggtgac cggtactaat aggccgaggg cttgtcctca tttgctcgcg      60
tccactgtgt tggttctgaa accacgaaca accccatgtg ccacacatgg tgcggttgtc     120
agt                                                                  123

<210> SEQ ID NO 464
<211> LENGTH: 134
<212> TYPE: DNA
<213> ORGANISM: Streptomyces galbus

<400> SEQUENCE: 464
cggtaacgtg tggaggtgac cggtactaat aggccgaggg cttgtcctca gttgctcgcg      60
tccactgtgt tggttctgaa accacgaaca gccccatgct ctggcatggt gcggcattgt     120
tcgacagttt cata                                                      134

<210> SEQ ID NO 465
<211> LENGTH: 143
<212> TYPE: DNA
<213> ORGANISM: Streptomyces griseus

<400> SEQUENCE: 465
cggtaacggg tggagctgac tggtactaat aggccgaggg cttgtcctca gttgctcgcg      60
tccactgtgt tgttcccggg ttgcgaacag ttatcgcacc ggttgaacag tttcactact     120
taattgaaga gtgtgcttgt tcg                                            143

<210> SEQ ID NO 466
<211> LENGTH: 137
<212> TYPE: DNA
<213> ORGANISM: Streptomyces lividans

<400> SEQUENCE: 466
ccgtgaggtg tggaggtgac cggtactaat aggccgaggg cttgtcctca gttgctcgcg      60
tccactgtgt tagttctgag gcaacgaccg ttgccggatt tgagtagaac gcacaattaa     120
agagtgtgct tgttcgc                                                   137

<210> SEQ ID NO 467
<211> LENGTH: 135
<212> TYPE: DNA
<213> ORGANISM: Streptomyces mashuensis

<400> SEQUENCE: 467
cggtaacggt tggagctgac tggtactaat aggccgaggg cttgtccata gttgctcgcg      60
ttcactgtgt tggttctgaa acaacaacca agaagcatac gccgtgtgtg gttgacagtt     120
tcatagtgtt tcggt                                                     135
```

<210> SEQ ID NO 468
<211> LENGTH: 114
<212> TYPE: DNA
<213> ORGANISM: Flavobacterium resinovorum

<400> SEQUENCE: 468
cttgatccta taaccagtgt gttttgcctg gtgggtgatc gcgactgtgc cgaaacagtt    60
gacacgcaca accccaacta catccctatt cgcagcgttg acctcaacct cagc          114

<210> SEQ ID NO 469
<211> LENGTH: 126
<212> TYPE: DNA
<213> ORGANISM: Sphingobacterium multivorans

<400> SEQUENCE: 469
ctttctcaag cagataacac tgttgtcttc ctctttaatt tttagaaacg aaaagaataa    60
caaaaaagaa acgaagctct ttcaatagat atgtcagttg gcctgacgat gatatattat   120
cataag                                                              126

<210> SEQ ID NO 470
<211> LENGTH: 63
<212> TYPE: DNA
<213> ORGANISM: Artificial sequence
<220> FEATURE:
<223> OTHER INFORMATION: Description of the artificial sequence: derived
      from species of the genus Synechococcus

<400> SEQUENCE: 470
cttgacctct aacactttga tatcggcact ctcctctatg cagccttcaa ggctctaatc    60
tcc                                                                 63

<210> SEQ ID NO 471
<211> LENGTH: 67
<212> TYPE: DNA
<213> ORGANISM: Artificial sequence
<220> FEATURE:
<223> OTHER INFORMATION: Description of the artificial sequence: derived
      from species of the genus Synechocystis

<400> SEQUENCE: 471
cttgaccttt attcttcatt tttctttctc ttttcttgtg cagtcttctg ggtttcttct    60
cagcaaa                                                             67

<210> SEQ ID NO 472
<211> LENGTH: 17
<212> TYPE: DNA
<213> ORGANISM: Borrelia burgdorferi

<400> SEQUENCE: 472
ctttggccat atttttg                                                  17

<210> SEQ ID NO 473
<211> LENGTH: 111
<212> TYPE: DNA
<213> ORGANISM: Chlamydia trachomatis

<400> SEQUENCE: 473
cttggtcttt ttatgattgg aagagccgaa aggcaaagac aataagaaaa agagtagaga    60
gtgcaagtac gtagaagaca agcttttaag cgtctattag tatacgtgag a            111

-continued

```
<210> SEQ ID NO 474
<211> LENGTH: 148
<212> TYPE: DNA
<213> ORGANISM: Azotobacter vinelandii
<400> SEQUENCE: 474
aaacaatctg ttgccagccc cagcggggcg gcacggagag ggcgcagccg acaggccgaa 60
gatttggctg gaccgcacgc tgccggaaac aggctaccgc tatcacctac ccgattggct 120
gtcgtgtcat cgacacggcg gcaaccga 148

<210> SEQ ID NO 475
<211> LENGTH: 229
<212> TYPE: DNA
<213> ORGANISM: Cowduria ruminantium
<400> SEQUENCE: 475
ggtgtgtaag tatggtaaca tatgtagcta accagtacta atagcccgat tgatttactt 60
aatttgtaat tatatgtagt attaaaactg cagcttgtct ttttgcttat tttgttttat 120
agtttaattg ggttggtggt aatagcagaa gtgatacacc cagctacatt tcgaacctgg 180
aagttaagcc ttctagcgct tatggtactt tgtcttaagg cacgggaga 229

<210> SEQ ID NO 476
<211> LENGTH: 110
<212> TYPE: DNA
<213> ORGANISM: Mycobacterium intracellulare
<400> SEQUENCE: 476
taagcttgat tcacacactc gcaaccacag tccatttcgc gcgttctgcc gctgaagcta 60
gaacaccgca ccccccacca aacaaattta aatagagtta cggcggccac 110

<210> SEQ ID NO 477
<211> LENGTH: 107
<212> TYPE: DNA
<213> ORGANISM: Mycobacterium lufu
<400> SEQUENCE: 477
aaaacttacc gaacacacaa tcgcaaccac agtccatttc acggcagcaa tgccgcgaaa 60
cgccacaccc cccaccaaac aaatttaaat agagttacgg cggccac 107

<210> SEQ ID NO 478
<211> LENGTH: 120
<212> TYPE: DNA
<213> ORGANISM: Mycobacterium simiae
<400> SEQUENCE: 478
taagcttgat tcacacacat cgcaaccact atcgtcgcga cttattgtcg cgccgaatgc 60
cacacccccc accagaacaa ctaataaaat agtgttccgt aatagagtta cggcggccac 120

<210> SEQ ID NO 479
<211> LENGTH: 149
<212> TYPE: DNA
<213> ORGANISM: Mycobacterium smegmatis
<400> SEQUENCE: 479
caccccataa cgttgtaaga agaaaacatt gaccaccgcg ctcgcaacca cactccacgg 60
atgatcaaac cgatcacccc accaccaaaa caaacccaca agtttgctct ccatgtgggt 120
caccacataa gagaatagag ttacggcgg 149
```

<210> SEQ ID NO 480
<211> LENGTH: 75
<212> TYPE: DNA
<213> ORGANISM: Saccharomonospora azurea

<400> SEQUENCE: 480
caaagatgct acgcacccac tctgcaactc tgaaacacca caccccggaa acatgatcct    60
gggttgtttc acagt    75

<210> SEQ ID NO 481
<211> LENGTH: 73
<212> TYPE: DNA
<213> ORGANISM: Saccharomonospora caesia

<400> SEQUENCE: 481
caaagatgct acgcacccac tctgcaactc tgaaacacca caccccggaa acgatcctgg    60
gttgtttcac agt    73

<210> SEQ ID NO 482
<211> LENGTH: 75
<212> TYPE: DNA
<213> ORGANISM: Saccharomonospora cyanea

<400> SEQUENCE: 482
caaacatgct acgcacccac tctgcaactc tgaaacacca ccccgggaac acaccccggcg    60 tgattgtttc ccaga    75

<210> SEQ ID NO 483
<211> LENGTH: 69
<212> TYPE: DNA
<213> ORGANISM: Saccharomonospora glauca

<400> SEQUENCE: 483
caaagacgct acgcacccac tctgcgactc tgaaacacca ccctggtgtg ccagtggttg    60
tttcacaga    69

<210> SEQ ID NO 484
<211> LENGTH: 74
<212> TYPE: DNA
<213> ORGANISM: Saccharomonospora viridis

<400> SEQUENCE: 484
caaaggtgct acgcacccac tctgcaactc tgaaacacca caccccaca acaccgggct    60 ggttgtttca caga    74

<210> SEQ ID NO 485
<211> LENGTH: 304
<212> TYPE: DNA
<213> ORGANISM: Wolbachia pipientis

<400> SEQUENCE: 485
taactggtac taatagcctg attgatttat ttgctttcta tatgtgcata tgcagtgtta    60
aatattaagt taaaatttat taagtcagaa atttttgttg acttggtggc tatagcaaaa    120
atgaaccacc cgatctcatt tcgaactcgg aagtgaaact tttagcgcc gatgatactt     180 aaaaacccaa agtaggtcgt tgccaagttt ataaaaattt cttcttattt atatcttttc    240
agtagagcga tgaaacaagg taaacataga gtagctgtga ggtaatataa ctgatctttt    300

```
                                            -continued
agaa                                                                  304

<210> SEQ ID NO 486
<211> LENGTH: 34
<212> TYPE: DNA
<213> ORGANISM: Salmonella typhi

<400> SEQUENCE: 486
ttcctggcgg cactagcgcg gtggtcccac ctga                                  34

<210> SEQ ID NO 487
<211> LENGTH: 22
<212> TYPE: DNA
<213> ORGANISM: Buchnera aphidocola

<400> SEQUENCE: 487
atagtgtagt ggtaccacct ga                                               22

<210> SEQ ID NO 488
<211> LENGTH: 53
<212> TYPE: DNA
<213> ORGANISM: Pseudomonas stutzeri

<400> SEQUENCE: 488
catcgccgat ggtagctgtg gggtctcccc atgtgagagt aggtcatcgt caa             53

<210> SEQ ID NO 489
<211> LENGTH: 35
<212> TYPE: DNA
<213> ORGANISM: Thiobacillus ferrooxidans

<400> SEQUENCE: 489
cttgtctggc ggccatagcg cagtggaacc accccc                                35

<210> SEQ ID NO 490
<211> LENGTH: 52
<212> TYPE: DNA
<213> ORGANISM: Agrobacterium vitis

<400> SEQUENCE: 490
atcaacattg cccttagctg acctggtggt catggcgggg cggccgcacc cg              52

<210> SEQ ID NO 491
<211> LENGTH: 38
<212> TYPE: DNA
<213> ORGANISM: Adalia bipunctata

<400> SEQUENCE: 491
gccatgcaac aatgttaaca gcagactaat acaaatct                              38

<210> SEQ ID NO 492
<211> LENGTH: 52
<212> TYPE: DNA
<213> ORGANISM: Artificial sequence
<220> FEATURE:
<223> OTHER INFORMATION: Description of the artificial sequence: derived
      from species of the genus Brucella

<400> SEQUENCE: 492
atgtttgtgt tcttcgccga cctggtggtt atggcggagc ggccgcaccc ga              52

<210> SEQ ID NO 493
<211> LENGTH: 40
<212> TYPE: DNA
```

<213> ORGANISM: Bradyrhizobium japonicum

<400> SEQUENCE: 493
ttcgccggcc tggtggtttt agcgaagagc ctcaacccga                          40

<210> SEQ ID NO 494
<211> LENGTH: 36
<212> TYPE: DNA
<213> ORGANISM: Pseudomonas paucimobilis

<400> SEQUENCE: 494
tcttcagcgc cgatggtagt cggggttccc cctaat                              36

<210> SEQ ID NO 495
<211> LENGTH: 40
<212> TYPE: DNA
<213> ORGANISM: Rhodobacter sphaeroides

<400> SEQUENCE: 495
ttctccggtc tggtggccat agcacgagca aaacacccga                          40

<210> SEQ ID NO 496
<211> LENGTH: 53
<212> TYPE: DNA
<213> ORGANISM: Rickettsia prowazekii

<400> SEQUENCE: 496
ccttgcttaa gaataatata atagcattaa cagcatatta taatacaacc tat           53

<210> SEQ ID NO 497
<211> LENGTH: 51
<212> TYPE: DNA
<213> ORGANISM: Rickettsia bellii

<400> SEQUENCE: 497
aaatttcttt aagtcctgca acaacactaa cagcaaacca atacaaatct a             51

<210> SEQ ID NO 498
<211> LENGTH: 53
<212> TYPE: DNA
<213> ORGANISM: Rickettsia rickettsii

<400> SEQUENCE: 498
gaattttttt gagtcgtgca acaacattaa cagtagacta taatacaaat cta           53

<210> SEQ ID NO 499
<211> LENGTH: 47
<212> TYPE: DNA
<213> ORGANISM: Sphingomonas paucimobilis

<400> SEQUENCE: 499
gccagacaag tcaaagcctg atgaccatag caagtcggtc ccacccc                  47

<210> SEQ ID NO 500
<211> LENGTH: 33
<212> TYPE: DNA
<213> ORGANISM: Zymomonas mobilis

<400> SEQUENCE: 500
gcttggtggc tatagcgtca gtgacccacc cga                                 33

<210> SEQ ID NO 501
<211> LENGTH: 53

-continued

<212> TYPE: DNA
<213> ORGANISM: Artificial sequence
<220> FEATURE:
<223> OTHER INFORMATION: Description of the artificial sequence: derived
      from species of the genus Alcaligenes

<400> SEQUENCE: 501
gcaagtatcc ataccagttg tgctggcgac catagcaaga gtgaaccacc tga        53

<210> SEQ ID NO 502
<211> LENGTH: 51
<212> TYPE: DNA
<213> ORGANISM: Pseudomonas cepacia

<400> SEQUENCE: 502
cgggcggacg ggtacaaggg ttacggcggt catagcgtgg gggaaacgcc c          51

<210> SEQ ID NO 503
<211> LENGTH: 48
<212> TYPE: DNA
<213> ORGANISM: Ralstonia pickettii

<400> SEQUENCE: 503
catcgccgat ggtagtgtgg ggtttcccca tgcgagagta ggacatag              48

<210> SEQ ID NO 504
<211> LENGTH: 51
<212> TYPE: DNA
<213> ORGANISM: Helicobacter pylori

<400> SEQUENCE: 504
ttatctttag ctcccttttc cttgtgcctt tagagaagag gaactaccca g          51

<210> SEQ ID NO 505
<211> LENGTH: 52
<212> TYPE: DNA
<213> ORGANISM: Bacillus halodurans

<400> SEQUENCE: 505
caaagaggat caagagattt gcggaagcaa gcgagtgacg aactgagcgt at         52

<210> SEQ ID NO 506
<211> LENGTH: 52
<212> TYPE: DNA
<213> ORGANISM: Bacillus halodurans

<400> SEQUENCE: 506
ccttcatcct gaaggcattt gtttggtggc gatagcgaag aggtcacacc cg         52

<210> SEQ ID NO 507
<211> LENGTH: 52
<212> TYPE: DNA
<213> ORGANISM: Clostridium tyrobutyricum

<400> SEQUENCE: 507
ttagcagcaa tttacggttg atctggtaac aatgacgtga aggtaacact cc         52

<210> SEQ ID NO 508
<211> LENGTH: 51
<212> TYPE: DNA
<213> ORGANISM: Artificial sequence
<220> FEATURE:
<223> OTHER INFORMATION: Description of the artificial sequence: derived
      from species of the genus Frankia

```
<400> SEQUENCE: 508
ggttgtatag ttgaatagtg tttcggtggt tttggcgaag gggaaacgcc c          51

<210> SEQ ID NO 509
<211> LENGTH: 50
<212> TYPE: DNA
<213> ORGANISM: Microbispora bispora

<400> SEQUENCE: 509
gtcctcacct gaaggcttgc cgctatcccg cgtcgagcag gtgaattccg            50

<210> SEQ ID NO 510
<211> LENGTH: 45
<212> TYPE: DNA
<213> ORGANISM: Mycobacterium leprae

<400> SEQUENCE: 510
aattttatag agttacggtg gccacagcga tagggaaacg cccgg                 45

<210> SEQ ID NO 511
<211> LENGTH: 52
<212> TYPE: DNA
<213> ORGANISM: Mycobacterium smegmatis

<400> SEQUENCE: 511
accacataag agaatagagt tacggcggtc catagcggca gggaaacgcc cg          52

<210> SEQ ID NO 512
<211> LENGTH: 49
<212> TYPE: DNA
<213> ORGANISM: Mycobacterium tuberculosis

<400> SEQUENCE: 512
agaacaaatt tgcatagagt tacggcggcc acagcggcag ggaaacgcc             49

<210> SEQ ID NO 513
<211> LENGTH: 51
<212> TYPE: DNA
<213> ORGANISM: Rhodococcus erythropolis

<400> SEQUENCE: 513
ctgtgacagt ttcatagagt tacggcggtc atagcgaagg ggaaacgccc g          51

<210> SEQ ID NO 514
<211> LENGTH: 52
<212> TYPE: DNA
<213> ORGANISM: Rhodococcus fascians

<400> SEQUENCE: 514
ttgacactgt ttcgcagagt tacggcggcc atagcggagg ggaaaccgcc cg         52

<210> SEQ ID NO 515
<211> LENGTH: 53
<212> TYPE: DNA
<213> ORGANISM: Staphylococcus aureus

<400> SEQUENCE: 515
tgtataaatt acattcatat gtctggtgac tatagcaagg aggtcacacc tgt        53

<210> SEQ ID NO 516
<211> LENGTH: 50
<212> TYPE: DNA
<213> ORGANISM: Streptococcus faecalis
```

```
<400> SEQUENCE: 516
taagaaacaa cacccagtgt ggtggcgata gcgagaagga tacacctgtt           50

<210> SEQ ID NO 517
<211> LENGTH: 47
<212> TYPE: DNA
<213> ORGANISM: Streptomyces ambifaciens

<400> SEQUENCE: 517
tcagtttcat agtgtttcgg tggtcatagc gttagggaaa cgcccgg              47

<210> SEQ ID NO 518
<211> LENGTH: 53
<212> TYPE: DNA
<213> ORGANISM: Artificial sequence
<220> FEATURE:
<223> OTHER INFORMATION: Description of the artificial sequence: derived
      from species of the genus Streptomyces

<400> SEQUENCE: 518
ttcgctagaa cccgataggg tttcggtggt cattgcgtta gggaaacgcc cgg       53

<210> SEQ ID NO 519
<211> LENGTH: 47
<212> TYPE: DNA
<213> ORGANISM: Flavobacterium resinovorum

<400> SEQUENCE: 519
gctgcaaccc ctcatgcctg gtgaccatag cgagctggaa ccacccc              47

<210> SEQ ID NO 520
<211> LENGTH: 52
<212> TYPE: DNA
<213> ORGANISM: Spingobacterium multivorans

<400> SEQUENCE: 520
taagacagac caataaagat ttttaggtgc ctatatcggc ggtgtctacc tc        52

<210> SEQ ID NO 521
<211> LENGTH: 53
<212> TYPE: DNA
<213> ORGANISM: Artificial sequence
<220> FEATURE:
<223> OTHER INFORMATION: Description of the artificial sequence: derived
      from species of the genus Synechococcus

<400> SEQUENCE: 521
ccatagagtc acacccttcc tggtgtctat ggcggtatgg aaccactctg acc       53

<210> SEQ ID NO 522
<211> LENGTH: 60
<212> TYPE: DNA
<213> ORGANISM: Artificial sequence
<220> FEATURE:
<223> OTHER INFORMATION: Description of the artificial sequence: derived
      from species of the genus Synechocystis

<400> SEQUENCE: 522
agcaaaaccc aaaatctttt cttggtgtct ttagcgtcat ggaaccactc cgatcccatc   60

<210> SEQ ID NO 523
<211> LENGTH: 53
<212> TYPE: DNA
<213> ORGANISM: Borrelia burgdorferi
```

```
<400> SEQUENCE: 523
ttttgtcttc cttgtaaaaa ccctggtggt taaagaaaag aggaaacacc tgt          53

<210> SEQ ID NO 524
<211> LENGTH: 51
<212> TYPE: DNA
<213> ORGANISM: Chlamydia trachomatis

<400> SEQUENCE: 524
gagaaacgat gccaggatta gcttggtgat aatagagaga gggaaacacc t            51

<210> SEQ ID NO 525
<211> LENGTH: 138
<212> TYPE: DNA
<213> ORGANISM: Sphingomonas paucimobilis
<220> FEATURE:
<221> NAME/KEY: misc_feature
<222> LOCATION: (114)..(114)
<223> OTHER INFORMATION: n = Adenosine (A) or Guanosine (G) or Cytosine
      (C) or Thymidine (T) or Inosine (I)

<400> SEQUENCE: 525
ctataacctt ggtagtccaa ggtcgagtac aactgctcga tacaagctac aacccaacaa    60
tacttcttcc agattcatgg ccacgctgaa caaagcgtag ggtgggcggc tgtnccgccc   120
acgcgtaact caagcgta                                                 138

<210> SEQ ID NO 526
<211> LENGTH: 107
<212> TYPE: DNA
<213> ORGANISM: Zymomonas mobilis

<400> SEQUENCE: 526
ttttgagaac tccactgtca atgtcagcat tgctgacctg ataatgtttt ctcttagctc    60
ttttgaatat cttcgatttt caattaactt cacgcacagg tgtcata                107

<210> SEQ ID NO 527
<211> LENGTH: 167
<212> TYPE: DNA
<213> ORGANISM: Artificial sequence
<220> FEATURE:
<223> OTHER INFORMATION: Description of the artificial sequence: derived
      from species of the genus Alcaligenes

<400> SEQUENCE: 527
atacaacacc caagcagttg tatataaagc atcaatcgat tcattaatat gcaaagcaac    60
ttgatttagt tatacgctta gctaaaatga acaaaatata gtaagactca atcagcccat   120
ctgtaaagat ttggaaaacg catcggcaac caataagacc aatgcaa                167

<210> SEQ ID NO 528
<211> LENGTH: 225
<212> TYPE: DNA
<213> ORGANISM: Borrelia burgdorferi

<400> SEQUENCE: 528
ctgcgagttc gcgggagagt aagttattgc cagggttttt tatttttttt tagtttttat    60
gttatttaaa tggcttattc aaacaacata aaaagaaaa tagatattga catggattaa    120
acaaaagata tatattattc tatgttgcat aaacaaattg gcaaagtaga gatggaagat   180
aaaaatatgg tcaaagtaat aagagtctat ggtgaatgcc tagga                  225
```

```
<210> SEQ ID NO 529
<211> LENGTH: 681
<212> TYPE: DNA
<213> ORGANISM: Xanthomonas campestris

<400> SEQUENCE: 529
tggagcaaga cgtcattcgt cctagtcggg cgtcctcaca aattacctgc attcagagat      60
tcataccggc acaggtcggt atgcgaagtc ccttttgggg ccttagctca gctgggagag     120
cacctgcttt gcaagcaggg ggtcgtcggt tcgatcccga caggctccac catattgagt     180
gaaaagactt cgggtctgta gctcaggtgg ttagagcgca ccctgataa gggtgaggtc      240 ggtagttcga gtctacccag acccaccact ctgaatgtag tgcacactta agaatttata     300
tggatcagcg ttgaggctga gacatgttct tttataactt gtgacgtagc gagcgtttga    360
gatatctatc taaacgtgtc gttgaagcta aggcggggac ttcgagtccc taaataattg    420
agtcgtatgt tcgcgttggg tggctttgtt acccacacaa cacgtacatg ttagctccga    480
ggcaacttgg ggttatatgg tcaagcgaat aagcgcacac ggtggatgcc taggcggtca    540
gtggcgatgt aggacgtggt agcctgcgaa aagtgtcggg gagctggcaa caagctttga    600
tccggcaata tccgaatggg gaaacccact gcttcggcag tatcttgcag tgaattcata    660
gctgcttgaa gcgaaccccg t                                              681

<210> SEQ ID NO 530
<211> LENGTH: 229
<212> TYPE: DNA
<213> ORGANISM: Cowduria ruminantium

<400> SEQUENCE: 530
ggtgtgtaag tatggtaaca tatgtagcta accagtacta atagcccgat tgatttactt      60
aatttgtaat tatatgtagt attaaaactg cagcttgtct ttttgcttat tttgttttat    120
agtttaattg ggttggtggt aatagcagaa gtgatacacc cagctacatt tcgaacctgg    180
aagttaagcc ttctagcgct tatggtactt tgtcttaagg cacgggaga                229
```

NUCLEIC ACID MOLECULES FOR DETECTING BACTERIA AND PHYLOGENETIC UNITS OF BACTERIA

Figure 1:
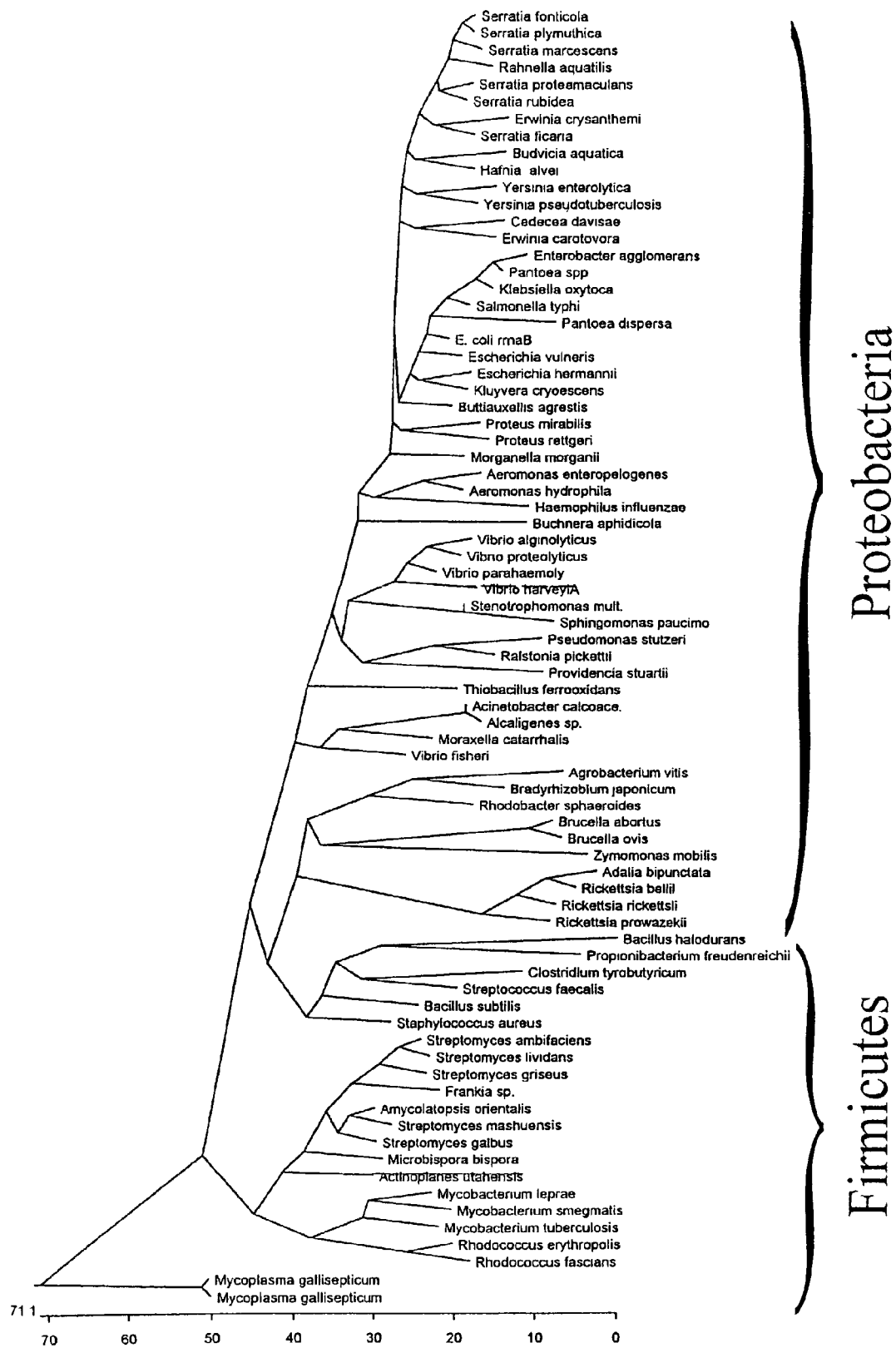

The present invention relates to nucleic acid molecules which allow the identification of bacteria or groups of bacteria.

Bacteria are an ubiquitous component of the human environment. But they cause problems so frequently, as agents of food spoilage or pathogens, that effective, rapid, and reliable diagnosis is of great importance.

The most important microorganisms which cause food spoilage are *Clostridium botulinum*, the cause of botulism; *Campylobacter jejuni*; *Clostridium perfringens*; *Cryptosporidium parvum*, enteropathogenic strains of *Escherichia coli*; *Shigella*; *Listeria monocytogenes*; *Salmonella species*; *Staphylococcus aureus*; *Vibrio vulnificus*; and *Yersinia enterolytica*. The General Accounting Office (GAO) reported in 1996 that from 6.5 to 81 million cases of food poisoning occur in the USA every year. The US Food and Drug Administration (FDA) estimates that 2–3% of all food poisonings lead to chronic secondary diseases. It is also estimated that 2–4 million cases of sickness in the US are caused by more than 2000 strains of *Salmonella*. Those horrifying statistics could be extended to other food spoilage organisms. Food poisonings do not just cause human suffering, though, with death in extreme cases, but also substantial economic damage, which is estimated at 5.6–9.4 billion dollars for the US in 1991, for instance.

It is generally known that microorganisms, as agents of infection, present great danger. Their potential can hardly be estimated. For instance, the World Health Report from the WHO indicates statistical orders of magnitude. In 1998, for instance, pathogens, including parasites, were responsible for 9.8 million deaths (not counting prenatal or postnatal infections). That amounts to 18.2% of all deaths due to disease. The dangerous pathogens cannot be summarized as well as the food spoilage organisms, as they are recruited from many phylogenetic branches of the Eubacteria. There is a particularly great "infectious potential" in the Enterobacteria family, in particular.

In combating bacteria pathogenic for humans, identification of the microbes causing a disease or a pathologic symptom is a significant step. Often the proper medical measures can be applied only after the identification. Furthermore, detection methods for bacteria which work well could also be used as preventive tools in food quality assurance.

Classical detection of bacteria consists of microbiological identification, which usually involves isolation on selective media containing agar. This procedure has two significant disadvantages, however. First, the detection is often not reliable or specific. Second, many bacteria require a growth period of at least 18 hours for isolation as colonies. In many cases, a secondary isolation or a secondary detection are also necessary. Everything considered, diagnosis times up to a week are not unusual. In addition to that, there are also pathogenic microbes which cannot be cultured (J. J. Byrd et al., 1991, Appl. Environ. Microbiol. 57, 875–878). In a time of rapid means of transport and global trade in goods, though, rapid diagnostic methods which in the optimal case should not take longer than 24 hours, are essential to prevent the spread of pathogens or world-wide food poisonings from just a single local source.

Various procedures have been developed in recent years to meet modern requirements. They are intended to provide rapid and reliable routine identification of microbes. For example, immunologic methods utilize the specific binding of monoclonal or polyclonal antibodies to bacterial surface antigens. Such procedures are used particularly for serotyping for *Salmonella*, for instance. In general, to be sure, detection by ELISA is relatively rapid, but it requires processing and isolation of the specific antigens, and that can have many problems. Bacterial detection methods utilizing DNA probes have proven to be particularly capable because they are very sensitive, relatively specific, and can be used to detect microorganisms in a total experimental period of 2–3 days.

BACKGROUND OF THE INVENTION

The invention consists in providing specific DNA sequences and selecting DNA regions which are particularly suitable for detecting bacteria. Thus this application is based on the identification of organisms by their genetic information. Using deviations of as little as a single component in the nucleotide sequence in certain DNA regions it is already possible to differentiate species.

Historically considered, ribosomal RNA genes have already been used for phylogenetic classification of organisms. Comparisons of sequences of the 5 S and 16 S ribosomal genes in different bacteria have led to significant corrections in assignments of relatedness and to discovery of the kingdom of the Archaebacteria. Because of its size and the corresponding high sequencing effort, 23 S RNA has only in recent years been used for systematic classifications.

Direct sequencing of genes of microorganisms to be identified was too expensive and time-consuming in practical use. In the 1980s, therefore, specific nucleotide probes were used to detect bacteria. While those can show very good specificity, the detection limit is often too low. The probe technology was substantially improved by combination with amplification techniques, which reproduce the nucleotide sequence to be detected and thus substantially increase the sensitivity of detection. In an extreme case, it is possible to detect a single isolated genome. In practice, losses occur in isolation of DNA, increasing the detection limit to about $10^2$ to $10^4$ cells.

On the basis of fundamental research, DNA probes from the 5 S, 16 S and 23 S genes were utilized for practical applications. For instance, one should note these patents: Nietupski et al. (U.S. Pat. No. 5,147,778) for detection of *Salmonella*; Mann and Wood (U.S. Pat. No. 6,554,144) for detection of *Yersinia* species; Leong (EP 04 79 117 A1) for detection of various Gram negative and Gram positive bacteria; Carico et al. (EP 1 33 671 B1) for detection of various enterobacterial species; Shah et al. (EP 03 39 783 B1) for detection of *Yersinia enterolytica*; Carrico (EP 01 63 220 B1) for detection of *Escherichia coli*; Hogan et al. (WO 88/03957) for detection of species of *Enterobacteria, Mycobacterium, Mycoplasma* and *Legionella*; Leiser et al. (WO 97/41253) for detection of various microorganisms; Grosz and Jensen (WO 95/33854) for detection of *Salmonella enterica*; Stackebrandt and Curiaie (EP 03 14 294 A2) for detection of *Listeria monocytogenes*; Wolff et al. (EP 04 08 077 A2), Hogan and Hammond (U.S. Pat. No. 5,681,698) for detection of *Mycobacterium kansasii*; Hogan et al. (U.S. Pat. No. 5,679,520) for detection of various bacteria; Kohne (U.S. Pat. No. 5,567,587) particularly for detection of bacterial RNA; Kohne (U.S. Pat. No. 5,714,324) for detection of various bacteria; Pelletier (WO 94/28174) for detection of *Legionella*; and Kohne (U.S. Pat. No. 5,601,984) for detection of various bacteria. Most of the patents relate to the sequence of the 16 S rDNA gene, and many also relate to the 23 S rDNA.

It appeared, though, that the latter genes are not suitable for many differentiation operations in practical use because they are too strongly conserved. Closely related microorganisms in particular cannot be differentiated. On the other hand, the 5 S rDNA gene is generally too variable and its differentiation potential is too low for practical use, even though it was initially used for phylogenetic studies in basic research because of its small size.

As the 5 S, 16 S and 23 S rDNA genes have many disadvantages as diagnostic aids, DNA regions which could be used for identification of all eubacteria were sought. Such a DNA region should have very variable and, at the same time, strongly conserved sequences. Then the variable regions would be useful to differentiate closely related species, such as strains and species. The conserved sequences would be used to detect more distantly related bacteria or higher taxonomic units.

In the very recent past, the 16 S–23 S transcribed spacer has been discussed in the literature in the context of extensive studies on ribosomal operons. Their applicability in systematic bacteriology has been questioned, though. For example, Nagpal et al. (J. Microbiol. Meth. 33, 1998, p. 212) considered the utility of these spacers very critically: A major problem with this transcribed rDNA spacer is that it frequently contains tRNA insertions. Such insertions represent dramatic changes in the sequences, and do not necessarily have a relation to phylogenetic separations. However, they have been used in the past to utilize the length polymorphism which they cause as a phylogenetic characteristic (Jensen et al. 1993, Appl. Envir. Microb. 59, 945–952; Jensen, WO 93/11264; Kur et al. 1995, Acta Microb. Pol. 44, 111–117).

The transcribed spacer between the 23 S and 5 S rDNA is an alternative target sequence for identification of bacteria. For instance, Zhu et al. (J. Appl. Bacteriol. 80, 1996, 244–251) published detection of *Salmonella typhi* using this diagnostic DNA region. However, the general utility of this spacer for detecting other bacteria cannot be derived from that work. There are very many examples which indicate that a DNA region is suitable only for identifying one or a few species of bacteria. Individual patents imply a potential but very limited applicability of the 23 S–5 S transcribed DNA region for bacterial diagnosis. Those all have in common that their applicability is limited to just a single bacterial species, specifically, to detection of *Legionella* (Heidrich et al., EP 07 39 988 A1), *Pseudomonas aeruginosa* (Berghof et al., DE 197 39 611 A1) and *Staphylococcus aureus* (Berghof et al., WO 99/05159).

The technical problem underlying the present invention consists in providing materials and processes which allow to detect any desired bacterium (preferably from the Enterobacteria group) in a material being examined.

This problem is solved according to the invention by a nucleic acid molecule as a probe and/or a primer for detection of bacteria, selected from
  a) a nucleic acid comprising at least one sequence with any of the SEQ ID NOs: 1 to 530 and/or a sequence from position 2667 to 2720, 2727 to 2776, 2777 to 2801, 2801 to 2832, 2857 to 2896, 2907 to 2931, 2983 to 2999, and/or 3000 to 3032 according to SEQ ID NO: 1; or nucleic acids homologous with them;
  b) a nucleic acid which hybridizes specifically with a nucleic acid according to a);
  c) a nucleic acid which exhibits 70%, and preferably at least 90%, identity with a nucleic acid according to a) or b);
  d) a nucleic acid which is complementary to a nucleic acid according to any of a) to c);
  and/or
  combinations of the nucleic acids according to any of a) to d), except for the SEQ ID NO:1.

Further claims concern preferred embodiments.

In one particularly preferred embodiment, the presence of Enterobacteria in a sample being analyzed is shown by the analysis sample being brought into contact with a probe which detects the presence of a nucleic acid from the 23 S/5 S rDNA genome segment of the Enterobacteria.

The sequence specified as NO: 1 in claim 1 is derived from *E. coli*. Homologous DNA sequences are those derived from bacteria other than the *E. coli* sequence shown, but in which the genome segment from the other bacteria corresponds to the sequence based on SEQ ID NO:1. For more details, we refer to the definition of homologous DNA sequences, below.

The nucleic acid molecule according to the invention comprises preferably at least 10 nucleotides, and especially preferably at least 14 nucleotides. Nucleic acid molecules of these lengths are used preferably as primers, while nucleic acids used as probes preferably comprise at least 50 nucleotides.

In another preferred embodiment, nucleotides of the probe or the primer can be replaced by modified nucleotides containing, for instance, attached groups which ultimately are used for a detection reaction. Particularly preferred derivatizations are specified in claim 4.

In another preferred embodiment, combinations of the specified nucleic acid molecules are used. Selecting the particular combination of nucleic acid molecules allows adjustment of the selectivity of the detection reaction. In doing so, selection of the primer combinations and/or probe combinations can establish the conditions of the detection reactions so that they either demonstrate generally the presence of bacteria in a sample, or specifically indicate the presence of a certain bacterial species.

A kit according to the invention contains at least one nucleic acid according to the invention together with the other usual reagents used for nucleic acid detection. They include, among others, suitable buffers and detection agents such as enzymes with which, for example, biotinylated nucleic acid hybrids which are formed can be detected.

In another preferred embodiment, called Consensus PCR here, the process is carried out according to claim 8. First, a nucleic acid fragment is amplified by use of conserved primers (those hybridize to nucleic acids of different bacterial taxonomic units). Then more specific nucleic acid segments are detected by use of other more specific nucleic acids (these hybridize with only a few taxonomic units or only with a certain species). The latter allow then a conclusion about the presence of a particular genus, type or species in the sample being analyzed.

Various established detection procedures can be employed to detect nucleic acids in the process used. They include Southern Blot techniques, PCR techniques, LCR techniques, etc.

In one broad study, transcribed spacer between 23 S and 5 S rDNA was examined for its general usefulness as a diagnostic target molecule. For this purpose, genomic DNA from very many bacterial strains was isolated, purified, cloned into a vector, sequenced, and finally evaluated in an extensive sequence comparison. Surprisingly, this sequence segment was suitable for identification of almost all bacterial species. With the encouragement of that finding, the analyses were extended to the adjacent regions of the spacer. All in all, DNA fragments from all bacterial classes or smaller phylogenetic units were examined. They have lengths of 400–750 base pairs and include the end, i.e., the last 330–430 nucleotides (depending on the species) of the 23 S rDNA gene, the transcribed spacer, and the complete 5 S rDNA gene. The total size of the fragments is 400–750 base pairs. The experiments showed that the 23 S rDNA gene and the 5 S rDNA gene are adjacent in almost all bacterial species. This information is an important prerequisite for use and applicability of this invention.

This invention is particularly based on the fact that a DNA region which can contain significant portions of at least two adjacent genes is selected for detection of microorganisms. In practice, the usefulness of the region is determined particularly by its phylogenetic variability. There can be quite contrary requirements, depending on whether distantly related bacteria, taxonomic units, or strains of a species are to be detected. Now the frequency of occurrence of both variable and conserved regions is greater for two genes than for one, as the example of the 23 S–5 S tandem shows. Thus the use of two adjacent genes, including the variable intercalated sequences is a substantial advantage.

Figure 2:
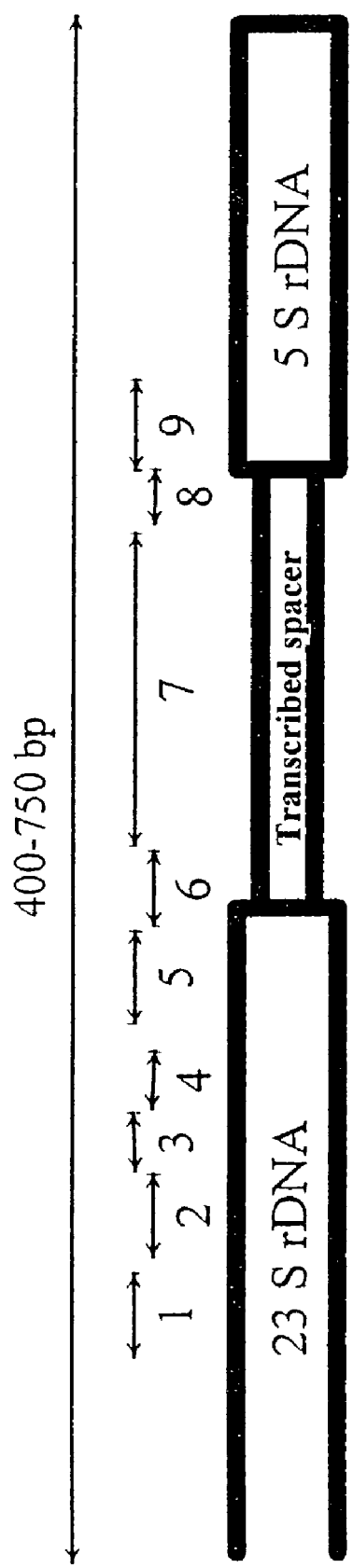
Figure 3:
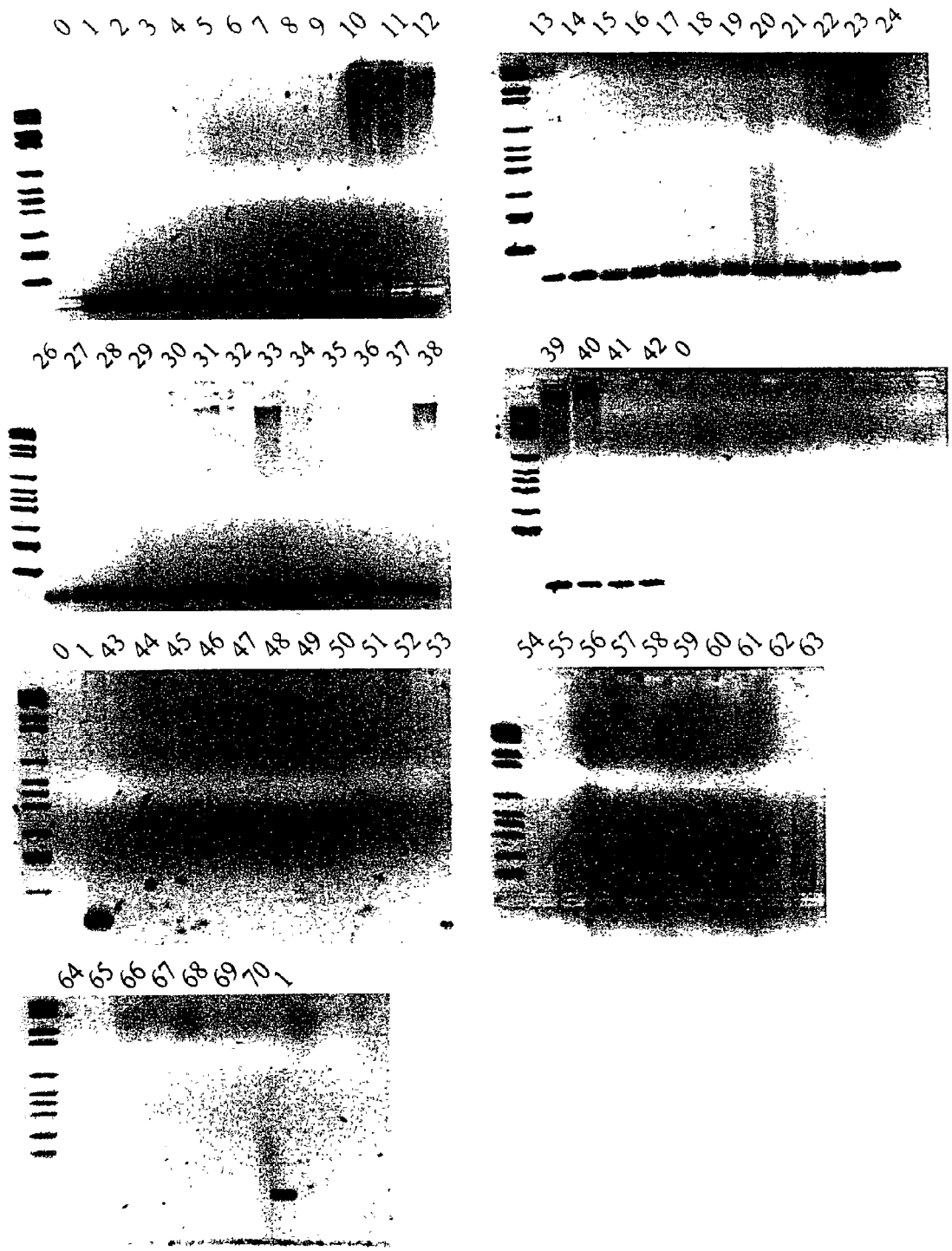
Figure 4:
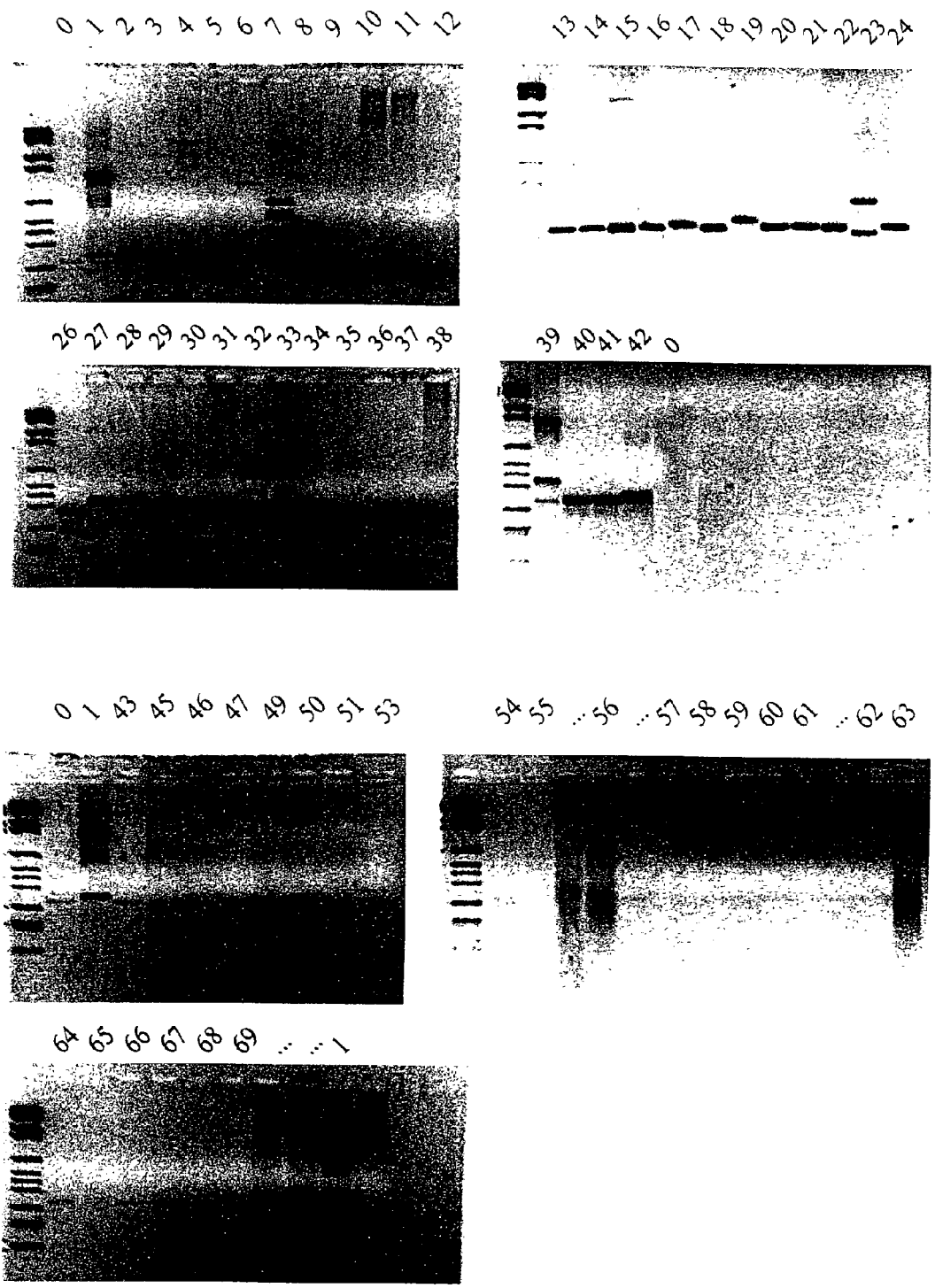
Figure 5:
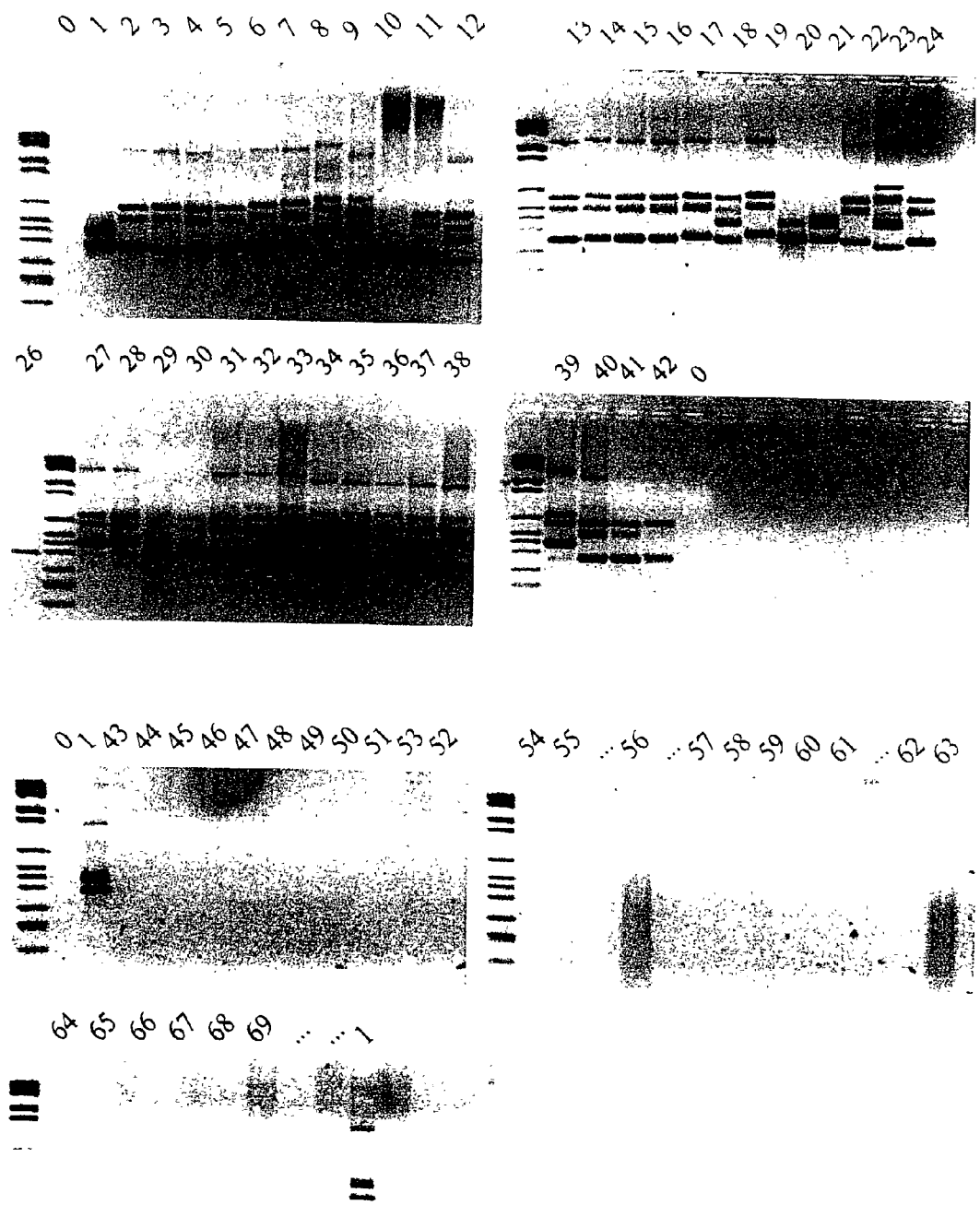
Figure 6:
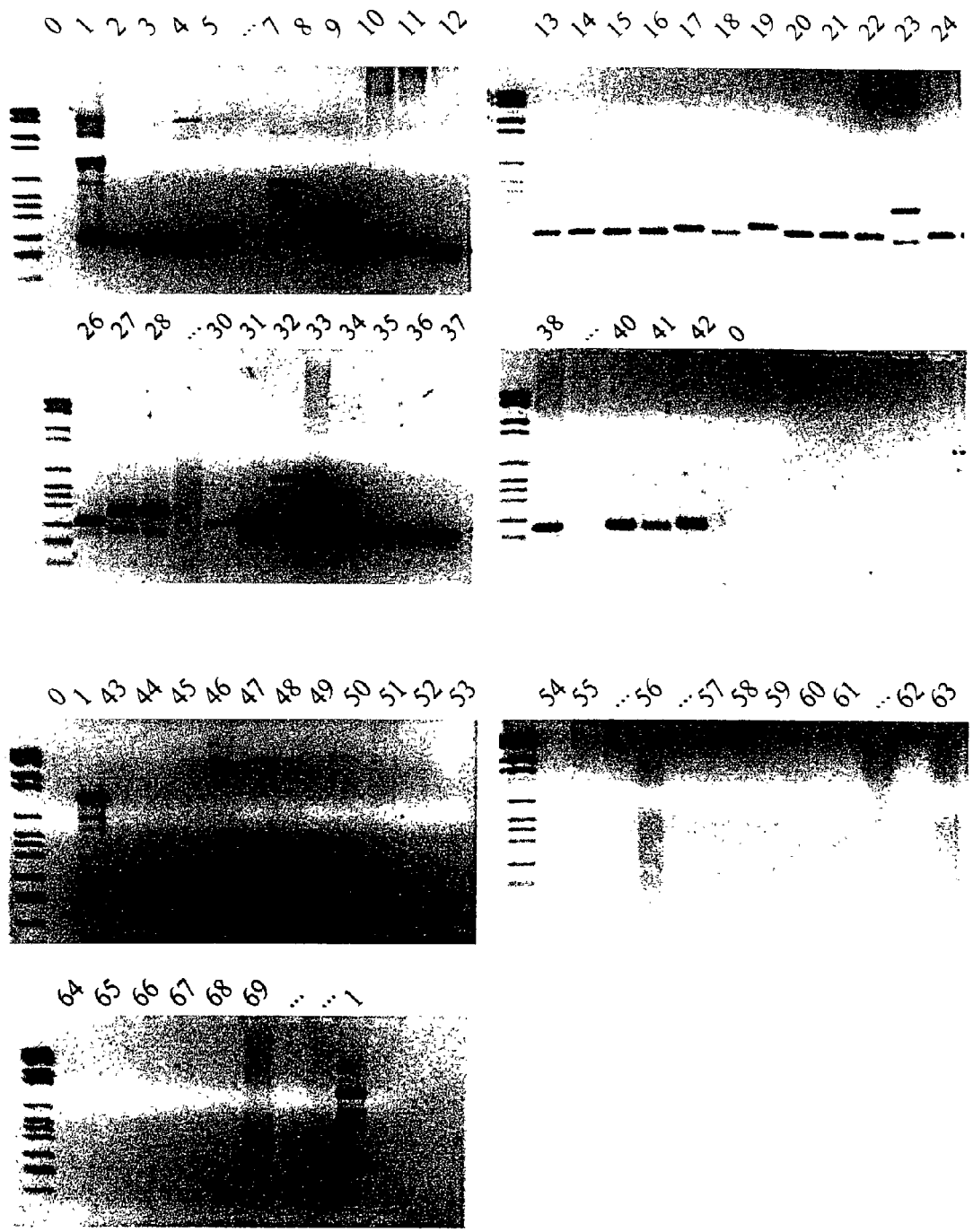
Figure 7:
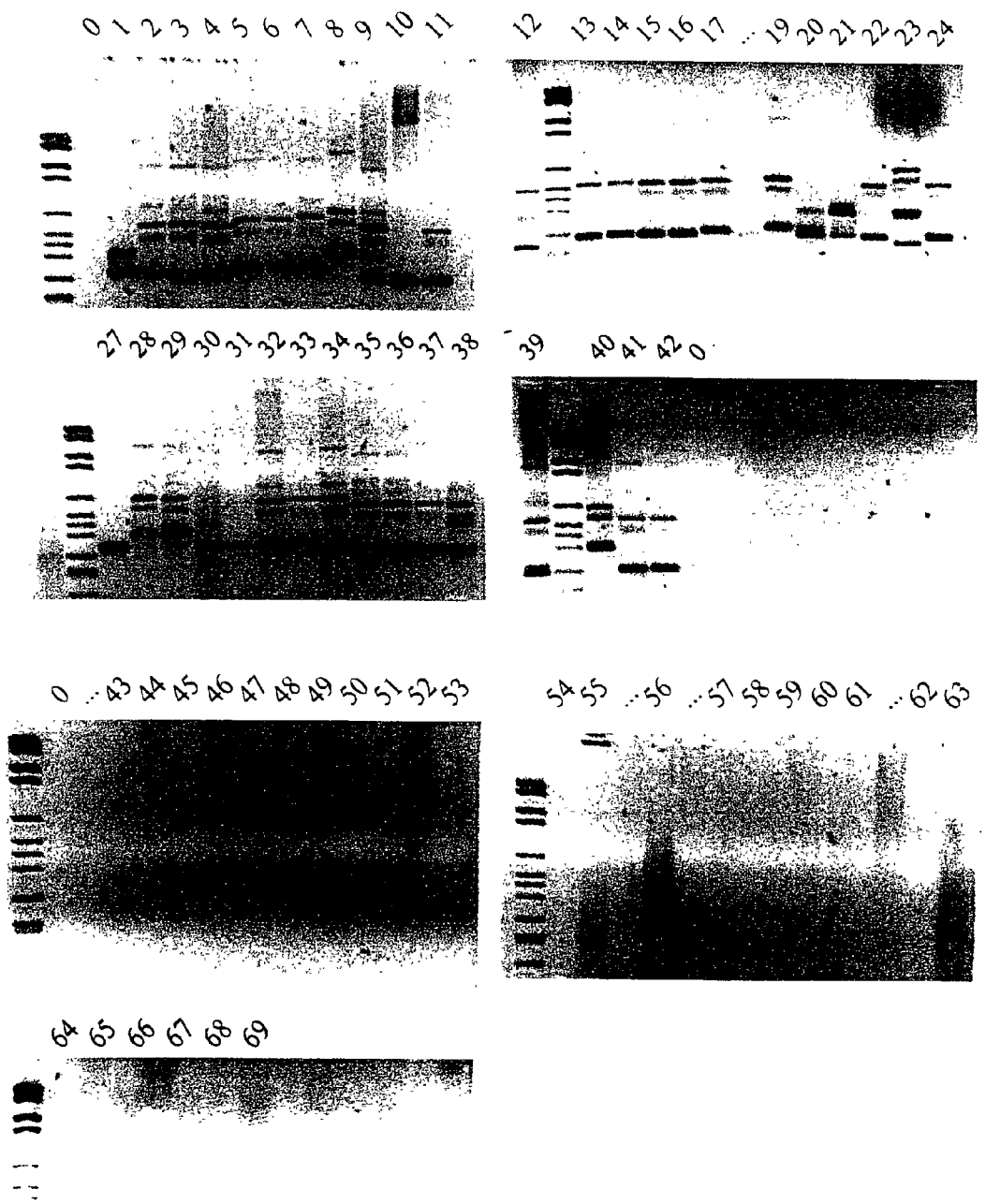

It was also found that the end of the 23 S rDNA gene, the 5 S rDNA gene, and the transcribed spacer between them contain nucleotide sequences which cover a wide range from very variable to very conserved. A fine analysis of this region provided further very interesting conclusions about the differentiation potential of various phylogenetic bacterial units (FIG. 2, Table 6). Nearly all taxonomic units can be detected and/or differentiated by using subregions. More or less variable regions are shown in FIG. 2 with the sections 1–9, while the strongly conserved regions are intercalated between and adjacent to them. The latter are thus particularly suitable for detecting higher taxonomic units, such as the whole Eubacteria or classes or divisions of them.

The phylogenetic dendrogram in FIG. 1 provides another indication of the usefulness of the region. It can be seen that the 23 S rDNA–5 S rDNA region allows very good differentiation with respect to coarse classification, as members of the Proteobacteria are assigned to 1–2 groups, while the Firmicutes are separated. Furthermore, the lengths of the branches, even for closely related species, indicates that they can be distinguished well from each other. Here a phylogenetically correct assignment of close relatives in the dendrogram is quite undesirable, because then they would lie in a closely connected coherent group and perhaps could not be distinguished as easily from one another.

DETAILED DESCRIPTION OF THE FIGURES

FIG. 1: Phylogenetic dendrogram of some bacteria detected in this work. It can be seen that the Proteobacteria and the Firmicutes form branches which can be separated.

FIG. 2: Schematic representation of the ribosomal region described herein comprising the terminal region of the 23 S rDNA, the transcribed spacer, and the 5 S rDNA. This region, or parts of it, is used to detect bacteria. Table 6 shows a detailed characterization of individual domains.

FIGS. 3–7: Detection of enterobacteria by PCR. The figures show gels stained with ethidium bromide. The presence of bands is characteristic of the presence of Enterobacteria. The upper halves of the figures show positive findings, while the lower halves show the negative controls. Table 7 summarizes the use of the primer. A mixture of Bgl 1 and Hinf 1 of restriction-digested BR328 plasmid DNA (Boehringer Mannheim) was used as the DNA size standard.

The DNA size markers include the restriction fragment sizes 154, 220, 234, 298, 394, 453, 517, 653, 1033, 1230, 1766 and 2176 base pairs.

Figure 8:
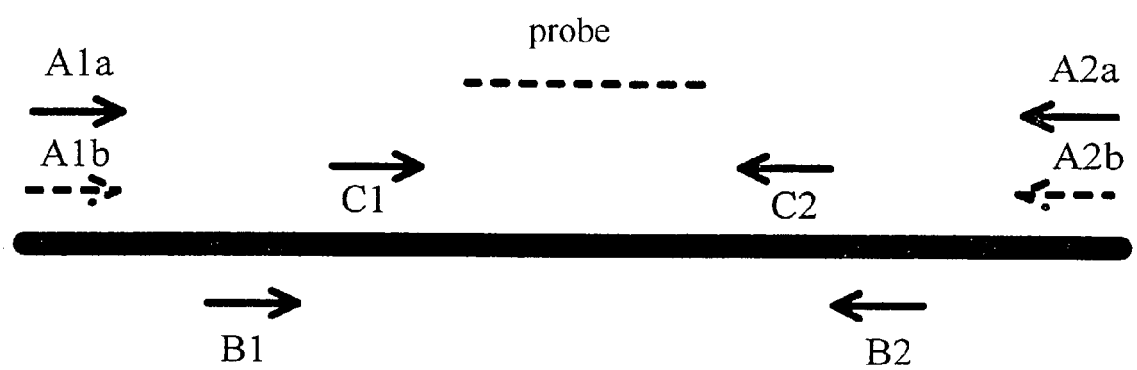

FIG. 8: Plan of a consensus PCR. Conserved primers are arranged peripherally, and less-conserved primers are nested internally. In a first step, consensus PCR allows amplification of DNA with high taxonomic breadth, in the extreme case of all bacterial species. In the subsequent steps, there can be further rounds of amplification. They may be performed in separate vessels, with primers specific for smaller taxonomic units. In the final step, probes can be used which likewise contribute to the specificity of the detection and which can also aid observation of the detection, such as with dyes. Here, and in this figure, the following nomenclature is used: Primer A: the most conserved primers, and the ones with the most peripheral positions in the detection system; Primer [A, B, C . . . ]: the sequence of primers in the nesting as shown above; Primer [capital letter]1: forward primer; Primer [capital letter]2: reverse primer; Primer [capital letter][number][lower-case letter]: the lower-case letters characterize similar primers, or primers which hybridize at homologous or comparable positions within a target DNA. The probe is preferably in the central, highly variable, region if species or strains are to be detected.

EXAMPLE 1

Detection of the Enterobacteriaceae Family

Genomic DNA was isolated, using standard procedures which are themselves known, from pure cultures of the bacteria listed in Table 1. Quantities of about 1 to 100 ng from each of these preparations were used in PCRs. The reaction solution had the following composition:

| | |
|---|---|
| genomic DNA | 1 µl |
| H$_2$O | 19.8 µl |
| Buffer (10×)[*1] | 2.5 µl |
| dNTP (10 mM)[*2] | 0.25 µl |
| forward primer (10 µM)[*3] | 0.20 µl |
| reverse primer (10 µM)[*3] | 0.20 µl |
| MgCl$_2$ | 0.75 µl |
| Taq polymerase (5 U/µl)[*1] | 0.3 µl |

[*1]Buffer and enzyme from Biomaster or any other source.
[*2]Nucleotides from Boehringer Mannheim or any other source.
[*3]Equimolar quantities of primers.
In the case of mixtures, each forward and reverse primer has a total final concentration of 10 µM.

The PCR was done in a Perkin Elmer 9600 Thermocycler with the thermal profile shown below:

| | | |
|---|---|---|
| initial denaturation | 95° C. | 5 minutes |
| amplification (35 cycles) | 92° C. | 1 minute |
| | 62° C. | 1 minute |
| | 72° C. | 30 seconds |
| final synthesis | 72° C. | 5 minutes |

The species listed in Table 1 were tested for identification of the Enterobacteriaceae family. The primer combinations used and the primer-specific parameters are listed in Table 7. When more than one forward or reverse primer is listed in Table 7, it indicates use of that mixture.

The result of the PCR was analyzed by agarose gel electrophoresis and staining with ethidium bromide. The presence of PCR products indicates the presence of enterobacteria.

The synthesized PCR products are mostly of sizes on the order of 400 to 750 base pairs. Many bands can occur throughout, because ribosomal alleles are heterogeneous in many bacterial species. Table 1 shows the results obtained. They show that the enterobacteria are completely delimited from representatives of other taxa.

EXAMPLE 2

Detection of a Bacterial Species, with *Pantoea Dispersa* as an Example

Genomic DNA can be isolated from pure cultures of bacteria by standard procedures which are themselves known. Quantities of about 1 to 100 ng each from these preparations can be used in a PCR. The reaction solution can then have the following composition:

| | |
|---|---|
| genomic DNA | 1 µl |
| H$_2$O | 19.8 µl |
| Buffer (10×)[*1] | 2.5 µl |
| dNTP (10 mM)[*2] | 0.25 µl |
| forward primer A (10 µM)[*3] | 0.20 µl |
| reverse primer (10 µM)[*3] | 0.20 µl |
| MgCl$_2$ | 0.75 µl |
| Taq polymerase (5 U/µl)[*1] | 0.3 µl |

[*1]Buffer and enzyme from Biomaster.
[*2]Nucleotides from Boehringer Mannheim or any other source.
[*3]Equimolar quantities of primers.
In the case of mixtures, each forward and reverse primer has a total final concentration of 10 µM.

The primer combinations SEQ ID 2+primer x1, SEQ ID (3–6)+primer x1, or the sequence complementary to primer x1+the sequence complementary to SEQ ID 147 can be used to detect *Pantoea dispersa*. Here primer x1 is equivalent to the nucleotide CGTTGCCCCGCTCGCGCCGCTCAGT-CAC. Primer x1 is a partial sequence from SEQ ID 108.

The PCR can be done in a Perkin Elmer Thermocycler with the thermoprofile shown below:

| | | |
|---|---|---|
| initial denaturation | 95° C. | 5 minutes |
| amplification (35 cycles) | 92° C. | 1 minute |
| | 62° C. | 1 minute |
| | 72° C. | 20 seconds |
| final synthesis | 72° C. | 5 minutes |

The result of the PCR can be made visible by agarose gel electrophoresis and staining with ethidium bromide. The synthesized PCR products have sizes on the order of 370, 320 and 70 base pairs. The absence of amplificates indicates absence of genomic DNA from *Pantoea dispersa*. This experimental system can give the results summarized in Table 2.

EXAMPLE 3

Use of a Consensus PCR in Chip Technology

3a) Principle of Consensus PCR

In a consensus PCR, such as is shown schematically in FIG. 8, at least two "consensus primers" (A1, A2) are used, which can detect DNA from at least two taxonomic units. Those units can be strains, species, or even higher taxonomic units such as kingdoms or classes. In the detection system, the amplified taxonomic units are subsequently differentiated, in at least a second detection step, using another PCR and/or with probes. The PCR primers (B1, B2) of the second, or subsequent, amplification step are each chosen so that they are within the amplification product and have the potential to detect a specific taxonomic unit. By use of more primers (C, D, E . . . ), a pool of many taxonomic units can, if necessary, be narrowed down simultaneously. Furthermore, the detection potential can be extended to more taxonomic units in a multiplex mixture (such as A1a, A1b, A1c . . . ). The latter case exists if individual nucleotides in a primer differ or if the primers are completely different. The nomenclature of the consensus primers can also be found in the legend for FIG. 8.

Amplification products can be identified by means of the primers. The detection is positive if the primers recognize the target DNA and successfully amplify it. In addition probes can provide a specific detection. They hybridize specifically to the amplified DNA and allow a certain DNA sequence to be detected by direct or indirect coupling to dyes. Everything considered, probes can be used in many technical embodiments known to those skilled in the art. For example, there are Southern Blotting, the lightcycler technology with fluorescent probes, or the chip technology, in which arbitrarily many probes are arranged in a microarray.

It is particularly advantageous for success of a consensus PCR that the primers become increasingly specific in the order A, B, C . . . . That can be assured by selection of the DNA target region as shown in FIG. 2.

Consensus PCR has the advantage that it allows simultaneous detection of more than two taxonomic units from just a single nucleic acid sample, which can be correspondingly small. The number of detectable microorganisms can be increased in various ways. For instance, the detection potential of a consensus system increases with the number of primer species A, B, C, or A1a, A1b, A1c, . . . as they are defined in FIG. 8. In addition, a PCR solution can, after an initial process with a primer pair A1, A2, be separated and amplified in separate solutions with additional primer pairs B1a+B2a on the one hand and B1b+B2b on the other hand. Finally, the identity of PCR amplificates can be determined by hybridizing with probes.

3b) Example of Detection a Group of Genera of the Enterobacteria.

Genomic DNA can be isolated from pure cultures of bacteria by standard procedures which are themselves known. Quantities of about 1 to 100 ng each from these preparations can be used in a PCR. The reaction solution can have the following composition:

| | |
|---|---|
| genomic DNA | 1 µl |
| H$_2$O | 19.8 µl |
| Buffer (10×)*[1] | 2.5 µl |
| dNTP (10 mM)*[2] | 0.25 µl |
| forward primer A (10 µM)*[3] | 0.20 µl |
| reverse primer (10 µM)*[3] | 0.20 µl |
| MgCl$_2$ | 0.75 µl |
| Taq polymerase (5 U/µl)*[1] | 0.3 µl |

*[1]Buffer and enzyme from Biomaster.
*[2]Nucleotides from Boehringer Mannheim or any other source.
*[3]Equimolar quantities of primers.
In the case of mixtures, each forward and reverse primer has a total final concentration of 10 µM.

As chip technology generally uses very small reaction volumes, the reaction solution shown above can be made smaller with the concentrations remaining constant. It may be necessary to adjust the PCR cycle times. A ribosomal DNA fragment can be amplified initially for consensus PCR. That process can be specific for larger taxonomic units, as described in Example 1, with use of the primers described there. Alternatively, a ribosomal DNA fragment from all bacteria can be amplified. For instance, use of the primer combination SEQ ID 211+SEQ ID 212 provides ribosomal DNA of a very broad taxonomic spectrum of bacteria.

The amplified DNA is denatured by standard procedures, thus being converted into single-strand DNA. This form is able to bind to a DNA, RNA, or PNA probe. Then the hybridization of the amplificate is detected with the probe, depending on the design of the chip. Alternatively, detection can be done with an ELISA. The composition of the probe is such that it provides the specificity to meet the requirements. Accordingly, strains, genera, or larger taxonomic units can be detected.

Table 3 shows an example of detection of a group of genera of the family of the enterobacteria using the probe GTTCCGAGATTGGTT as a subsequence of SEQ ID 164. Such a group detection is particularly practical in chip technology if various group detections intersect with each other. Then an individual species, or groups of species, such as those important for food examinations, can be detected in the intersection.

3c) Use of Consensus PCR to Detect all Bacteria

To detect all bacteria, strongly conserved consensus primers are used in a first round of amplification. Suitable for selecting sequences are regions which are peripheral in the ribosomal segment, as shown in FIG. 2, are. They are consequently homologous to the regions of SEQ ID 1 beginning at position 2571 or ending at position 3112. From this region, for example, the primers SEQ ID 211 (as primer A1a, for instance) and SEQ ID 212 (as primer A2A, for instance) are particularly suitable for general amplification. Other primers (A1b, A1c, . . . , or A2b, A2c . . . ) which cover an arbitrarily large taxonomic range of the Eubacteria in a multiplex PCR can also be derived easily. In this nomenclature, primers A1 and A2 are primer pairs; B and C . . . are nested primers; and A1a and A1b are homologous or similar primers.

An initial differentiation can be accomplished by using nested primers (B, C, D . . . ). That can also be supported by dividing the primary PCR solution so that one primer pair B or C or D, etc., is used in each separate PCR solution. This nesting is particularly advantageous because the ribosomal region as shown in FIG. 8 increases in variability from the outside to the inside, as is also described in Table 6.

Then it is preferable to use probes for final differentiation and identification. For instance, if species or strains are to be detected, then the probe should hybridize centrally in region 7 as shown in FIG. 2.

Table 8 presents many polynucleotides for detection of genera and species or strains in a consensus PCR. Use of primer number 1 from Table 8 has already been described extensively in Example 1.

The properties of the polynucleotides follow their characterization from Table 6 or FIG. 2. That means that primer A1 can be assigned to region 1 of Table 6 or FIG. 2; primer A2 can be assigned to region 2 . . . ; primer B2 can be assigned to region 8, and primer A2 to region 9. According to this concept, primers A1–G1 from Table 8 can be used as forward primers, while primers B2 and A2 can be used as reverse primers. For that purpose, the sequences for the two latter primer types must be converted (Exception No. 1, Table 8). The "H1 primers" in particular can be used as genus-specific or species-specific probes.

The plan for a consensus PCR described here is not absolutely necessary for successful detection. In principle, the polynucleotides listed in Table 8 can be used in any arbitrary combination. In practice, one must first decide which bacteria are to be excluded from the detection as "undesired". Then a simpler PCR version that differs from the plan shown can be selected, depending on the objective. The simplest form of consensus PCR, then, consists of just two primers corresponding to the sequences from Table 8, or sequences complementary to them.

Many of the conserved primers listed in Table 8 have the potential to detect the DNA of higher taxonomic units, such as classes, phyla, or families. As can be seen from Table 6, that applies particularly to the peripheral primer A or homologous sequences of SEQ ID 211+SEQ ID 212. Table 8 shows a broader potential for detecting one or more genera or species, particularly due to the redundant enumeration of the sequences. If only one sequence is explicitly listed for a genus, then two primers from that sequence can be selected for detection. It is also possible to select general primers, such as primer A of related genera, for the bacterial class of concern, and to sketch out a specific sequence, such as "primer h1" for a probe. As long as the sequences are very long, nucleotide fragments at least 15 bases long can be selected from them.

3d) Design of a Consensus PCR for Chip Technology

The actual design of a consensus PCR is determined essentially by the expected number of taxonomic units to be detected. As consensus PCR in its most complex form is also a multiplex PCR, only a limited number of bacteria can be determined in one reaction solution. Experience shows that this number is less than 20. For that reason, it can be advantageous to do different PCR solutions with the same probe and different primers A, B, etc. (nomenclature as shown in FIG. 8).

First, bacteria from natural samples are enriched, or genomic DNA is isolated directly from them by standard procedures which are themselves known. Quantities of about 1 to 100 ng each from these preparations can be used in a PCR. The reaction solution can then have the following composition:

| | |
|---|---|
| genomic DNA | 1 µl |
| H₂O | 19.8 µl |
| Buffer (10×)*¹ | 2.5 µl |
| dNTP (10 mM)*² | 0.25 µl |
| forward primer A (10 µM)*³ | 0.20 µl |
| reverse primer (10 µM)*³ | 0.20 µl |
| MgCl₂ | 0.75 µl |
| Taq polymerase (5 U/µl)*¹ | 0.3 µl |

*¹Buffer and enzyme from Biomaster.
*²Nucleotides from Boehringer Mannheim or any other source.
*³Equimolar quantities of primers. In the case of mixtures, each forward and reverse primer has a total final concentration of 10 µM. For example, primers can be designed and combined as described in 3c.

As very small reaction volumes are generally used in chip technology, the reaction solution above can be reduced in volume with the concentrations kept constant. Adjustment of the PCR cycle times may be necessary.

After the amplification rounds, the DNA is combined. Probes, which, in one specific embodiment, can be selected from the column "Primer H1" of Table 8 are immobilized on a chip. Technological procedures for that are known to those skilled in the art. The combined DNA is diluted 1:1 with denaturation buffer (Example 4) and incubated for one hour at room temperature. Then ten times that volume of hybridization buffer (Example 4) is added and the solution is slowly passed over the chip, i.e., the surface with probes adhering to it, at 37–60° C. After this procedure, the chip surface is washed three times for at least 2 minutes with wash buffer (Example 4) at 37–60° C. Then the detection can be done. Primers coupled to a fluorescent dye can be used for that. The fluorescence can be detected with a detector such as a CCD camera. However, there are various alternative possibilities for detection. For instance, it is also possible to follow and quantify the bonding of the single-stranded amplification products to the probes by surface plasmon resonance (SPR) spectroscopy. The latter method has the advantage that no dye need be used for detection. If SPR is used, it should be designed so that detection occurs simultaneously on the regions of the surface which have the same probes. A particularly advantageous embodiment has many (i.e., more than 100 or 1000) separate detection surfaces arranged on the chip. An increase in the SPR signal, caused by the nucleic acid hybridization on these surfaces, is a positive result. The primers listed in Table 8 can be used in this manner to detect the corresponding bacteria; or, in principle, to detect, and if required to quantify, all bacteria.

EXAMPLE 4

Detection of Microorganisms with Probes

Probes, being polynucleotides, i.e., DNA, RNA, PNA, or a similar embodiment known to those skilled in the art, are basically suitable for carrying out concentration and detection of DNA or RNA. They occur as single-stranded molecules, or they are converted to the single-stranded form by denaturation, such as by heating or by sodium hydroxide, according to published standard procedures.

To detect microorganisms, the DNA or RNA must be isolated from them and perhaps purified. Various measures can provide high efficiency in the nucleic acid yield:
1) The microorganisms can be concentrated by physical methods, such as with antibodies coupled to magnetic particles, or by centrifuging.
2) The DNA or RNA from the microorganisms can be amplified in a PCR or comparable amplification reaction.
3) The DNA or RNA of the microorganisms, possibly amplified, is concentrated with commercially available material in the course of purification.

Improvement in the efficiency of nucleic acid yields, particularly through amplification, can itself contribute significantly to the specificity of bacterial detection.

This is followed by an incubation step, in which the probes form a hybrid molecule with the nucleic acids to be detected (if the microorganisms to be detected were present). The hybrid molecules are formed under controlled conditions. Then washing steps with buffers follow under conditions (pH, temperature, ionic strength) which allow specific hybridization of nucleic acids while less specific and undesired hybrid molecules dissociate.

Finally the hybrid molecules are detected. There are numerous procedures for detection, which are known in detail to those skilled in the art. Dyes, possibly fluorescent dyes, are used, which are coupled directly or indirectly to the probes or to the DNA being detected, or are incorporated into them. In particular, that can also happen in chip technology or in lightcycler technology. There are also other physical procedures, such as attenuated total reflection of light at interfaces with two different densities, which can be used in detection of hybrid molecules.

Evaluation of the detection can be done in various ways. In an "all or nothing" detection, the hybrid molecule can be detected only if the microorganism being sought were present. That is, if the previously mentioned amplification reaction with the nucleic acids of the microorganisms did not cause any multiplication of the amino acids, then no hybrid molecules will be detectable. However, if "undesired" nucleic acids were amplified, or if they had been present in large quantity, those nucleic acids can be excluded by the stringency conditions in hybridization. Also, quantification of the hybrid molecules allows fine tuning of the specificity of the detection, by establishing a limit for positive detection.

All the nucleic acids specified in this patent are basically usable as probes. In particular, Table 3 lists an extract of possible probes. The nucleic acids provide detection of the genera specified in the table, and distinction from all other genera of the Eubacteria.

Examples are presented in the following of how the DNA regions specified for this purpose can be used as probes to detect microorganisms. An ELISA detection procedure is used in this example. In that procedure, nucleic acids are detected by an enzymatic reaction which proceeds in microtiter plates.

In this example, the DNA is first amplified in a PCR reaction. That reaction employs primers coupled with digoxigenin. Then a microtiter plate coated with streptavidin is loaded with a biotin-labeled probe, so that the probes couple to the plate surface. The PCR amplificates, denatured by base, hybridize with the probes in a 30-minute reaction. The end of the amplificate that is labeled with 5'dioxigenin now acts as the antigen for a specific antibody which is, in turn, coupled to the enzyme peroxidase. After addition of tetramethylbenzidine, a blue dye forms. Formation of the dye is stopped with 0.5 M sulfuric acid. At the same time, the color turns yellow because of the pH change. The intensity of the absorption is measured at 450 nm in an ELISA reader.

The following reagents are used to perform the ELISA:

| Hybridization buffer (2.5 × SSC) | |
|---|---|
| 2.5 × SSC | 62.5 ml of 20 × SSC (see below) |
| 2 × Denhardts | 20 ml of 50 × Denhardts (see below) |
| 10 mM Tris (Gibco, No. 15504-038) | 5 ml of 1M Tris |
| 1 mM EDTA (Fluka, No. 03699) | 1 ml of 0.5M EDTA |
| Make up to 0.5 liter with double-distilled water and adjust to pH 7.5. | |
| Wash buffer 1 | |
| 1 × SSC | 50 ml of 20 × SSC (see below) |
| 2 × Denhardts | 40 ml of 50 × Denhardts (see below) |
| 10 mM Tris (Gibco, No. 15504-038) | 10 ml of 1M Tris |
| 1 mM EDTA (Fluka, No. 03699) | 2 ml of 0.5M EDTA |
| Make up to 1 liter with double-distilled water and adjust to pH 7.5. | |
| Wash buffer 2 | |
| 100 mM Tris (Gibco, No. 15504-038) | 12.15 g |
| 150 mM NaCl (Merck, No. 6404.5000) | 8.78 g |
| 0.05% Tween 20 (Serva, No. 37470) | 0.5 g |
| 0.5% blocking reagent (Boehringer) | Dissolve 5 g in D1 (see below) at 60° C. |
| 10 μg/ml herring sperm | 10 ml of the 10 mg/ml stock solution |
| Dilute to 1 liter with double-distilled water and adjust to pH 7.5 | |
| Denaturation buffer | |
| 125 mM NaOH (Fluka, No. 71690) | 0.5 g |
| 20 mM EDTA (Fluka, No. 03699) | 0.745 g |
| Make up to 0.1 liter with double-distilled water. | |

-continued

Coupling buffer

| | |
|---|---|
| 10 mM Tris (Gibco, No. 15504-038) | 10 ml of 1M Tris |
| 1 mM EDTA (Fluka, No. 03699) | 2 ml of 0.5M EDTA |
| 100 mM NaCl (Merck, No. 6404.5000) | 5.88 g |
| 0.15% Triton X 100 (Chemical storeroom) | 15 ml |

Make up to 1 liter with double-distilled water and adjust to pH 7.5.
Stop reagent (0.5M $H_2SO_4$)

| | |
|---|---|
| 95% $H_2SO_4$ | 14 ml |

Make up to 0.5 liter with double-distilled water.
50 × Denhardts

| | |
|---|---|
| Ficoll 400 (Pharmacia Biotech, No. 17-0400-01) | 5 g |
| Polyvinylpyrrolidone (Sigma, No. P-2307) | 5 g |
| Bovine serum albumin | 5 g |

Make up to 0.5 liter with double-distilled water.
20 × SSC

| | |
|---|---|
| NaCl (Merck, No. 106404.1000) | 350.36 g |
| Sodium citrate (trisodium citrate, dihydrate, Fluka No. 71404) | 176.29 g |

Make up to 2 liters with double-distilled water and adjust to pH 7.0.
D 1

| | |
|---|---|
| 100 mM maleic acid (Fluka, No. 63190) | 11.62 g |
| 150 mM NaCl (Merck, No. 106404.1000) | 8.76 g |
| NaOH (Fluka, No. 71690) | ca. 7.5 g |

Make up to 2 liters with double-distilled water and adjust to pH 7.0.

ELISA Procedure:

200 µl binding buffer and 1 µl probe are applied for each well. The microtiter plate is covered with an adhesive film and left to stand for two hours at room temperature. The PCR amplificates to be examined are thawed at room temperature, mixed with the denaturation buffer in the ratio of 1:1, and incubated for 10 minutes at room temperature. Then 10 ml of this probe is placed into the wells, which have been emptied in the meantime. In addition, 100 µl hybridization buffer is added to each well and incubated for 30 minutes at 37–60° C. To wash, the wells are emptied, filled with 200 ml wash buffer 1 which has been preheated to 37–60° C., and incubated for 2 minutes at the same temperature. This washing step is done three times.

After the wash buffer has been carefully removed, the Anti-Dig-POD-antibody (DAKO) is diluted 1:3000 (1 ml in 3 ml wash buffer 2), and 100 ml of this solution is placed into each of the dry wells. This arrangement is incubated in the incubator at 37° C. for 30 minutes.

Then the microtiter plate is washed three times with 200 ml wash buffer 2 per depression. Then 100 ml of the BM Blue dye (Boehringer) is added per well. After 15 minutes the reaction is stopped by addition of 100 ml 0.5 M $H_2SO_4$. The absorbance of the samples is measured in the ELISA reader.

The probes listed in Table 4 can be used to detect the species listed in the procedure described above.

EXAMPLE 5

General Usefulness of the DNA Regions Specified in this Patent for Detecting Bacteria The ribosomal DNA regions specified here are suitable for detecting eubacteria, especially if they are combined with the 23 S–5 S ribosomal spacers. One skilled in the art can rapidly identify bacterial taxonomic units of his choice using the sequences under SEQ ID 1–530 or by focusing on the specified ribosomal DNA region. In the following, one possible way is exemplified which shows the general usefulness of this invention for all eubacterial species.

The path described here comprises essentially 3 steps. In the first step, a ribosomal region comprising approximately the last 330–430 nucleotides of the 23 S gene, the following transcribed spacer, and the ribosomal 5 S gene is amplified. As this region is of variable length in the various eubacterial species, it has a total length of 400 to about 750 nucleotides. If the DNA sequence is not yet known, it can be advantageous to determine it for the species to be detected and for some closely related species from which it must be distinguished. From a sequence comparison, one skilled in the art can easily determine the best oligonucleotides for the desired detection, e.g., serving as a PCR primer or as a probe. In this example, both primers and probes are selected in that manner. Alternatively, the sequences specified here can also be used directly for a wide spectrum of bacteria, especially if the stringency conditions for the PCR and/or for the hybridization are properly selected.

A) Amplification of Ribosomal DNA

The DNA segment to be used can be amplified from genomic bacterial DNA of the proteobacteria and many other bacterial classes with the primers SEQ ID 211 and 212. If other classes present problems in the DNA amplification, use of primers derived from DNA regions corresponding to SEQ ID 211 and 212 will be successful.

Genomic DNA is isolated from pure cultures of the bacteria listed in Table 5 by standard procedures which are themselves known. Quantities of about 1 to 100 ng each from these preparations are used in a PCR. The reaction solution has the following composition:

| | |
|---|---|
| genomic DNA | 1 µl |
| $H_2O$ | 19.8 µl |
| Buffer (10×)*[1] | 2.5 µl |
| dNTP (10 mM)*[2] | 0.25 µl |
| forward primer A (10 µM)*[3] | 0.20 µl |
| reverse primer (10 µM)*[3] | 0.20 µl |
| $MgCl_2$ | 0.75 µl |
| Taq polymerase (5 U/µl)*[1] | 0.3 µl |

*[1]Buffer and enzyme from Biomaster or any other source.
*[2]Nucleotides from Boehringer Mannheim or any other source.
*[3]Equimolar quantities of primers.
In the case of mixtures, each forward and reverse primer has a total final concentration of 10 µM.

The PCR is done in a Perkin Elmer 9600 Thermocycler with the thermoprofile shown below:

| | | |
|---|---|---|
| initial denaturation | 95° C. | 5 minutes |
| amplification (35 cycles) | 92° C. | 1 minute |
| | 52° C. | 1 minute |
| | 72° C. | 30 seconds |
| final synthesis | 72° C. | 5 minutes |

Examples of genomic DNA which can be used for amplification are listed in Table 5.

B) Genus-Specific and Species-Specific Amplification of a Subregion of the Product from A The DNA product amplified in A) can be used directly to detect bacteria, especially if specific probes are used. It can be advantageous to amplify primarily a subregion of this sequence if the process is intended to provide limitation to a smaller systematic unit of the bacteria, such as species, genera or families. At least part of the differentiating ability can then be provided already by the amplification primer. The region amplified in A) provides many subregions with specific differentiation capabilities. One skilled in the art can easily recognize those regions by comparing the sequences of bacteria to be identified with closely related bacteria.

In this example, the beginning of the 23 S–5 S transcribed spacer and the end of it were selected as regions for specific primers. The actual sequences and the origin of the primer are summarized in Table 5. Comparison of the sequences shows that they basically provide a species-specific detection already. The primers for the *Vibrio* species are exceptions, allowing a genus-specific detection. In the forward primers, the sequence CGAAG . . . TTTT is conserved, in particular for enterobacteria, and in the reverse primers the sequence AACAGMTTT is conserved. Now there are two possibilities for expanding the specificity of the primers to genera and groups of genera, of the Enterobacteria, for instance. One is to lower the annealing temperatures in the PCR. The other is to shift the sequences for the forward primers toward the 23 S gene, and those for the reverse primers toward the 5 S gene. The result is primers in which the sequences are less variable by species. The actual design, then, can be directed to the requirements for detection. Here, we provide examples of the species-specific detection with the primers of Table 5 by PCR amplification.

Genomic DNA is isolated from pure cultures of the bacteria listed in Table 5 by standard procedures which are themselves known. Quantities of about 1 to 100 ng each from these preparations are used in a PCR. The reaction solution has the following composition:

| | |
|---|---|
| genomic DNA | 1 µl |
| H₂O | 19.8 µl |
| Buffer (10×)*¹ | 2.5 µl |
| dNTP (10 mM)*² | 0.25 µl |
| forward primer (10 µM)*³ | 0.20 µl |
| reverse primer* (10 µM)*³ | 0.20 µl |
| MgCl₂ | 0.75 µl |
| Taq polymerase (5 U/µl)*¹ | 0.3 µl |

*¹Buffer and enzyme from Biomaster or any other source.
*²Nucleotides from Boehringer Mannheim or any other source.
*³Forward primer A and reverse primers* are listed in Table 5. In the case of mixtures, each forward and reverse primer has a total final concentration of 10 µM. Reverse primers* have the sequence complementary to the reverse primers shown in Table 5.

The PCR is done in a Perkin Elmer 9600 Thermocycler with the thermoprofile shown below:

| | | |
|---|---|---|
| initial denaturation | 95° C. | 5 minutes |
| amplification (35 cycles) | 92° C. | 1 minute |
| | *45–72° C. | 1 minute |
| | 72° C. | 30 seconds |
| final synthesis | 72° C. | 5 minutes |

*The annealing temperature can be determined according to the generally used formulas for PCR primers.

Table 5 shows the result of the amplification, i.e. the species-specific detection of bacteria using the primers of Table 5 leads to identification of the bacteria assigned to those primers in this table. On the other hand, use of more general primers, the design of which was described before, can lead to detection of all enterobacterial genera or to detection of all the genera from the γ branch of the proteobacteria.

C) Making the Detection More Specific by Using Primers or Probes from the 23 S–5 S Ribosomal Spacer.

If DNA of higher taxonomic units was amplified in steps A) and/or B), then further differentiation of the detection can be accomplished by selection of probes. A more variable DNA region, such as a central region of the 23 S–5 S transcribed spacer can be used for species-specific detection. The probes can be integrated into a chip or used in the lightcycler technology or in an ELISA. In the latter case, the ELISA protocol in Example 4 can be used. Then the results of the species-specific detection of bacteria correspond to the selection of the 23 S–5 S transcribed spacer, because it has mostly a species-specific sequence region. When the primers from Table 5 are used, with use of the corresponding spacer (column SEQ ID from Table 5), then the species listed in that table can be identified.

Explanations of Concepts Used:

Derivation of DNA Sequences

A polynucleotide or oligonucleotide to be used for detection of taxonomic units can be found and developed by deriving it from one or more DNA sequences. In the case of multiple DNA sequences, alignment of the sequences, i.e., a comparison, is advantageous. Derived oligonucleotides may be identical to the original sequence. They may also be a consensus of numerous variables. In that case, the nucleotides of the polymer are selected according to the components most frequently used, or prevalent, at a certain position of the sequences analyzed. It is also possible to select variables in a sequence being developed according to the definition given for "nucleotide". The DNA or RNA polymers resulting from these variable sequences are, then, a mixture of molecules exhibiting all the nucleotides allowed at the positions of the variables.

Analogous DNA Sequences:

Analogous DNA sequences have the same function, or a similar location, as a specified sequence, but cannot be traced back to the same phylogenetic origin. One example is the transcribed spacer between 5 S rDNA and 23 SD rDNA, if it exhibits no similarity with a transcribed spacer at the same location which is being compared with it. That is possible because it is often so variable in distantly related organisms that it is no longer possible to establish its phylogenetic evolution or homology. The transcribed spacer above, though, is clearly definable as a DNA sequence and in its function as a transcribed spacer, or in its location, because it begins at the end of the coding region of the 23 S rDNA and ends at the beginning of the 5 S rDNA.

Adjacent Genes:

Genes are adjacent if they are not separated by any other gene or if that is the case for two particular genes for most of the species studied. Separation is said to exist only if there is another gene between two other genes.

Enterobacteria

The Enterobacteria are a family of the γ-branch of the proteobacteria. The concept involves all the taxonomic units of the family, especially the genera *Alterococcus, Aquamonas, Aranicola, Arsenophonus, Brenneria, Budvicia, Cedecea, Calymmatobacterium, Citrobacter, Edwardsiella, Enterobacter, Erwinia, Escherichia, Ewingella, Hafnia, Klebsiella, Kluyvera, Koserella, Leclercia, Moellerella, Morganella, Pantoea, Phlomobacter, Photorhabdus, Plesiomonas, Proteus, Providencia, Rahnella, Salmonella, Serratia, Shigella, Wigglesworthia, Xenorhabdus, Yersinia,* and *Yokenella.*

Eubacteria:

The Eubacteria, along with the Archaebacteria, make up a kingdom of the Prokaryotes. Here "bacteria" and "eubacteria" are used synonymously. The concept includes all the taxonomic units within this kingdom. The Eubacteria include, for instance, the Aquificales, Aquificaceae, *Desulfurobacterium* group, Chlamydiales, Verrumicrobia group, Chlamydiaceae, Simkaniaceae, Waddliaceae, Verrumicrobia, Verrumicrobiales, *Coprothermobacter* group, Cyanobacteria, Chroococcales, Nostocales, Oscillatoriales, Pleurocapsales, Prochlorophytes, Stigonematales, Cytophagales, the green sulfur bacteria group, Bacteroidaceae, Cytophagaceae, Flavobacteriaceae, *Flexibacter* group, *Hymenobacter* group, *Rhodothermus* group, *Saprospira* group, Sphingobacteriaceae, Succinovibrionaceae, green sulfur bacteria, *Fibrobacter, Acidobacterium* group, *Fibrobacter* group, Firmicutes, Actinobacteria, Acidomicrobidae, Actinobacteridae, Coriobacteridae, Rubrobacteridae, Sphaerobacteridae, *Bacillus* group, *Clostridium* group, *Lactobacillus* group, *Streptococcus* group, Clostridiaceae, Haloanaerobiales, *Heliobacterium* group, Mollicutes, *Sporomusa* branch, *Syntrophomonas* group, *Thermoanaerobacter* group, *Flexistipes* group, Fusobacteria, green nonsulfur bacteria, Chloroflexaceae group, Chloroflexaceae, photosynthetic *Flexibacteria, Holophaga* group, *Nitrospira* group, Planctomycetales, Planctomycetaceae, Proteobacteria, purple non-sulfur bacteria, alpha subdivision of the proteobacteria, beta subdivision of the proteobacteria, gamma subdivision of the proteobacteria, delta/epsilon subdivision of the proteobacteria, Spirochetales, Leptospiraceae, Spirochaetaceae, *Synergistes* group, *Thermodesulfobacterium* group, Thermotogales, *Thermus* group or the *Deinococcus* group.

Gene:

The gene comprises the open reading frame or coding region of a DNA. Thus it codes solely for a single protein. The cistron is also a gene, but it, along with other cistrons, is on a mRNA. DNA regions which regulate transcription of the gene, such as promoters, terminators, and enhancers, are also part of the gene. When, in this patent, we speak, in a simplifying manner of the 23 S rDNA gene and the 5 S rDNA gene, this is based on the usual designations. According to our definition, though, the 23 S rDNA gene or the 5 S rDNA gene is not a gene but an independent functional DNA segment, because it does not code for a protein and cannot be subdivided into codons.

Transcribed Spacer:

The transcribed spacer, on which we focus here, lies behind the coding region of the 23 S rDNA gene and before the coding region of the 5 S rDNA gene. In its systematic classification, it has a special position. Because it is transcribed, and thus is part of the mRNA and a biologically inactive precursor molecule, preRNA, it is not part of the intergene region. The precursor molecule is converted into a biologically active molecule in the ribosomal context by excising the transcribed spacer. On the other hand, it cannot be assigned functionally or phylogenetically to the 23 S gene or the 5 S gene. As the gene concept apparently cannot be utilized for classification in this case, let the "transcribed spacer" of the ribosomal operon be considered an independent functional DNA (RNA) class equivalent to the "gene" and the "intergenic region".

Homologous DNA Sequences

DNA or RNA sequences are homologous if they have the same phylogenetic origin. That may be recognizable by the fact that at least 40% of the nucleotides in a DNA segment are identical. There may be variable pieces in a large DNA segment. In that case it is sufficient for the phylogenetic relation to be shown by presence of a sequence 25 nucleotides long, which is at least 60% identical with another sequence, 25 nucleotides long, of the DNA being compared. Also, homologous sequences can frequently best be recognized by comparison with closely related organisms. To recognize homology of sequences of more distantly related organisms, it is then necessary to do a step-by-step comparison with sequences of species which bridge the separation to the distantly related phylogenetic species.

Identical DNA Sequences/Percent Identity

Subsequences of a larger polynucleotide are considered to determine the identity (in the sense of complete agreement, equivalent to 100% identity) of DNA or RNA sequences. These subsequences comprise 10 nucleotides, and are identical if all 10 components are identical in two comparison sequences. The nucleotides thymidine and uridine are considered identical. All the possible fragments of a larger polynucleotide can be considered as subsequences.

The identity is 90% if 9 of 10 nucleotides, or 18 or 20 nucleotides, are the same in a section on the two sequences being compared.

As an example, consider two polynucleotides made up of 20 nucleotides, which differ at the $5^{th}$ component. In a sequence comparison, then one would find six 10-element nucleotides which are identical and 5 which are not identical because they differ in one component.

The identity can also be determined by degrees, with the unit reported being a percentage. To determine the degree of identity such subsequences are considered that comprise at least the length of the sequence actually used, e.g. as a primer, or 20 nucleotides.

As an example, we compare polynucleotide A with a length of 100 nucleotides and polynucleotide B with a length of 200 nucleotides. A primer is derived from polynucleotide B with a length of 14 nucleotides. To determine the degree of identity, polynucleotide A is compared with the primer over its entire length. If the sequence of the primer occurs in polynucleotide A, but with a difference in one component, then we have a fragment with a degree of identity of 13/14, or 92.3%.

As a second example, the two polynucleotides above, A and B, are compared in their entirety. In this case, all the possible comparison windows with lengths of 20 nucleotides are applied and their degrees of identity are determined. Then if nucleotides numbered 50–69 of polynucleotides A and B are identical except for nucleotide number 55, then these fragments have a degree of identity of 19/20 or 95%.

Conserved and Variable Primers

Conserved primers are nucleotides which hybridize with conserved DNA or RNA regions. The concept 'conserved' characterizes the evolutionary variability of a nucleotide sequence for species of various taxonomic units. Therefore it is a measure of comparison. Depending on which sequence is used for comparison, a region or primer can be conserved or variable. Characterization of a primer as "conserved" or "variable" is accomplished by means of directly adjacent or overlapping regions with respect to the of hybridization target, which have the same length as the primer. Therefore one can select comparison sequences from the same organism, or homologous or similar segments from different organisms. When two sequences are compared, one is conserved if it is at least 95% identical with the comparison sequence, or variable if it is less than 95% identical.

Nested Primers

Nested primers are used particularly in consensus PCR. These are primers which amplify a fragment of an already amplified polynucleotide. Therefore nested primers hybridize with a region within an already multiplied DNA or RNA target molecule. Amplification with nested primers can be done as frequently as desired, giving successively smaller amplification products.

Hybridization of DNA or RNA

Two identical or similar nucleotide fragments can hybridize with each other to form a double strand. Such hybridization does not occur only between DNA, RNA, or PNA single strands. It is also possible for hybrid molecules to form between DNA and RNA, DNA and PNA, RNA and PNA, etc. There are numerous factors which determine whether two polynucleotides hybridize. Hybridization can take place in a temperature range of, preferably, 37–60° C. Hybridization can also occur in discrete hybridization and washing steps. Example 4) presents experimental parameters to make hybridization conditions more specific. Specific hybridization takes place if only a single hybridization with the desired target sequence occurs with the probe used and not with any other DNA which is also in the sample.

Combinations in Use of Nucleotides

Primers, probes, DNA fragments, subregions of polynucleotides or oligonucleotides can be used in many combinations. Possibilities include, for instance, arbitrary combination of two primers from a group of primers; arbitrary selection of one probe from a group of sequences; and selection of primers from the same group of sequences. In the latter cases the primer and probe(s) may be identical or different. Primers or probes can also be made up of two or more DNA fragments, with all possible variations in the composition being eligible. Combinations are also possible in the sequence of distinct PCR steps with different primers and the use of probes.

Consensus PCR

A consensus PCR is carried out with consensus primers. These are able to amplify the DNA of at least 2 taxonomic units (of all taxonomic units in the ideal case). In subsequent analysis steps, the identity of the amplified DNA is determined. For this purpose, either other PCR steps are done, which discriminate between smaller taxonomic units with variable nested primers if necessary, or the final determination of a laxonomic unit can be done with specific probes rather than with variable primers.

Nucleotides

Nucleotides are the building blocks of DNA or RNA. The abbreviations mean: G=guanosine, A=adenosine, T=thymidine, C=cytidine, R=G or A; Y=C or T; K=G or T; W=A or T; S=C or G; M=A or C; B=C, G or T; D=A, G or T; H=A, C or T; V=A, C, or G; N=A, C, G. or T; I=inosine.

Taxonomic Units

Taxonomic units of bacteria are all the known taxonomic subdivisions, such as kingdoms, classes, phyla, orders, families, genera, species, strains, intermediates of those taxonomic units such as subclasses, suborders, subfamilies, etc.; or groups of these taxonomic units.

DETAILED DESCRIPTION OF THE INVENTION

This invention comprises essentially 5 partial aspects which reflect the invention in its general form and in its special aspects:
   strategic selection of DNA target regions using adjacent genes
   description of use of a ribosomal DNA region from the end of the 23 S rDNA, the transcribed spacer, and parts of the 5 S rDNA to detect all bacteria
   provision of primers and probes for many bacteria
   detection of the families of the enterobacteria and their members
   use of a consensus PCR to detect all bacteria Strategic Selection of DNA Target Regions Using Adjacent Genes The invention consists in the use of portions of adjacent genes to detect taxonomic units, i.e., kingdoms, classes, phyla, families, genera and strains, as well as intermediate forms of these units. The advantage of the invention is that DNA regions which span two genes are very heterogeneous with respect to variability. That has been found, for instance, with the ribosomal operons, especially the 23 S/5 S rDNA segment. Because of the presence of very strongly conserved regions and very poorly conserved regions, one skilled in the art is enabled to detect all possible closely and even distantly related organisms.

Description of Use of a Ribosomal DNA Region from the End of the 23 S rDNA, From the Transcribed Spacer, and From Parts of the 5 S rDNA to Detect all Bacteria In particular, a 23 S–5 S rDNA region comprising about 400–750 nucleotides can be used to detect bacteria. The latter region consists of about 330–430 nucleotides of the terminal region of the 23 S rDNA, the adjoining transcribed spacer, and the 5 S rDNA gene. In individual cases, a t-RNA gene can also be inserted into the spacer and used for the detection. The region described corresponds to the nucleotides 2571–3112 of the SEQ ID 1, which represents the 23 S and 5 S rDNA genes of *Escherichia coli*. The homologous regions, and those corresponding to the above region, from other bacteria can be determined by a sequence comparison known to those skilled in the art. The beginning of the above-described region at the terminus of the 23 S rDNA gene and the end of the 5 S rDNA genes can be determined easily by comparing the ribosomal DNA sequences of two species A and B, especially for members of the same families, or even orders or phyla. Should this not be as easy for a comparison of species A and a more distantly related species C, one arrives at the desired result by making a comparison between the sequences of species B and C, in which B and C should be closely related to each other. In this way, by a series of separate sequence comparisons, it is possible to determine the homogeneous ribosomal regions of the 23 S rDNA, the transcribed spacer, and the 5 S rDNA of all Eubacteria. Because of the variability of individual subregions, length differences of several hundred nucleotides can occur. In addition, this invention allows use of subregions of the region described above. Table 6 describes a large portion of these regions.

Provision of/Providing Primers and Probes for Many Bacteria

Along with the general description of the useful rDNA region, sequences (SEQ ID 1–530) are also provided, which can be used to detect bacteria. Depending on the particular objective, the polynucleotides occurring in SEQ ID 1–530 can be used completely, or fragments of the sequence can be used. The sequences specified in SEQ ID 1–530 are derived from the previously described region of the 23 S rDNA gene, transcribed spacer, and 5 S rDNA gene.

In the technical execution, organisms can be detected by means of the DNA regions and sequences specified for that purpose, using probes and/or primers. Primers are nucleotides which act as starter molecules for the amplification. They deposit on the target sequence, so that the region is synthesized anew using a polymerase. Their specificity can be adjusted by the degree of identity of the primer with the target sequence. The taxonomic specificity is also determined by the selection of the target sequence within the ribosomal region described here (see also Table 6). Primers can thus be used in different ways: For instance, it is possible to amplify the entire region corresponding to FIG. 2, or homologous to the nucleotides number 2571–3112 of the SEQ ID 1 (*E. coli*) with primers SEQ ID 211 and 212. A mixture of more than two primers can also be used to optimize the amplification. Moreover it is possible to select the primer so that only the DNA of certain bacteria is amplified. In this case, then, there are two kinds of information in the case of positive amplification: First, they show the presence of the bacteria sought; and second, they show the identity of the bacteria. By means of sequential amplification steps with nested primers, the information obtained at the end of the DNA synthesis can be adjusted according to the requirements.

In a distinct step, the DNA, which ideally has previously been amplified, is bound to probes, concentrated, and detected. Probes are oligonucleotides or polynucleotides which can bind to single-stranded DNA segments. The affinity of the probes to the target sequence is determined by their degree of identity with it. The hybridization conditions also have a significant effect. That is, the buffer salt concentration, the incubation time, and the incubation temperature must be optimized. One skilled in the art can rapidly optimize those parameters using current methods. Exemplary hybridization conditions are given in the examples. Probes, just like primers, can work in two ways. First, they can show the presence of bacterial DNA or amplification products. Second, they can contribute to the detection of the DNA of specific bacteria. In this duality of their function they resemble the primers. Accordingly, the task of identification of organisms can be divided between primers and probes. Also, the probes, like the primers, derive from freely selectable regions of the terminal region of the 23 S rDNA, of the transcribed spacer, of the 5 S rDNA, or from the entire region.

One special advantage of this invention is that the ribosomal region selected according to FIG. 2 is be composed heterogeneously of very variable and very conserved regions, over an extremely broad range. As there are very many combinations in utilization of subregions, e.g., as shown in Table 6, this invention offers the potential of detecting all bacterial species and taxonomic units.

Detection of the Family of the Enterobacteria and their Members

Bacterial families such as the Enterobacteriaceae can be detected by using the DNA target regions characterized in this document (Example 1). The enterobacteria are a homogeneous taxonomic unit of the γ branch of the proteobacteria or purple bacteria. They are of particular interest because they include many pathogenic bacteria, such as *Escherichia coli* (EHEC, etc.), *Shigella, Salmonella*, and *Yersinia*. Thus they are suitable marker organisms for examining the hygienic status of foods. In clinical microbiology, detection of enterobacteria can be an initial step in narrowing down or identifying pathogenic microorganisms. From the list contained in this work, for instance, the primer SEQ ID 2–25, in various combinations, is usable for identifying the enterobacteria as the family. Many of the sequences listed are also suitable for identifying individual members of the enterobacteria, i.e., genera, species and strains. Other sequences are also produced for the other taxonomic units of the proteobacteria, especially the entire γ branch, as well as for the Firmicutes. Description of the ribosomal region as shown in FIG. 2 shows another way in which one skilled in the art can easily obtain more sequences so as to detect all the Eubacteria.

Use of a Consensus PCR to Detect all Bacteria

One special advantage of our invention is that the DNA target region, as described in FIG. 2, can be detected in an ideal manner in a consensus PCR. One significant prerequisite for the experimental applicability of this method is that the sequences become increasingly variable within a target region to be amplified. The region of the ribosomal operon which we have characterized has such a configuration for all the species investigated.

The plan for the consensus PCR is outlined in FIG. 8. As a general rule, a "master fragment" is amplified first. That can be the same as the complete fragment as shown in FIG. 2, or a part of it. Now if there are various microorganisms to be identified in a sample, this fragment is amplified for all of them. Finally, the individual organisms are identified with specific probes and/or in combination with more PCR steps. The detection with probes can even be miniaturized and accomplished on chips. Alternatively, detection can be done in the classical ELISA procedure. The components for bacterial detection can be prepared in the form of a kit.

Fluorescent dyes are particularly advantageous for detection. They can be coupled to the primers or to the probes. However, non-fluorescent dyes are also used often, particularly in the ELISA or the Southern Blot procedures. Genetrack and Light Cycler technology provides another possibility for detection. In principle, all these methods offer the option of quantitative determination. Thus by evaluating the detection signal it is also possible to ultimately draw conclusions about the number of bacteria in a sample.

Detection of bacteria with this invention can be done in an experimental context that is well known to one skilled in the art. For instance, bacteria can first be enriched in a suitable medium before detection. In working with foods, physical separation steps such as centrifugation or sedimentation are advantageous. It is also possible to enrich the bacteria in such a way that it is later possible to draw conclusions about their initial number. Furthermore, one can do threshold value tests with respect to the bacterial count. All in all, then, quantitative or semiquantitative determination of microorganisms is possible.

The (enriched) bacteria are broken up to isolate the genomic DNA. The procedures for cell disintegration that are well known to one skilled in the art are often based on physical (glass beads, heat) and chemical (NaOH) influences. It is also possible, though, to use cells directly in a PCR to detect DNA. Moreover it can also be advantageous to purify the genomic DNA, especially if it is distributed through a food matrix. These procedures are also known to those skilled in the art. DNA purification kits are also commercially available.

TABLE 1

Detection of *enterobacteria* excluding other bacteria (Example 1)

| No. | Species | Strain | Detection |
|---|---|---|---|
| 1 | Budvicia aquatilis | DSM 5025 | + |
| 2 | Buttiauxella agrestis | DSM 4586 | + |
| 3 | Cedecea davisae | DSM 4568 | + |
| 4 | Citrobacter koser | DSM 4595 | + |
| 5 | Erwinia carotovora | DSM 30168 | + |
| 6 | Erwinia chrysanthemi | DSM 4610 | + |
| 7 | Ewingella americana | DSM 4580 | + |
| 8 | Enterobacter agglomerans | B-5081-i | + |
| 9 | Enterobacter aerogenes | DSM 30053 | + |
| 10 | Enterobacter sakazakii | DSM 4485 | + |
| 11 | Enterobacter intermedius | DSM 4581 | + |
| 12 | Enterobacter cloacae | DSM 30054 | + |
| 13 | E. coli | BC 7883 | + |
| 14 | E. coli | H123 | + |
| 15 | E. coli | BC 7884 | + |
| 16 | E. coli | BC 7885 | + |
| 17 | E. hermanii | B-4943a | + |
| 18 | E. coli | ATCC 8739 | + |
| 19 | Hafnia alvei | DSM 30163 | + |
| 20 | Klebsiella pneumoniae | ATCC 13883 | + |
| 21 | Klebsiella pneumoniae | DSM 2026 | + |
| 22 | Klebsiella planticola | DSM 4617 | + |
| 23 | Klebsiella oxytoca | DSM 5175 | + |
| 24 | Kluyvera cryocrescens | DSM 4583 | + |
| 25 | Morganella morganii | DSM 30164 | + |
| 26 | Plesiomonas shigelloides | DSM 8224 | + |
| 27 | Pantoea ssp. | B-5200 | + |
| 28 | Pantoea dispersa | DSM 30073 | + |
| 29 | Proteus rettgeri | DSM 1131 | + |
| 30 | Proteus rettgeri | ATCC 14505 | + |
| 31 | Providencia stuartii | DSM 4539 | + |
| 32 | Rahnella aquatilis | DSM 4594 | + |
| 33 | Rahnella aquatilis | DSM 4594 | + |
| 34 | Serratia proteamaculans | DSM 4487 | + |
| 35 | Serratia ficaria | DSM 4509 | + |
| 36 | Serratia plymutica | DSM 49 | + |
| 37 | Serratia rubidea | DSM 4480 | + |
| 38 | Serratia marcescens | DSM 1636 | + |
| 39 | Salmonella bongori | DSM 7952 | + |
| 40 | Yersinia pseudotuberculosis | DSM 8992 | + |
| 41 | Yersinia pseudotuberculosis | DSM 8992 | + |
| 42 | Yersinia enterolytica | DSM 4790 | + |
| 43 | Acinetobacter calcoaceticus | DSM 590 | − |
| 44 | Aeromonas hydrophila | DSM 6173 | − |
| 45 | Aeromonas enteropelogenes | DSM 6394 | − |
| 46 | Fransilla tularensis Isolat | F16 | − |
| 47 | Franzisella philomiragia | DSM 7535 | − |
| 48 | Moraxella catarrhalis | DSM 9143 | − |
| 49 | Pasteurella pneumotropica | B-2397 A 13 | − |
| 50 | Pseudomonas beyjerinkii | DSM 7218 | − |
| 51 | Vibrio fischeri | DSM 507 | − |
| 52 | Vibrio alginolyticus | DSM 2171 | − |
| 53 | Vibrio proteolyticus | DSM 30189 | − |
| 54 | Vibrio paramaemolytiucs | DSM 10027 | − |
| 55 | Vibrio harveyi | DSM 6104 | − |
| 56 | Xanthomonas maltophila | BC 4273 | − |
| 57 | Achromobacter xylosa | DSM 2402 | − |
| 58 | Alcaligenes spp | DSM 2625 | − |
| 59 | Alcaligenes latus | DSM 1122 | − |
| 60 | Brucella neotomae | ATCC 25840 | − |
| 61 | Brucella ovis | ATCC 23459 | − |
| 62 | Enterococcus casseliflavus | DSM 20680 | − |
| 63 | Flavobacterium sp | ATCC 27551 | − |
| 64 | Flavobacterium resinovorum | DSM 7438 | − |
| 65 | Flavobacterium johnsonii | DSM 2064 | − |
| 66 | Flavobacterium flavense | DSM 1076 | − |
| 67 | Lactobacillus bifermentans | BC 8463 | − |
| 68 | Pseudomonas paucimobilis | DSM 1098 | − |
| 69 | Pseudomonas cepacia | DSM 3134 | − |
| 70 | Sphingobacterium multivorans | DSM 6175 | − |

TABLE 2

Detection of *Pantoea dispersa* excluding other bacteria (Example 2)

| No. | Species | Detection |
|---|---|---|
| 1 | Pantoea dispersa | + |
| 2 | Budvicia aquatica | − |
| 3 | Buttiauxella agrestis | − |
| 4 | Enterobacter agglomerans | − |
| 5 | Erwinia carotovora | − |
| 6 | Erwinia crysanthemi | − |
| 7 | Escherichia coli | − |
| 8 | Escherichia vulneris | − |
| 9 | Escherichia hermannii | − |
| 10 | Hafnia alvei | − |
| 11 | Klebsiella oxytoca | − |
| 12 | Kluyvera cryoescens | − |
| 13 | Morganella morganii | − |
| 14 | Proteus mirabilis | − |
| 15 | Proteus rettgeri | − |
| 16 | Proteus stuartii | − |
| 17 | Providencia stuartii | − |
| 18 | Rahnella aquatilis | − |
| 19 | Serratia ficaria | − |
| 20 | Serratia fonticola | − |
| 21 | Serratia marcescens | − |
| 22 | Serratia plymuthica | − |
| 23 | Serratia proteamaculans | − |
| 24 | Serratia rubidea | − |
| 25 | Yersinia enterolytica | − |
| 26 | Yersinia peudotuberculosis | − |
| 27 | Acinetobacter calcoaceticus | − |
| 28 | Aeromonas enteropelogenes | − |
| 29 | Aeromonas hydrophila | − |
| 30 | Cedecea davisae | − |
| 31 | Haemophilus influenzae | − |
| 32 | Moraxella catarrhalis | − |
| 33 | Pasteurella pneumotropica | − |
| 34 | Stenotrophomonas multophila | − |
| 35 | Vibrio alginolyticus | − |
| 36 | Vibrio fisheri | − |
| 37 | Vibrio harveyi | − |
| 38 | Vibrio parahaemolyticus | − |
| 39 | Alcaligenes sp. | − |
| 40 | Bacillus subtilis | − |
| 41 | Brucella abortus | − |
| 42 | Brucella ovis | − |
| 43 | Flavobacterium resinovorum | − |
| 44 | Pseudomonas paucimobilis | − |
| 45 | Pseudomonas cepacia | − |
| 46 | Ralstonia pickettii | − |
| 47 | Sphingobacterium multivorum | − |
| 48 | Sphingomonas paucimobilis | − |
| 49 | Streptococcus faecalis | − |

TABLE 3

Detection of a group of genera with the probe GTTCCGAGATTGGTT

| No. | Species | Detection |
|---|---|---|
| 1 | Rahnella aquatilis | + |
| 2 | Serratia ficaria | + |
| 3 | Serratia fonticola | + |
| 4 | Serratia marcescens | + |
| 5 | Serratia plymuthica | + |
| 6 | Serratia proteamaculans | + |
| 7 | Serratia rubidea | + |
| 8 | Yersinia enterolytica | + |
| 9 | Yersinia peudotuberculosis | + |
| 10 | Budvicia aquatica | − |
| 11 | Buttiauxella agrestis | − |
| 12 | Enterobacter agglomerans | − |
| 13 | Erwinia carotovora | − |
| 14 | Erwinia crysanthemi | − |
| 15 | Escherichia coli | − |

TABLE 3-continued

Detection of a group of genera with the probe GTTCCGAGATTGGTT

| No. | Species | Detection |
|---|---|---|
| 16 | Escherichia vulneris | – |
| 17 | Escherichia hermannii | – |
| 18 | Hafnia alvei | – |
| 19 | Klebsiella oxytoca | – |
| 20 | Kluyvera cryoescens | – |
| 21 | Morganella morganii | – |
| 22 | Pantoea dispersa | – |
| 23 | Proteus mirabilis | – |
| 24 | Proteus rettgeri | – |
| 25 | Proteus stuartii | – |
| 26 | Providencia stuartii | – |
| 27 | Acinetobacter calcoaceticus | – |
| 28 | Aeromonas enteropelogenes | – |
| 29 | Aeromonas hydrophila | – |
| 30 | Cedecea davisae | – |
| 31 | Haemophilus influenzae | – |
| 32 | Moraxella catarrhalis | – |
| 33 | Pasteurella pneumotropica | – |
| 34 | Stenotrophomonas multophila | – |
| 35 | Vibrio alginolyticus | – |
| 36 | Vibrio fisheri | – |
| 37 | Vibrio harveyi | – |
| 38 | Vibrio parahaemolyticus | – |
| 39 | Alcaligenes sp. | – |
| 40 | Bacillus subtilis | – |
| 41 | Brucella abortus | – |
| 42 | Brucella ovis | – |
| 43 | Flavobacterium resinovorum | – |
| 44 | Pseudomonas paucimobilis | – |
| 45 | Pseudomonas cepacia | – |
| 46 | Ralstonia pickettii | – |
| 47 | Sphingobacterium multivorum | – |
| 48 | Sphingomonas paucimobilis | – |
| 49 | Streptococcus faecalis | – |

TABLE 4

Specific probes for the detection of bacterial genera and species

| No. | Probe SEQ ID | Detection of Genus/Species |
|---|---|---|
| 1 | 96 | Budvicia aquatica |
| 2 | 97 | Buttiauxella agrestis |
| 3 | 98 | Enterobacter agglomerans |
| 4 | 99 | Erwinia carotovora |
| 5 | 100 | Erwinia chrysanthemi |
| 6 | 101 | Escherichia coli |
| 7 | 102 | Escherichia hermannii |
| 8 | 103 | Escherichia vulneris |
| 9 | 104 | Hafnia alvei |
| 10 | 105 | Klebsiella oxytoca |
| 11 | 106 | Kluyvera cryoescens |
| 12 | 107 | Morganella morganii |
| 13 | 108, 109 | Pantoea |
| 14 | 110 | Proteus mirabilis |
| 15 | 111 | Proteus rettgeri |
| 16 | 112 | Providencia stuartii |
| 17 | 113 | Rahnella aquatilis |
| 18 | 114 | Serratia ficaria |
| 19 | 115 | Serratia fonticola |
| 20 | 116 | Serratia marcescens |
| 21 | 117 | Serratia plymuthica |
| 22 | 118 | Serratia proteamaculans |
| 23 | 119 | Serratia rubidea |
| 24 | 120 | Yersinia enterolytica |
| 25 | 121 | Yersinia pseudotuberculosis |
| 26 | 122 | Acinetobacter calcoaceticus |
| 27 | 123 | Aeromonas enteropelogenes |
| 28 | 124 | Aeromonas hydrophila |
| 29 | 125 | Cedecea davisae |
| 30 | 126 | Haemophilus influenzae |
| 31 | 127 | Moraxella catharralis |
| 32 | 128 | Pasteurella pneumotropica |
| 33 | 129 | Stenotrophomonas multophila |
| 34 | 130 | Vibrio alginolyticus |
| 35 | 131 | Vibrio fisheri |
| 36 | 132 | Vibrio harveyi |
| 37 | 133 | Vibrio parahaemolyticus |
| 38 | 134 | Vibrio proteolyticus |
| 39 | 432 | Salmonella typhi |
| 40 | 433 | Buchnera aphidocola |
| 41 | 434 | Pseudomonas stutzeri |
| 42 | 435 | Thiobacillus ferrooxidans |
| 43 | 436 | Agrobacterium vitis |
| 44 | 437 | Adalia bipunctata |
| 45 | 438 | Amycocalatopsis orientalis |
| 46 | 439 | Brucella |
| 47 | 440 | Bradyrhyzobium japonicum |
| 48 | 441 | Pseudomonas paucimobilis |
| 49 | 442 | Rhodobacter sphaeroides |
| 50 | 443 | Rickettsia prowazekii |
| 51 | 444 | Pseudomonas cepacia |
| 52 | 445 | Ralstonia pickettii |
| 53 | 446 | Campylobacter jejuni |
| 54 | 447 | Helicobacter pylori |
| 55 | 448 | Actinoplanes utahensis |
| 56 | 449 | Bacillus halodurans |
| 57 | 450 | Bacillus subtilis |
| 58 | 451 | Clostridium tyrobutyricum |
| 59 | 452 | Frankia |
| 60 | 453 | Microbispora bispora |
| 61 | 454 | Mycobacterium leprae |
| 62 | 455 | Mycobacterium smegmatis |
| 63 | 456 | Mycobacterium tuberculosis |
| 64 | 457 | Mycoplasma gallisepticum |
| 65 | 458 | Propionibacterium freudenreichii |
| 66 | 459 | Rhodococcus erythropolis |
| 67 | 460 | Rhodococcus fascians |
| 68 | 461 | Staphylococcus aureus |
| 69 | 462 | Streptococcus faecalis |
| 70 | 463 | Streptomyces ambifaciens |
| 71 | 464 | Streptomyces galbus |
| 72 | 465 | Streptomyces griseus |
| 73 | 466 | Streptomyces lividans |
| 74 | 467 | Streptomyces mashuensis |
| 75 | 468 | Flavobacterium resinovorum |
| 76 | 469 | Sphingobacterium multivorans |
| 77 | 470 | Synechococcus |
| 78 | 471 | Synechocystis |
| 79 | 472 | Borrelia burgdorferi |
| 80 | 473 | Chlamydia trachomatis |
| 81 | 474 | Azotobacter vinelandii |
| 82 | 475 | Cowdria ruminantium |
| 83 | 476 | Mycobacterium intracellulare |
| 84 | 477 | Mycobacterium lufu |
| 85 | 478 | Mycobacterium simiae |
| 86 | 479 | Mycobacterium smegmatis |
| 87 | 480 | Saccharomonospora azurea |
| 88 | 481 | Saccharomonospora caesia |
| 89 | 482 | Saccharomonospora cyanea |
| 90 | 483 | Saccharomonospora glauca |
| 91 | 484 | Saccharomonospora viridis |
| 92 | 485 | Wolbachia pipientis |
| 93 | 525 | Sphingomonas paucimobilis |
| 94 | 526 | Zymomonas mobilis |
| 95 | 527 | Alcaligenes |
| 96 | 528 | Borrelia burgdorferi |
| 97 | 529 | Xanthomonas campestris |
| 98 | 530 | Cowduria ruminantium |

TABLE 5

Primers for detection of bacterial species or genera

| No. | Species used | SEQ ID | Forward primer | Reverse primer (reverse primer* = complementary) |
|---|---|---|---|---|
| 1 | Budvicia aquatica | 96 | CGAGGTGTTTTAAGGAAAGTT | CGGTCAATAGACAGAAATAT |
| 2 | Buttiauxellis agrestis | 97 | CGAAGGTGTTTTGGTTGAGAG | GGTTGATGAAACAGAATAT |
| 4 | Enterobacter agglomerans | 98 | CGAAGATGTTTTGGCGGATTG | GTTTCTGGCAACAGAATTT |
| 5 | Erwinia carotovora | 99 | CGAAGGTGTTTTGAGAGTGAC | TTGGGATGAAACAGAATTT |
| 6 | Erwinia chrysanthemi | 100 | CGAAGGTGTTTTAGAGAGATT | TCGGGATGAAACAAAATTT |
| 7 | Escherichia coli | 101 | CGAAGCTGTTTTGGCGGATGA | GTCTGATAAAACAGAATTT |
| 8 | Escherichia hermannii | 102 | CAGAGTGGTTTTGGTGTTGCG | CAGCAGGTGAACAGAATTT |
| 9 | Escherichia vulneris | 103 | CGAAGATGTTTTGGCGGATTT | CGTCAGACAGACAGAATTT |
| 10 | Hafnia alvei | 104 | CGAAGGTGTTTTAAGACGCAG | GGTACAAATAACAGAATAT |
| 11 | Klebsiella oxytoca | 105 | CGAAGATGTTTTGGCGATTTG | GTTTCTGACAACAGAATTT |
| 12 | Kluyvera cryoescens | 106 | CAAAGATGTTTTGGTGAAAAG | CGGGTTAATAACAGAATTT |
| 13 | Morganella morganii | 107 | CGAAGGTGTTTTGAGTTGAGA | TTTGGATTGAAATGAATTT |
| 14 | Pantoea dispersa | 108 | CAGAGGCGTTTTGGCGGATGA | GCGGTNTAAAACAAAATTT |
| 15 | Pantoea ssp. | 109 | CGAAGATGTTTTGGCGGAATG | GTTTCTGGCAACAGAATTT |
| 16 | Proteus mirabilis | 110 | CGAAAGTGTTTTGTCAGAGAG | AGTGATTAAAACCGAATTT |
| 17 | Proteus rettgeri | 111 | CGAAGGTGTTTTAGAGAGATA | CGGGAACAAAACAGAATTT |
| 18 | Providencia stuartii | 112 | CGAAGGTGTTTTAGAGAGACA | ACGGGAACGAACCGAATTT |
| 19 | Rahnella aquatilis | 113 | CGAAGGTGTTTTTGATTTGAG | TATGAATGAAACAGAATTT |
| 20 | Salmonella typhi | 432 | CGAAGGTGTTTTGGAGGATAA | GATAAAAGAAACAGAATTT |
| 21 | Serratia ficaria | 114 | CGAAGGTGTTTTAGAGAGACG | CAAGAATGAAACAGAATTT |
| 22 | Serratia fonticola | 115 | CCAAGGTGTTTTGAAGAGATT | TTGAAATGAAACAGAATTT |
| 23 | Serratia marcescens | 116 | CGAAGGTGTTTTTAGAGAGAT | TTGGAATGAAACAGAATTT |
| 24 | Serratia plymuthica | 117 | CGAAGGTGTTTTAGAGAGATT | TTGGAATGAAACAGAATTT |
| 25 | Serratia proteamaculans | 118 | CAAAGGTGTTTTAGAGAGATT | TTGGAATGAAACANAATTT |
| 26 | Serratia rubidea | 119 | CGAAGGTGTTTTAGAGAGATT | TCGGGATGAAACAGAATTT |
| 27 | Yersinia enterolytica | 120 | CAAAGGTGTTTTGTATTTGAG | GTTAGTTTAGACAGAATTT |
| 28 | Acinetobacter calcoaceticus | 122 | CCAAGCAGTTGTATATAAAGC | GCAACCAATAAGACCAATG |
| 29 | Aeromonas enteropelogenes | 123 | CCAAGAAGTGTTTNTGGTGCT | TTCCAAGATTGAAGATTTT |
| 30 | Aeromonas hydrophila | 124 | CCAAGAAGTGTTCTAAGGCTT | TTCTCAGATTGAAGAATTT |
| 31 | Buchnera aphidocola | 433 | CCAGAGGTGTTTTTTATAAAA | ATCTTGTTTTACTGAATTT |
| 32 | Haemophilus influenzae | 126 | GCTCAAGTGTTTTTGGGAGCT | CGGTCAGTAAACAGAATTT |
| 33 | Moraxella catarrhalis | 127 | ACCCAAGTGGTTTACCACTGA | GTAATAAACAGACTCATAC |
| 34 | Pasteurella pneumotropica | 128 | ACCAAATTTGTTTATCGTAAC | AGTTGTTATAATAAAACAT |
| 35 | Vibrio alginolyticus | 130 | CCAAGGGGTTTTGATGGACTC | TTTCCAGATAAACAGAATTT |
| 36 | Vibrio fisheri | 131 | CCAAGTGGTTTGTATCAAGCA | TTAAGTAAAACAAACACAG |
| 37 | Vibrio harveyi | 132 | CCAAGGGGTTTTGATGGACTC | TTTCCAAATTAAAGAATTT |
| 38 | Vibrio parahaemolyticus | 133 | CCAAGGGGTTTTGATGGACTC | TTTCCGAATTAAAGAATTT |
| 39 | Vibrio proteolyticus | 134 | CCAAGGGGTTTTGATGGACTC | TTGTTCCAGACAAAATTTT |

TABLE 6

Detection potential and specification of the location of DNA fragments from the rDNA operon

| No. in FIG. 2 | DNA region | Position in SEQ ID 1 | Detection potential |
|---|---|---|---|
| 1. | Terminal region of the 23 S rDNA gene | 2667–2720 | Phyla, classes, orders, families |
| 2. | Terminal region of the 23 S rDNA gene | 2727–2776 | Phyla, classes, orders, families |
| 3. | Terminal region of the 23 S rDNA gene | 2777–2800 | Phylas, classes, orders, families |
| 4. | Terminal region of the 23 S rDNA gene | 2801–2838 | Classes, orders, families |
| 5. | End of the 23 S rDNA gene | 2857–2896 | Phyla, classes, orders, families |
| 6. | Beginning of the 23 S–5 S transcribed spacer | 2897–2938 | Orders, families, genera, species, strains |
| 7. | 23 S–5 S transcribed spacer | 2939–2983 | Genera, species, strains |
| 8. | End of the 23 S–5 S transcribed spacer | 2984–2999 | Families, genera, species, strains |
| 9. | Beginning of the 5 S rDNA gene | 3000–3032 | Phyla, classes, orders, families |

TABLE 7

Primers from Example 1

| Forward primer | Reverse primer | Annealing temperature (° C.) | FIG. |
|---|---|---|---|
| SEQ ID 2 | SEQ ID 7–22 | 62 | 3 |
| SEQ ID 2 | SEQ ID 23–24 | 62 | 4 |
| SEQ ID 2 | SEQ ID 25 | 67 | 5 |
| SEQ ID 3–6 | SEQ ID 23–24 | 62 | 6 |
| SEQ ID 3–6 | SEQ ID 25 | 67 | 7 |

TABLE 8

Consensus PCR for detection of bacteria

| No. | Taxonomic unit | Primer A1 SEQ ID | Primer B1 SEQ ID | Primer C1 SEQ ID | Primer D1 SEQ ID | Primer E1 SEQ ID | Primer F1 SEQ ID | Primer G1 SEQ ID | Primer H1 SEQ ID | Primer B2 SEQ ID | Primer A2 SEQ ID |
|---|---|---|---|---|---|---|---|---|---|---|---|
| 1 | *Enterobakterien* | 1 | 7–22 | | | | | | | 4 | 5 |
| 2 | *Enterobakterien* | 26 | 34 | 42 | 54 | 66 | 78 | 85 | | | 135 |
| 3 | *Acinetobacter* | 27 | 35 | 43 | 55 | 67 | 79 | | | | |
| 4 | *Aeromonas* | 28 | 36 | 44 | 56 | 68 | 80 | 87 | | | 155 |
| 5 | *Haemophilus* | 29 | 37 | 45 | 57 | 69 | 81 | | | | |
| 6 | *Moraxella* | 30 | 38 | 46 | 58 | 70 | 82 | | | | |
| 7 | *Pasteurella* | 31 | 39 | 47 | 59 | | | | | | |
| 8 | *Stenotrophomonas* | 32 | 40 | 48 | 60 | 72 | | 90 | | | |
| 9 | *Vibrio* | 33 | 41 | | | | | | | | |
| 10 | *Vibrio alginolyticus* | | | 49 | 61 | 73 | | 91 | 130 | | 160 |
| 11 | *Vibrio fisheri* | | | 50 | 62 | 74 | | 92 | 131 | | 161 |
| 12 | *Vibrio harveyi* | | | 51 | 63 | 75 | | 93 | 132 | | 162 |
| 13 | *Vibrio parahaemolyticus* | | | 52 | 64 | 76 | | 94 | 133 | | 163 |
| 14 | *Vibrio proteolyticus* | | | 53 | 65 | 77 | | 95 | 134 | | 163 |
| 15 | *Pasteurella pneumotropica* | | | | | 71 | 83 | | 128 | | 158 |
| 16 | *Acinetobacter calcoaceticus* | | | | | | | 86 | 122 | | 154 |
| 17 | *Haemophilus influenzae* | | | | | | | 88 | 126 | | 156 |
| 18 | *Moraxella catarrhalis* | | | | | | | 89 | 127 | | 157 |
| 19 | *Budvicia aquatica* | | | | 166 | | | | 96 | | 135 |
| 20 | *Buttiauxella agrestis* | | | 187 | 167 | | | | 97 | | 136 |
| 21 | *Enterobacter agglomerans* | | | 188 | 168 | | | | 98 | | |
| 22 | *Erwinia carotovora* | | | 189 | 169 | | | | 99 | | |
| 23 | *Erwinia chrysanthemi* | | | 190 | 170 | | | | 100 | | 138 |
| 24 | *Escherichia coli* | | | 187 | 171 | | | | 101 | | 139 |
| 25 | *Escherichia hermannii* | | | 191 | 172 | | | | 102 | | 140 |
| 26 | *Escherichia vulneris* | | | 192 | 173 | | | | 103, 165 | | 141 |
| 27 | *Hafnia alvei* | | | 193 | 174 | | | | 104 | | 142 |
| 28 | *Klebsiella oxytoca* | | | 187 | 175 | | | | 105, 165 | | 143 |
| 29 | *Kluyvera cryoescens* | | | 187 | 175 | | | | 106 | | 144 |
| 30 | *Morganella morganii* | | | 194 | 176 | | | | 107 | | 145 |
| 31 | *Pantoea dispersa* | | | 187 | 177 | | | | 108, 165 | | 146 |
| 32 | *Pantoea* | | | 188 | 178 | | | | 109, 165 | | 147 |
| 33 | *Proteus mirabilis* | | | 195 | 179 | | | | 110 | | |
| 34 | *Proteus rettgeri* | | | 196 | 180 | | | | 111 | | 148 |
| 35 | *Providencia stuartii* | | | 197 | 181 | | | | 112 | | 149 |
| 36 | *Rahnella aquatilis* | | | 198 | 182 | | | | 113, 164 | | 149 |
| 37 | *Serratia ficaria* | | | | | | | | 114, 164 | | 150 |
| 38 | *Serratia fonticola* | | | | | | | | 115, 164 | | |
| 39 | *Serratia marcescens* | | | | | | | | 116, 164 | | |
| 40 | *Serratia plymuthica* | | | | | | | | 117, 164 | | |
| 41 | *Serratia proteamaculans* | | | | | | | | 118, 164 | | |
| 42 | *Serratia rubidea* | | | | | | | | 119, 164 | | |
| 43 | *Yersinia enterolytica* | | | 199 | 184 | | | | 120, 164 | | 152 |
| 44 | *Yersinia pseudotuberculosis* | | | 200 | 185 | | | | 121, 164 | | 153 |
| 45 | *Aeromonas enteropelogenes* | | | | | | | | 123 | | |
| 46 | *Aeromonas hydrophila* | | | | | | | | 124 | | |
| 47 | *Cedecea davisae* | | | 201 | 186 | | | | 125 | | |
| 48 | *Stenotrophomonas multophila* | | | | | | | | 129 | | 159 |
| 49 | *Enterobacter agglomerans* | | | | | | | | 137, 165 | | |
| 50 | *Serratia* | | | | 183 | | | | | | 151 |
| 51 | *Citrobacter* | | | | | | | | 202, 203 | | |
| 52 | *Salmonella* | | | | | | | | 204–210 | | |
| 53 | *Pseudomonas stutzeri* | 213 | 252 | 289 | 326 | 361 | 403 | | 434 | | 488 |
| 54 | *Thiobacillus ferrooxidans* | 214 | 253 | 290 | 327 | 362 | 404 | | 435 | | 489 |
| 55 | *Agrobacterium vitis* | 215 | 254 | 291 | 328 | 363 | | | 436 | | 490 |
| 56 | *Adalia bipunctata* | 216 | 255 | 292 | 329 | 364 | | | 437 | | 491 |
| 57 | *Amycolatopsis orientalis* | 217 | 256 | 293 | 330 | | | | 438 | | |
| 58 | *Brucella ovis* | 218 | 257 | 294 | 331 | 365 | | | 439 | | 492 |
| 59 | *Bradyrizobium japonicum* | 219 | 258 | 295 | 331 | 366 | | | 440 | | 493 |
| 60 | *Pseudomonas paucimobilis* | 220 | 259 | 296 | 332 | 367 | | | 441 | | 494 |
| 61 | *Rhodobacter sphaeroides* | 221 | 260 | 297 | 333 | 368 | | | 442 | | 495 |
| 62 | *Rickettsia prowazekii* | 222 | 261 | 298 | 333 | 369 | | | 443 | | 496 |
| 63 | *Sphingomonas paucimobilis* | 223 | 262 | 299 | 334 | 370 | 405 | | 525 | | 499 |
| 64 | *Zymomonas mobilis* | 224 | 263 | 300 | 335 | 371 | | | 526 | | 500 |
| 65 | *Alcaligenes* | 225 | 264 | 301 | 336 | 372 | 406 | | 527 | | 501 |
| 66 | *Pseudomonas cepacia* | 226 | 265 | 302 | 337 | | 407 | | 444 | | 502 |
| 67 | *Ralstonia pickettii* | 227 | 266 | 303 | 338 | 373 | 408 | | 445 | | 503 |
| 68 | *Campylobacter jejuni* | 228 | 267 | 304 | 339 | 374 | 409 | | 446 | | |
| 69 | *Helicobacter pylori* | 229 | 268 | 305 | 340 | 375 | 410 | | 447 | | 504 |
| 70 | *Actinoplanes utahensis* | 230 | 269 | 306 | 341 | | 411 | | 448 | | |
| 71 | *Bacillus halodurans* | 231 | 270 | 307 | 342 | 376 | 412 | | 449 | | 505 |
| 72 | *Bacillus subtilis* | 232 | | | 343 | 377 | 413 | | 450 | | 506 |
| 73 | *Clostridium tyrobutyricum* | 233 | 271 | 308 | 344 | 378 | 414 | | 451 | | 507 |

TABLE 8-continued

Consensus PCR for detection of bacteria

| No. | Taxonomic unit | Primer A1 SEQ ID | Primer B1 SEQ ID | Primer C1 SEQ ID | Primer D1 SEQ ID | Primer E1 SEQ ID | Primer F1 SEQ ID | Primer G1 SEQ ID | Primer H1 SEQ ID | Primer B2 SEQ ID | Primer A2 SEQ ID |
|---|---|---|---|---|---|---|---|---|---|---|---|
| 74 | *Frankia* | 234 | 272 | 309 | 345 | 379 | 415 | | 452 | | 508 |
| 75 | *Microbispora bispora* | 235 | 273 | 310 | 346 | 380 | 416 | | 453 | | 509 |
| 76 | *Mycobacterium leprae* | 236 | 274 | 311 | 347 | 381 | 417 | | 454 | | 510 |
| 77 | *Mycobacterium smegmatis* | 237 | 275 | 312 | 348 | 382 | 418 | | 455 | | 511 |
| 78 | *Mycobacterium tuberculosis* | 238 | 276 | 313 | 349 | 383 | 419 | | 456 | | 512 |
| 79 | *Mycobacterium gallisepticum* | 239 | 277 | 314 | | 384 | 420 | | 457 | | |
| 80 | *Propionibacterium freudenreich* | 240 | 278 | 315 | 350 | 385 | 421 | | 458 | | |
| 81 | *Rhodococcus erythropolis* | 241 | 279 | 316 | 351 | 386 | 422 | | 459 | | 513 |
| 82 | *Rhodococcus fascians* | 242 | | | | 387 | 423 | | 460 | | 514 |
| 83 | *Staphylococcus aureus* | 243 | 280 | 317 | 352 | 388 | 424 | | 461 | | 515 |
| 84 | *Streptococcus faecalis* | 244 | 281 | 318 | 353 | 389 | 425 | | 462 | | 516 |
| 85 | *Streptomyces ambifaciens* | 245 | 282 | 319 | 354 | 390 | 426 | | 463 | | 517 |
| 86 | *Flavobacterium resinovorum* | 246 | 283 | 320 | 355 | 395 | 428 | | 468 | | 519 |
| 87 | *Sphingobacterium multivorans* | 247 | 284 | 321 | 356 | 396 | | | 469 | | 520 |
| 88 | *Synechococcus* | 248 | 285 | 322 | 357 | 397 | 429 | | 470 | | 521 |
| 89 | *Synechocystis* | 249 | 286 | 323 | 358 | 398 | 430 | | 471 | | 522 |
| 90 | *Borrelia burgdorferi* | 250 | 287 | 324 | 359 | 399 | | | 472, 428 | | 523 |
| 91 | *Chlamydia trachomatis* | 251 | 288 | 325 | 360 | 400 | 431 | | 473 | | 524 |
| 92 | *Streptomyces galbus* | | | | | 391 | 426 | | 464 | | |
| 93 | *Streptomyces griseus* | | | | | 392 | 426 | | 465 | | 518 |
| 94 | *Streptomyces lividans* | | | | | 393 | 426 | | 466 | | 518 |
| 95 | *Streptomyces mashuensis* | | | | | 394 | 427 | | 467 | | |
| 96 | *Salmonella typhi* | | | | | | 401 | | 432 | | 486 |
| 97 | *Buchnera aphidocola* | | | | | | | | 433 | | 487 |
| 98 | *Brucella orientalis* | | | | | | | | 439 | | 492 |
| 99 | *Brucella abortus* | | | | | | | | 439 | | 492 |
| 100 | *Azotobacter vinelandii* | | | | | | | | 474 | | |
| 101 | *Cowduria ruminantium* | | | | | | | | 475, 530 | | |
| 102 | *Mycobacterium intracellulare* | | | | | | | | 476 | | |
| 103 | *Mycobacterium lufu* | | | | | | | | 477 | | |
| 104 | *Mycobacterium simiae* | | | | | | | | 478 | | |
| 105 | *Mycobacterium smegmatis* | | | | | | | | 479 | | |
| 106 | *Saccharomonospora azurea* | | | | | | | | 480 | | |
| 107 | *Saccharomonospora caesia* | | | | | | | | 481 | | |
| 108 | *Saccharomonospora cyanea* | | | | | | | | 482 | | |
| 109 | *Saccharomonospora glauca* | | | | | | | | 483 | | |
| 110 | *Saccharomonospora viridis* | | | | | | | | 484 | | |
| 111 | *Wolbachia pipientis* | | | | | | | | 485 | | |
| 112 | *Rickettsia bellii* | | | | | | | | | | 497 |
| 113 | *Rickettsia rickettsii* | | | | | | | | | | 498 |
| 114 | *Xanthomonas campestris* | | | | | | | | 529 | | |

The invention claimed is:

1. A method for detecting any species of the taxonomic unit of Enterobacteriaceae, and no species of another taxonomic unit, in an analytical sample, comprising the step of bringing the analytical sample into contact with an added nucleic acid or a combination of added nucleic acids, and detecting suitable hybrid nucleic acids comprising at least one of the added nucleic acids and a bacterial nucleic acid, wherein the one or more added nucleic acids are selected from the group consisting of:
   a) nucleic acid molecules consisting of at least one sequence of SEQ ID NOs: 2 and 78;
   b) nucleic acid molecules which exhibit at least 90% identity with a nucleic acid according to a); and
   c) a nucleic acid molecule which is a full complement of a nucleic acid of a) or b),
   wherein any species of the taxonomic unit of Enterobacteriaceae, but no species of another taxonomic unit, is detected by formation of the hybrid nucleic acids.

2. The method of claim 1, wherein the method involves a PCR amplification of the bacterial nucleic acid.

3. The method of claim 1, wherein the method involves a Southern Blot hybridization.

4. A method for amplifying bacterial DNA of any species of the taxonomic unit of Enterobacteriaceae, comprising a first amplification step in which the DNA for any species of the taxonomic unit of Enterobacteriaceae, and no species of another taxonomic unit is amplified with conserved primers to obtain a first amplification fragment, and, optionally, at least one further amplification step (EN) in which parts of the first amplification fragment, which are specific for species of the taxonomic unit of Enterobacteriaceae, are multiplied with nested, increasingly variable primers, and, optionally, a further step in which the DNA fragments obtained by amplification, which are specific for species of the taxonomic unit of Enterobacteriaceae, are detected by means of probes, wherein a primers used in the first amplification step consists of a nucleic acid selected from the group consisting of:
   a) nucleic acid molecules consisting of at least one sequence of the SEQ ID NOs: 2 and 78;
   b) nucleic acid molecules which exhibit at least 90% identity with a nucleic acid according to a); and
   c) a nucleic acid molecule which is a full complement of a nucleic acid of a) or b).

5. The method of claim 4, wherein the method involves a PCR amplification of the bacterial DNA.

6. A method according to claim 4, wherein the method involves a Southern Blot hybridization.

7. The method of claim 1, wherein the one or more added nucleic acid molecules are modified or labeled so that they can generate a signal for analytical detection, with the modification or labeling selected from the group consisting of (i) radioactive groups, (ii) colored groups, (iii) fluorescent groups, (iv) groups for immobilization of a solid phase, and (v) groups which allow a direct or indirect reaction.

8. A method for detecting any species of the taxonomic unit of Enterobacteriaceae, and no species of another taxonomic unit, in an analytical sample, comprising the step of bringing the analytical sample into contact with a combination of nucleic acids, and detecting suitable hybrid nucleic acids comprising one or more of the contacted nucleic acids and the bacterial nucleic acid, wherein the combination of nucleic acids comprises at least two nucleic acid molecules selected from the group consisting of:
   a) a combination of a nucleic acid molecule consisting of SEQ ID NO: 2 and a nucleic acid molecule consisting of SEQ ID NO: 78;
   b) a combination of a nucleic acid molecule which exhibits 90% identity with SEQ ID NO: 2, and a nucleic acid molecule which exhibits 90% identity with SEQ ID NO: 78; and
   c) a combination of a nucleic acid molecules, each of which is a full complement of (i) SEQ ID NO: 2, (ii) SEQ ID NO: 78, (iii) a nucleic acid molecule which exhibits 90% identity with SEQ ID NO: 2, or (iv) a nucleic acid molecule which exhibits 90% identity with SEQ ID NO: 78, wherein any species of the taxonomic unit of Enterobacteriaceae, but no species of another taxonomic unit, is detected by formation of the hybrid nucleic acids.

9. A method for amplifying bacterial DNA of any species of the taxonomic unit of Enterobacteriaceae, comprising a first amplification step in which the DNA for any species of the taxonomic unit of Enterobacteriaceae, and no species of another taxonomic unit is amplified with conserved primers to obtain a first amplification fragment, and, optionally, at least one further amplification step (EN) in which parts of the first amplification fragment, which are specific for species of the taxonomic unit of Enterobacteriaceae, are multiplied with nested, increasingly variable primers, and optionally, a further step in which the DNA fragments obtained by amplification, which are specific for species of the taxonomic unit of Enterobacteriaceae, are detected by means of probes, wherein the primers used in the first amplification step comprise a combination of at least two nucleic acid molecules, selected from the group consisting of:
   a) a combination of a nucleic acid molecule consisting of SEQ ID NO: 2 and a nucleic acid molecule consisting of SEQ ID NO: 78;
   b) a combination of a nucleic acid molecule of a nucleic acid which exhibits 90% identity with SEQ ID NO: 2, and a nucleic acid which exhibits 90% identity with SEQ ID NO: 78, and;
   c) a combination of nucleic acid molecules, each of which is a full complement of (i) SEQ ID NO: 2, (ii) SEQ ID NO: 78, (iii) a nucleic acid molecule which exhibits 90% identity with SEQ ID NO: 2, or (iv) a nucleic acid molecule which exhibits 90% identity with SEQ ID NO: 78.

10. The method of claim 7, wherein the groups which allow a direct or indirect reaction are selected from the group consisting of antibodies, antigens, enzymes, and substances with affinity to enzymes or enzyme complexes.

* * * * *